(12) United States Patent
Kaibuchi et al.

(10) Patent No.: US 6,660,837 B1
(45) Date of Patent: Dec. 9, 2003

(54) MODIFIED PROTEIN DERIVED FROM PROTEIN KINASE N

(75) Inventors: Kozo Kaibuchi, Ikoma (JP); Yoshitaka Ono, Toyonaka (JP); Akihiro Iwamatsu, Yokohama (JP)

(73) Assignee: Kirin Beer Kabushiki Kaisha, Tokyo-To (JP)

( * ) Notice: Subject to any disclaimer, the term of this patent is extended or adjusted under 35 U.S.C. 154(b) by 0 days.

(21) Appl. No.: 08/685,852

(22) Filed: Jul. 24, 1996

(30) Foreign Application Priority Data

| Sep. 14, 1995 | (JP) | ............................................. 7-262552 |
| Dec. 5, 1995 | (JP) | ............................................. 7-344606 |
| Mar. 8, 1996 | (JP) | ............................................. 8-080549 |
| Apr. 11, 1996 | (JP) | ............................................. 8-114226 |

(51) Int. Cl.$^7$ ........................... C07K 14/00; C12N 9/12
(52) U.S. Cl. .......................... 530/350; 530/300; 514/2; 514/12; 435/194; 435/320.1; 435/252.3; 435/252.33; 435/325; 536/23.1; 536/23.2; 536/23.5
(58) Field of Search ............................. 435/194, 320.1, 435/252.3, 252.33, 325; 536/23.1, 23.2, 23.5; 530/300, 350; 514/2, 12

(56) References Cited

PUBLICATIONS

Palmer et al., Eur. J. Biochem. 227, 344–351 (1995).*
Mukai et al., Biochem. Res. Commun. 199, 897–904 (1994).*
Palmer et al., FEBS Letters 356, 5–8 (1994).*
Adamson et al., "Post–Translational Modifications of p21$^{rho}$ Proteins", The Journal of Biological Chemistry, vol. 267, No. 28, (1992) pp. 20033–20038.
Adler et al., "UV Irradiation and Heat Shock Mediate JNK Activation via Alternate Pathways", The Journal of Biological Chemistry, vol. 270, No. 44, (1995) pp. 26071–26077.
Amano et al., "Rho–Activated Serine/Threonine Kinase PKN", vol. 67, No. 7, (1995) p. 649.
Amano et al., "Identification of a Putative Target for Rho as the Serine–Threonine Kinase Protein Kinase N", Science, vol. 271, (1996) pp. 648–650.
Ando et al., "Functions and Modes of Action of Small G Proteins: The Signal Transduction Pathways . . . ", Experimental Medicine, vol. 11, No. 15, (Extra Edition) (1993) pp. 1973–1980, Title page only.
Beggs et al., "Cloning and Characterization of Two Human Skeletal Muscle a–Actinin Genes Located on Chromosomes 1 and 11", The Journal of Biological Chemistry, vol. 267, No. 13, (1992) pp. 9281–9288.
Bennett et al., "Isolation and Some Properties of Macrophage a–Actinin: Evidence That it is Not an Actin Gelling Protein", Biochemistry, vol. 23, (1984) pp. 5081–5086.

Bennett, "Spectrin–Based membrane Skeleton: A Multipotential Adaptor Between Plasma Membrane and Cytoplasm", Physiological Reviews, vol. 70, No. 4, (1990) pp. 1029–1065.
Blanchard et al., "The Structure and Function oa a–Actinin", Journal of Muscle Research and Cell Motility, vol. 10, (1989) pp. 280–289.
Burridge et al., "Non–Musle a–Actinins are Calcium–Sensitive Actin–Binding Proteins", Nature, vol. 294, (1981) pp. 565–567.
Cano, "Parallel Signal Processing Among Mammalian MAPKs", TIBS, vol. 20, (1995) pp. 117–122.
Chong et al., "The Small GTP–Binding Protein Rho Regulates a Phosphatidylinositol 4–Phosphate 5–Kinase in Mammalian Cells", Cell, vol. 79, (1994) pp. 507–513.
Collard, "Signaling Pathways Regulated by RHO–Like Proteins: A Possible Role in Tumor Formation and Metastasis (Review)", International Journal of Oncology, vol. 8, (1996), pp. 131–138.
Coso et al., "The Small GTP–Binding Proteins RAC1 and Cdc42 Regulate the Activity of the JNK/SAPK Signaling Pathway", Cell, vol. 81, (1995), pp. 1137–1146.
Davis, "MAPKs: New JNK Expands the Group", TIBS, Special Issue, vol. 19, (1994) pp. 470–473.
Derijard et al., "JNK1: A Protein Kinase Stimulated By UV Light and Ha–Ras That Binds and Phosphorylates the c–Jun Activation Domain", Cell, vol. 76, (1994) pp. 1025–1037.
Devary et al., "Rapid and Preferential Activation of the c–Jun Gene During the Mammalian UV Response", Molecular and Cellular Biology, (1991), pp. 2804–2811.
Devary et al., "NF–κB Activation by Ultraviolet Light Not Dependent on a Nuclear Signal", Science, vol. 261, (1993), pp. 1442–1445.
Drgonova et al., "Rho1p, a Yeast Protein at the Interface Between Cell Polarization and Morphogenesis", Science, vol. 272, (1996), pp. 277–279.
Dubreuil, "Structure and Evolution of the Actin Crosslinking Proteins", BioEssays, vol. 13, No. 5, (1991) pp. 219–226.

(List continued on next page.)

Primary Examiner—Christopher S. F. Low
Assistant Examiner—Chih-Min Kam
(74) Attorney, Agent, or Firm—Foley & Lardner

(57) ABSTRACT

A object of the present invention is to provide a peptide inhibiting tumorigenesis or metastasis. The present invention is a peptide or derivatives thereof comprising a modified amino acid sequence of Protein Kinase N having the activated Rho protein binding activity and not having protein kinase activity, and a peptide or derivatives thereof comprising a modified amino acid sequence of Protein Kinase N inhibiting the protein kinase activity of Protein Kinase N or the enhancement of the activity and not having protein kinase activity.

5 Claims, 41 Drawing Sheets

OTHER PUBLICATIONS

Duhaiman et al., "Isolation of Brain a–Actinin. Its Characterization and a Comparison of Its Properties with Those of Muscle of a–Actinin", Biochemistry, vol. 23, (1984), pp. 1600–1608.

Fukami et al., "Requirement of Phosphatidylinositol 4,5–Bisphosphate for a–Actinin Function", Nature, vol. 359, (1992), pp. 150–152.

Fukami et al., "Identification of a Phosphatidylinositol 4,5–Bisphosphate–Binding Site in Chicken Skeletal Muscle a–Actinin", The Journal of Biological Chemistry, vol. 271, No. 5, (1996), pp. 2646–2650.

Gonda et al., "Role o Guanine Nucleotide–Binding Proteins–Ras–Family or Trimeric Proteins or Both . . . ", Proc. Natl. Acad. Sci., vol. 93, (1996), pp. 1340–1345.

Hart et al., "Cellular Transformation and Cuanine Nucleotide Exchange Activity Are Catalyzed by a Common Domain on the dbl Oncogene Product", The Journal Biological Chemistry, vol. 269, No. 1, (1994), pp. 62–65.

Hill et al., "The Rho Family GTPases RhoA, Rac1, and CDC42Hs Regulate Transcriptional Activation by SRF", Cell, vol. 81, (1995), pp. 1159–1170.

Hirata et al., "Involvement of rho p21 in the GTP–Enhanced Calcium Ion Sensitivity of Smooth Muscle Contraction", The Journal of Biological Chemistry, vol. 267, No. 13, (1992) pp. 8719–8722.

Hisanaga et al., "Structure of the Peripheral Domains of Neurofilaments Revealed by Low Angle Rotary Shadowing", J. Mol. Biol., vol. 202, (1988), pp. 297–305.

Hisanaga et al., "Molecular Architecture of the Neurofilament II. Reassembly Process of Neurofilament L Protein in Vitro", J. Mol. Biol., vol. 211, (1990) pp. 871–882.

Hong et al., "Cloning and Analysis of cDNA Clones for Rat Kidney a–Spectrin", The Journal of Biological Chemistry, vol. 264, No. 22, (1989) pp. 12758–12764.

Honore et al., "Nucleotide Sequence of cDNA Covering the Complete Coding Part of the Human Vimentin Gene", Nucleic Acids Research, vol. 18, No. 22, (1990), pp. 6692.

Horii, "A Novel Oncogene, ost, Encodes A Guanine Nucleotide Exchange Factor that Potentially Links Rho and Rac Signaling Pathways", The EMBO Journal, vol. 13, No. 20, (1994) pp. 4776–4786.

Inagaki et al., "Spatiotemporal Distribution of Protein Kinase and Phosphatase Activities", TIBS, Special Issue, vol. 19, (1994), pp. 448–452.

Ishizaki et al., "The Small GTP–Binding Protein Rho Binds to and Activates a 160 kDa Ser/Thr Protein Kinase Homologous to Myotonic Dystrophy Kinase", The EMBO Journal, vol. 15, No. 8, (1996), pp. 1885–1893.

Julien et al., "The Structure of a Human Neurofilament Gene (NF–L): a Unique Exon–Intron Organization in the Intermediate Filament Gene Family", Biochem. Biophys. Acta., vol. 909, (1987), pp. 10–20.

Katayama et al., "The Posttranslationally Modified C–Terminal Structure of Bovine Aortic Smooth Muscle rhoA p21", The Journal of Biological Chemistry, vol. 266, No. 19, (1991) pp. 12639–12645.

Khosravi–Far et al., "Activation of Rac1 RhoA, and Mitogen–Activated Protein Kinases is Required for Ras Transformation", Molecular and Cellular Biology, vol. 15, No. 11, (1995) pp. 6443–6453.

Kimura et al., "Rho Returns: Its Targets in Focal Adhesions", Science, vol. 273, (1996), pp. 245–248.

Kishi et al., "Regulation of Cytoplasmic Division of Xenopus Embryo by rho p21 and Its Inhibitory GDP/GTP Exchange Protein (rho GDI)", Cell Biol., vol. 120, (1993) pp. 1187–1195.

Kitagawa et al., "The Role of the Unique Motifs in the Amino–Terminal Region of PKN on Its Enzymatic Activity", Biochemical and Biophysical Research Commun., vol. 220, (1996) pp. 963–968.

Lamarche et al., "Gaps for Rho–Related GTPases", TIB, vol. 10, No. 12, (1994) pp. 436–440.

Landon et al., "Properties of Two Isoforms of Human Blood Platelet a–Actinin", Eur. J. Biochem., vol. 153, (1985) pp. 231–237.

Laudanna et al., "Role of Rho in Chemoattractant–Activated Leukoctye Adhesion Through Integrins", Science, vol. 271, (1996) pp. 981–983.

Lebowitz et al., "Evidence that Farnesyltransferase Inhibitiors Suppress Ras Transformation Rho Activity", Molecular and Cellular Biology, (1995) pp. 6613–6622.

Lees et al., "The Structure and Organization of the Human Heavy Neurofilament Subunit (NF–H) and the Gene Encoding It", The EMBO Journal, vol. 7, No. 7, (1988) pp. 1947–1955.

Leung et al., "A Novel Serine/Threonine Kinase Binding the Ras–Related RhoA GTPase Which Translocates the Kinase to Peripheral Membranes", J. Biol. Chem., vol. 270, No. 19, (1995) pp. 29051–29054.

Mabuchi et al., "A Rho–Like Protein is Involved in the Organization of the Contractile Ring in Dividing Sand Dollar Eggs", Zygote 1, (1993) pp. 325–331.

Madaule et al., "A Novel Partner for the GTP–Bound Forms of rho and rac", FEBS Letters, vol. 377, (1995) pp. 243–248.

Manser et al., "A Non–Receptor Tyrosine Kinase that Inhibits the GTPase Activity of $p21^{cdc42}$", Nature, vol. 363, (1993) pp. 364–367.

Manser et al., "A Brain Serine/Threonine Protein Kinase Activated by Cdc42 and Rac1", Nature, vol. 367, (1994) pp. 40–46.

Maytin et al., "Separate Glucocorticoid, Heavy Metal, and Heat Shock Domains in Thymic Lymphocytes", Journal of Biological Chemistry, vol. 258, No. 20, (1983) pp. 12718–12722.

Matsui et al., "Rho–Associated Kinase, A Novel Serine/Threonine Kinase, as a Putative Target for the Small GTP Binding Protein Rho", The Embo Journal, vol. 15, No. 9, (1996) pp. 2208–2216.

Millake et al., "The cDNA Sequence of a Human Placental a–Actinin", Nucleic Acids Research, vol. 17, No. 16, (1989) pp. 6725.

Minden et al. "Selective Activation of the JNK Signaling Cascade and c–Jun Transcriptional Activity by the Small GTPases Rac and Cdc42Hs", Cell, vol. 81, (1995), pp. 1147–1157.

Morii et al., "A rho Gene Product in Human Blood Platelets", The Journal of Biological Chemistry, vol. 267, No. 29, (1992) pp. 20921–20926.

Mukai et al., "A Novel Protein Kinase With Leucine Zipper–Like Sequences . . . ", Biochemical and Biophysical Research Commun., vol. 199, No. 2, (1994) pp. 897–904.

Mukai et al., "Activation of PKN, A Novel 120–KDa Protein Kinase with Leucine Zipper–Like Sequence, By Unsaturated Fatty Acids . . . ", Biochem. and Biophys. Research Commun., vol. 204, No. 1, (1994) pp. 348–356.

Mukai et al., "Xenopus PKN: Cloning and Sequencing of the cDNA and Identification of Conserved Domains", Biochimica et Biophysica Acta, vol. 1261, (1995) pp. 296–300.

Mukai et al., "PKN Associates and Phosphorylates the Head–Rod Domain of Neurofilament Protein", Journal of Biol. Chem., vol. 271, No. 16, (1996) pp. 9816–1626.

Myers et al., "The Human Mid–Sized Neurofilament Subunit: A Repeated Protein Sequence and the Relationship of its Gene to the Intermediate Filament Gene Family", The EMBO J., vol. 6, No. 6, (1987) pp. 1617–1626.

Nakagawa et al., "Two Distinct Functions the Carboxyl–Terminal Tail Domain of NF–M Upon Neurofilament . . . ", The Journal of Cell Biology, vol. 129, No. 2, (1995) pp. 411–429.

Nakamura et al., "Effect of Phosphorylation on 68 KDa Neurofilament Subunit Protein Assembly by the Cyclic AMP Depend Protein Kinase in Vitro", Biochem. Biophys. Res. Commun., vol. 169, No. 2, (1990) pp. 744–750.

Nishiyama et al., "Regulation of Cytoskeleton by Rho", Experimental Medicine, vol. 12, No. 8, (1994) pp. 991–996, Title page only.

Noda et al., "Involvement of rho in GTPys–Induced Enhancement of Phosphorylation of 20 kDa Chain in Vascular Smooth Muscle Cells . . . ", FEBS Letters, vol. 367, (1995) p. 246–250.

Nonaka et al., "A Downstream Target of RHO1 Small GTP–Binding Protein is PKC1, a Homolog of Protein Kinase C, Which Leads to Activation . . . ", The EMBO Journal, vol. 14, No. 23, (1995) pp. 5931–5938.

Nusrat et al., "Rho Protein Regulates Tight Junctions and Perijunctional Actin Organization in Polarized Epithelia", Proc. Natl. Acad. Sci., vol. 92, (1995) pp. 10629–10633.

Palmer et al., "Identification of Multiple, Novel, Protein Kinase C–Related Gene Products", FEBS Letters, vol. 356, (1994) pp. 5–8.

Peterson et al., "Microinjection of Recombinant p21 Induces Rapid Changes in Cell Morphology", The Journal of Cell Biology, vol. 111, (1990), pp. 1001–1007.

Prendergast et al., "Critical Role of Rho in Cell Transformation by Oncogenic Ras", Oncogene, vol. 10, (1996), pp. 2289–2296.

Oadota et al., "Identification of Yeast Rho1p GTPase as a Regulatory Subunit of 1,3–B–Glucan Synthase", Science, vol. 272, (1996), pp. 279–281.

Qiu et al., "A Role for Rho in Ras Transformation", Proc. Natl. Acad. Sci., vol. 92, (1995) pp. 11781–11785.

Reid et al., "Rhotekin, a New Putative Target for Rho Bearing Homology to a Serine/Threonine Kinase, PKN, and Rhophilin in the Rho–Binding Domain", The Journal of Biol. Chem., vol. 271, No. 23, (1996) pp. 13556–13560.

Ridley et al., "Signal Transduction Pathways Regulating Rho–Mediated Stress Fibre Formation: Requirement for a Tyrosine Kinase", The EMBO Journal, vol. 13, No. 11, (1994) pp. 2600–2610.

Ridley et al., "The Small GTP–Binding Protein rho Regulates the Assembly of Focal Adhesions and Actin Stress Fibers in Response to Growth Factors", Cell, vol. 70, (1992), pp. 389–399.

Shibata et al., "Characterization of the Interaction Between RhoA and the Amino–Terminal Region of PKN", FEBS Letters, vol. 385, (1996) pp. 221–224.

Sihag et al., "In Vivo Phosphorylation of Distinct Domains of the 70–Kilodalton Neurofilament Subunit Involves Different Protein Kinases", The Journal Biological Chemistry, vol. 264, No. 1, (1989) pp. 457–464.

Takaasishi et al., "Involve of Rho p21 Small GTP–Binding Protein and Its Regulation in the HGF–Induced Cell Motility", Oncogene, vol. 9, (1994) pp. 273–279.

Zhang et al., "Rho Family GTPase Regulate p38 Mitogen–Activated Protein Kinase Through the Downstream Mediator Pak1", Journal of Biol. Chem., vol. 270, No. 41, (1995) pp. 23934–23936.

Takai et al., "Rho as a Regulator of the Cytoskeleton", TIBS, vol. 20, (1995) pp. 227–231.

Tominaga et al., "Inhibition of PMA–Induced, LFA–1–Dependent Lymphocyte Aggregation by ADP Ribosylation of Small Molecular Weight GTP Binding Protein, rho", J. of Cell Biol., vol. 6, (1993) pp. 1529–1537.

Vojtek et al., "Rho Family Members: Activators of MAP Kinase Cascades", Cell, vol. 82, (1995) pp. 527–529.

Wasenius et al., "Primary Structure of the Brain a–Spectrin", The Journal of Cell Biology, vol. 108, (1989) pp. 79–93.

Watanabe et al., "Protein Kinase N (PKN) and PKN–Related Protein Rhophilin as Targets of Small GTPase Rho", Science, vol. 271, (1996) pp. 645–648.

Welch et al., "Cellular and Bichemical Events in Mammalian Cells During and After Recovery From Physiological Stress", The Journal of Cell Biology, vol. 103, (1986) pp. 2035–2052.

Yoshioka et al., "Participation of rhop21 in Serum–Dependent Invasion by Rat Ascites Hepatoma Cells", FEBS Letters, vol. 372, (1995) pp. 25–28.

Youssouflan et al., "Cloning and chromosomal Localization of the Human Cytoskeletal a–Actinin Gene Reveals Linkage to the B–Spectrin Gene", Am. J. Hum. Genet., vol. 47, (1990) pp. 62–72.

Zhang et al., "Activation of Platelet Phosphatidylinositide 3–Kinase Requires the Small GTP–Binding Protein Rho", The Journal of Biol. Chem., vol. 268, No. 30, (1993) pp. 22251–22254.

* cited by examiner

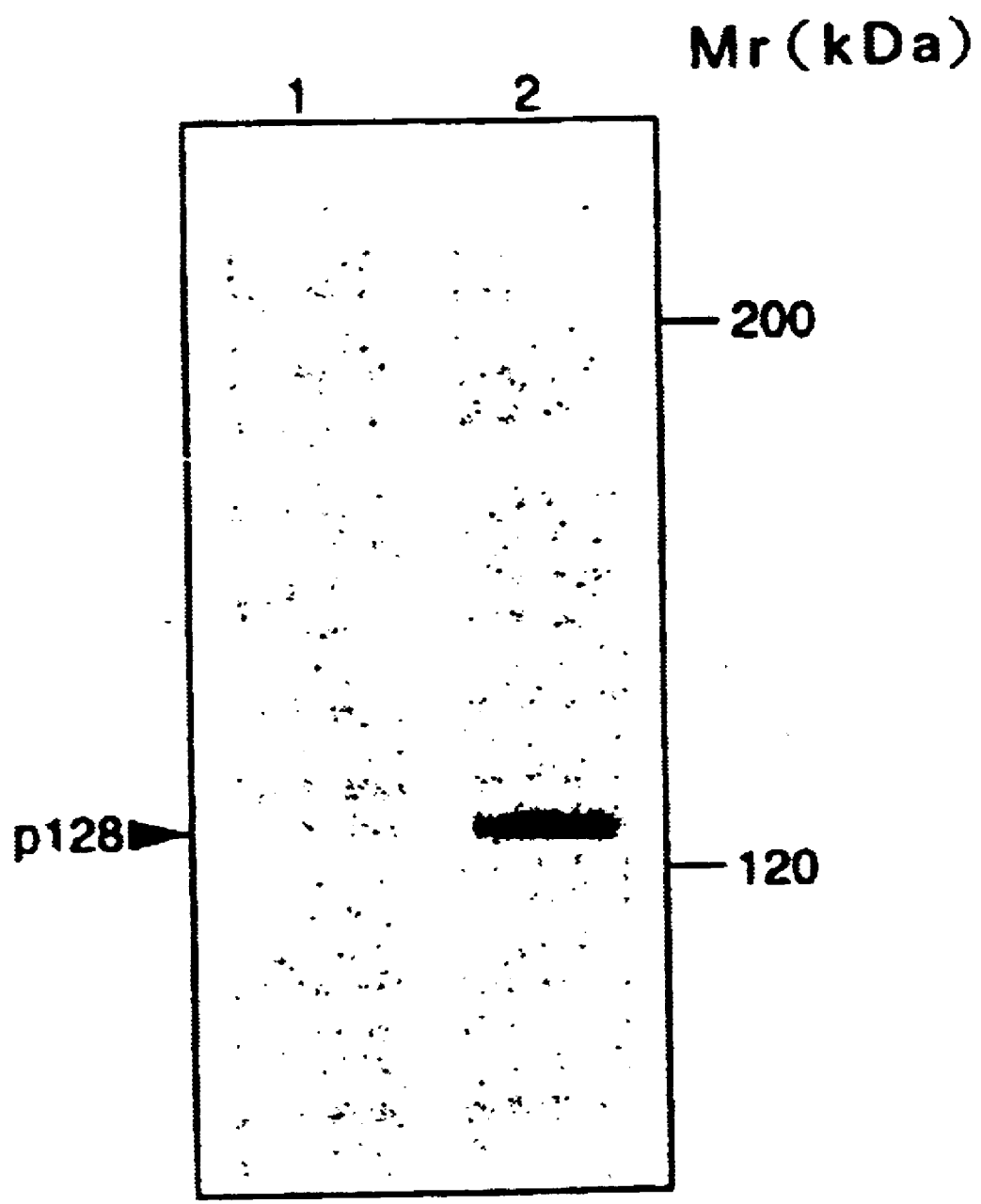
F I G. 2

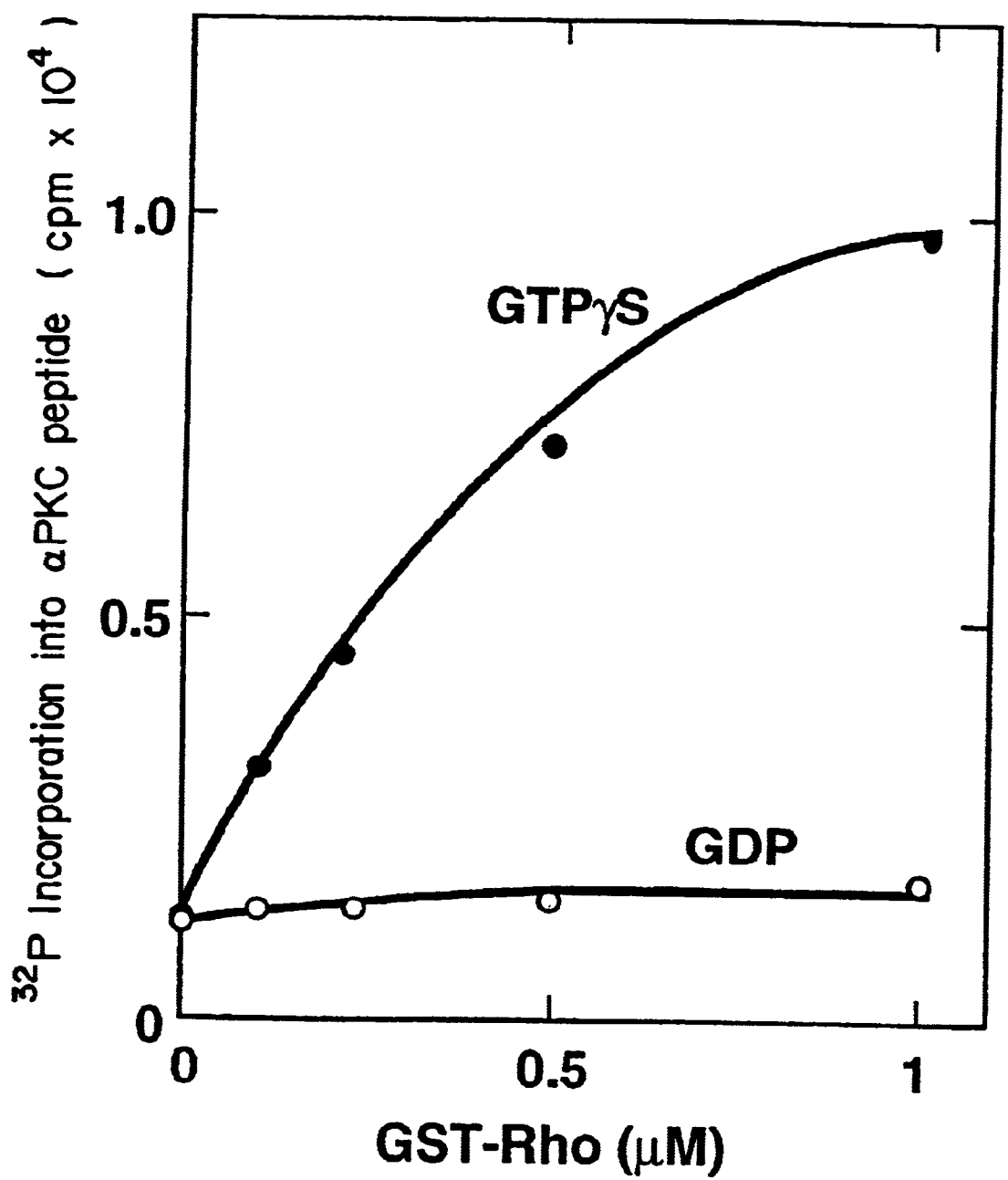
F I G. 4

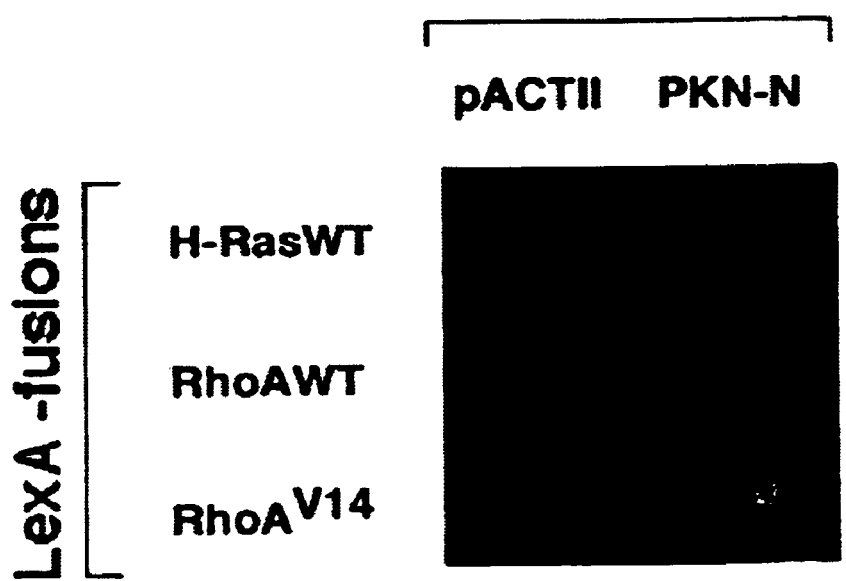
F I G. 9

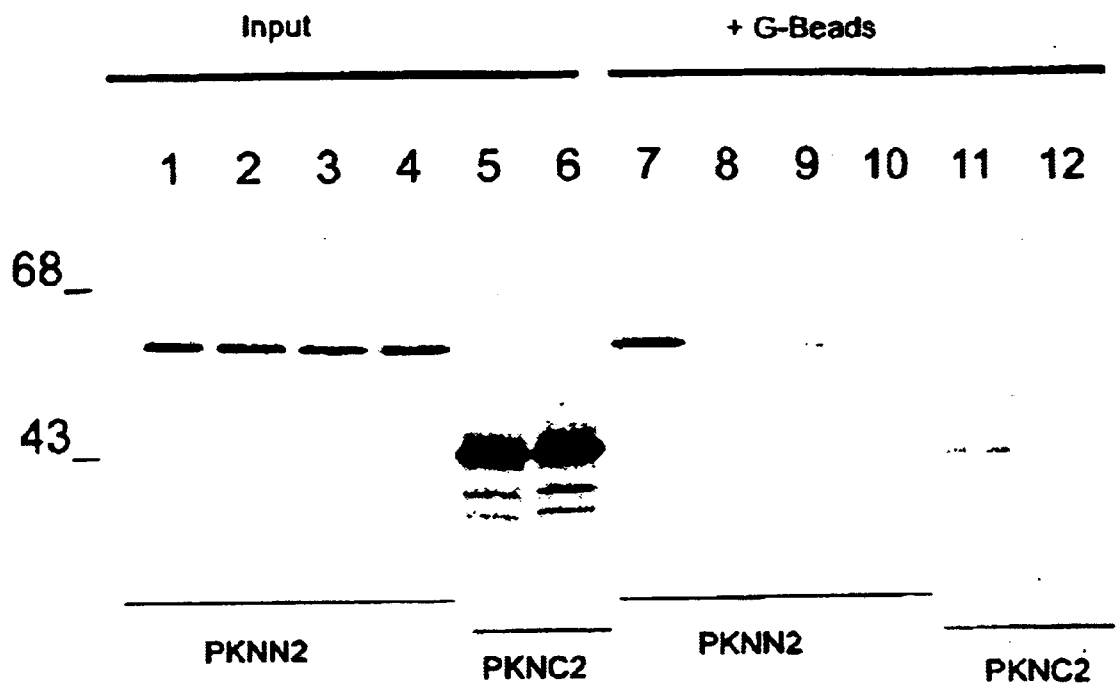
F I G. 12
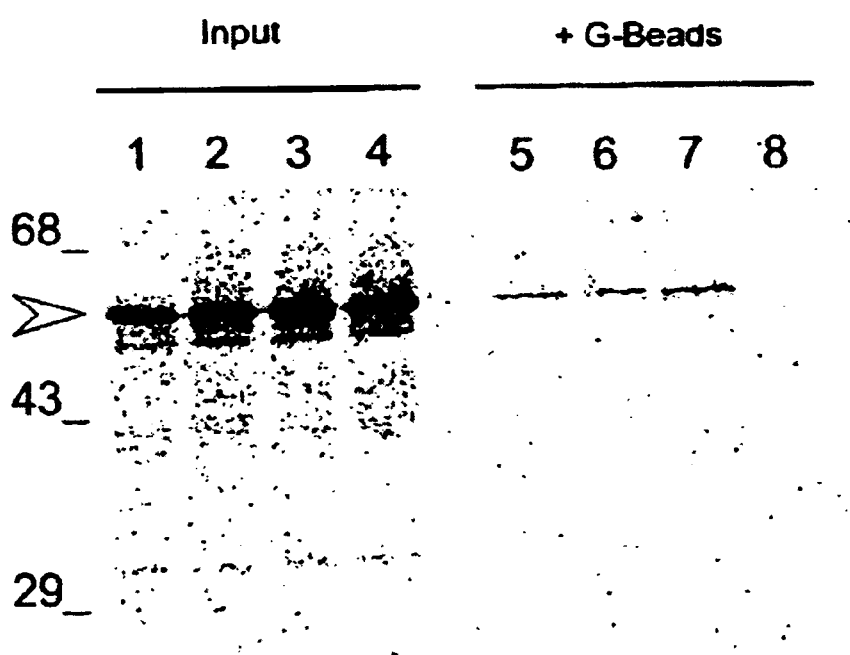
F I G. 13

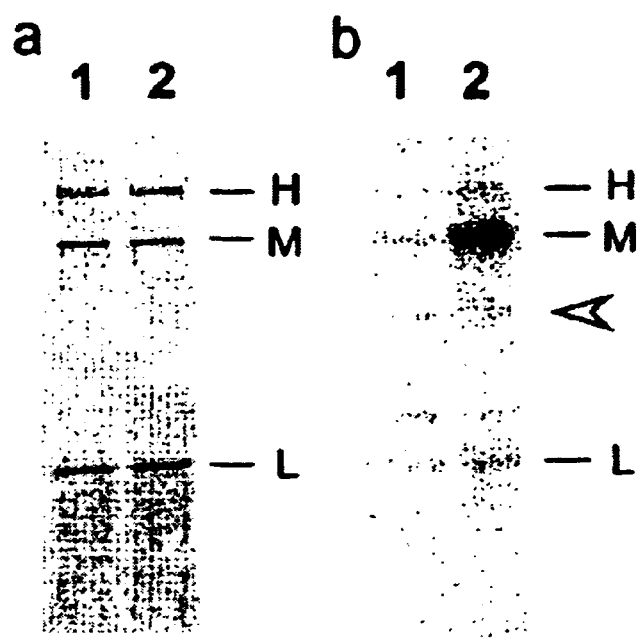
F I G. 14
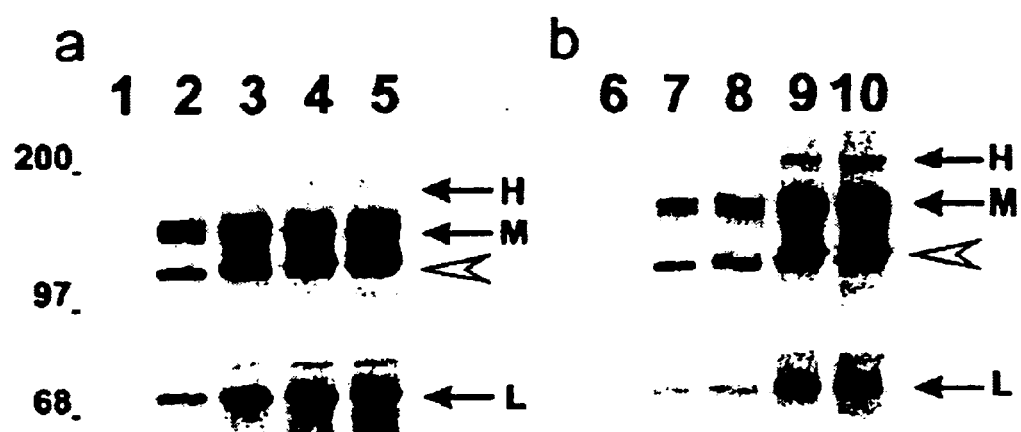
F I G. 15

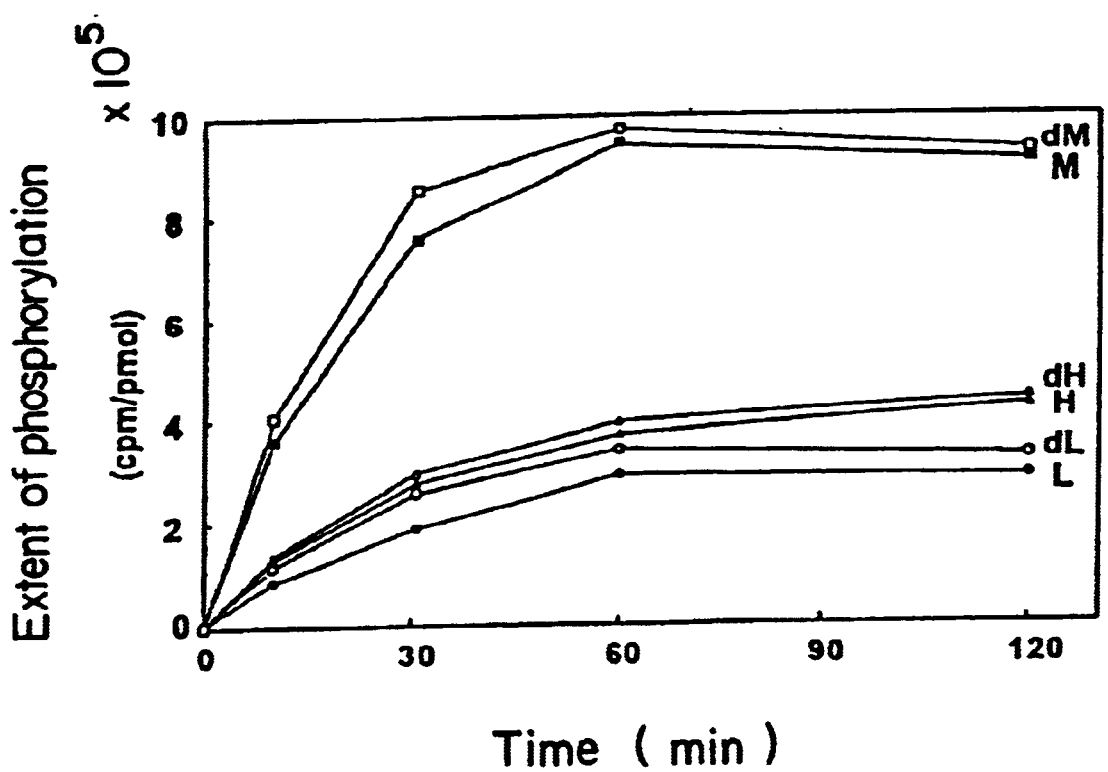
F I G. 16

1) pBTM116 + pVP16

2) pBTM116 + pVP/PKN-N 3) pBTM116 + pVP/PKN-C 4) pBTM/PKN-N + pVP/PKN-C 5) pBTM/PKN-C + pVP/PKN-N

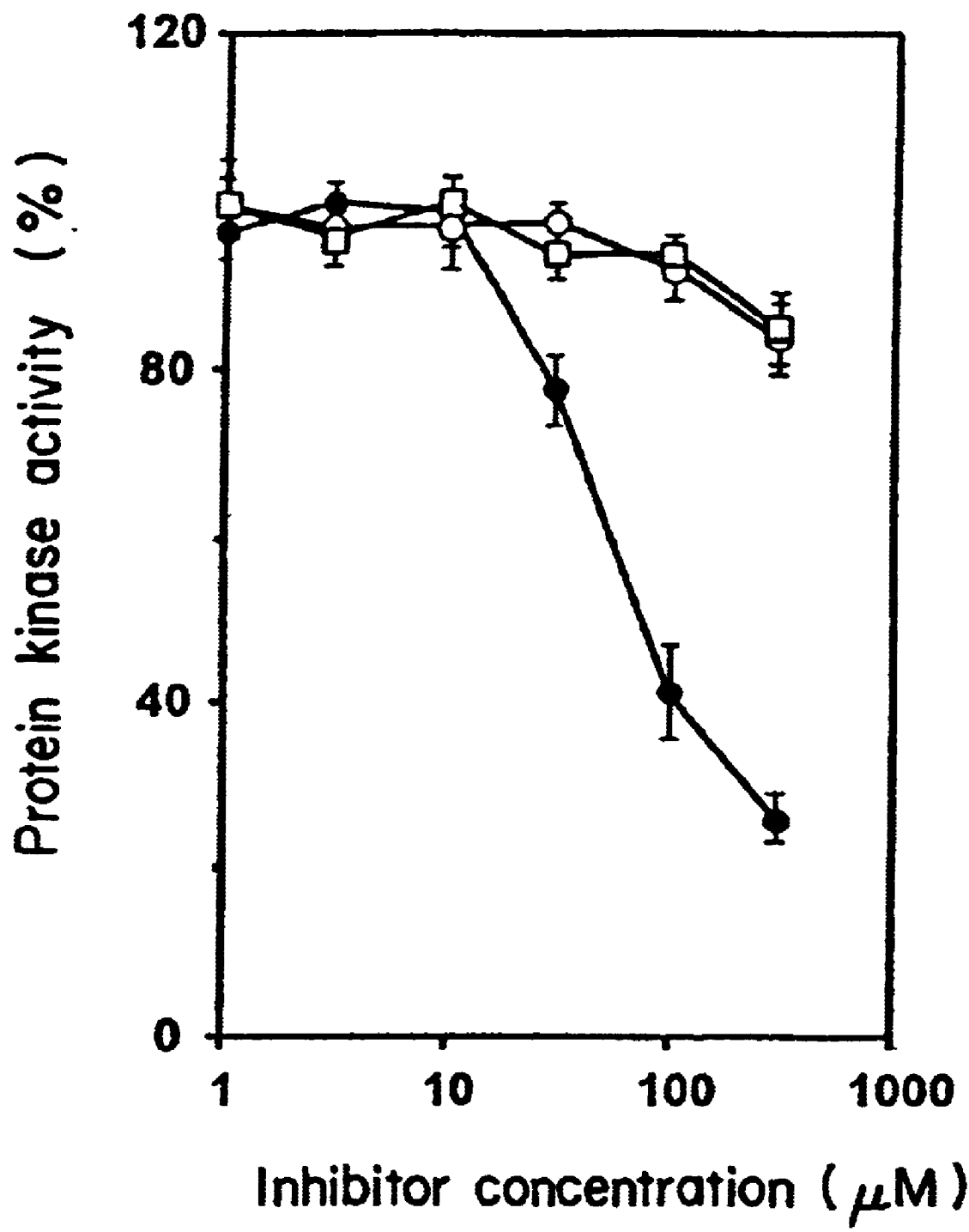
F I G. 22

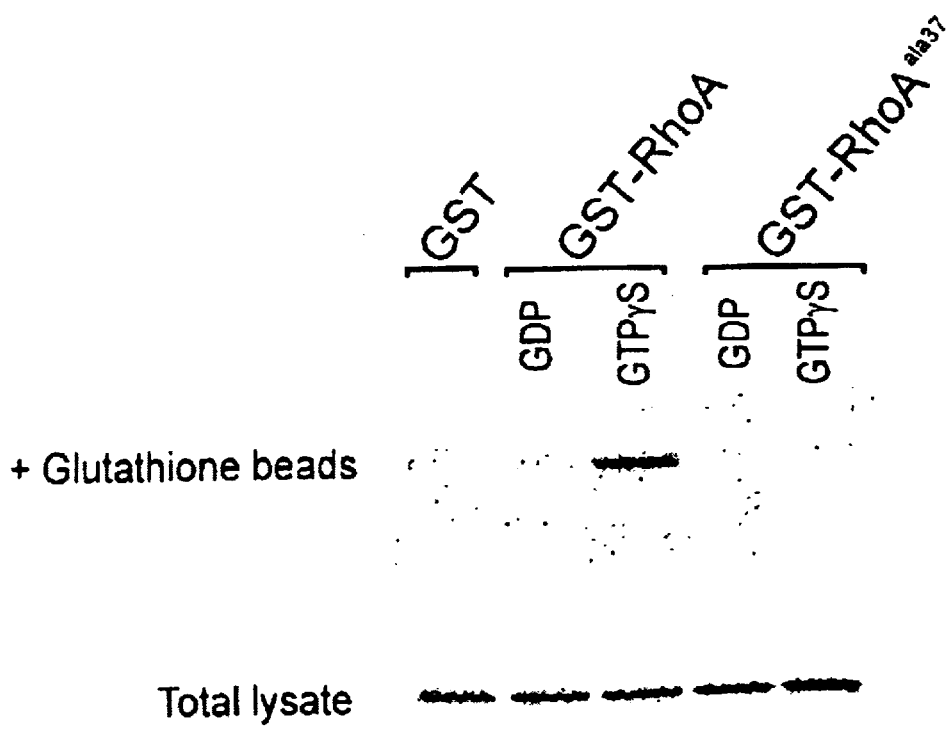
F I G. 26
| Synthetic peptide concentration [μM] | 3 | 10 | 30 | 100 | Amino acid residues |
|---|---|---|---|---|---|
| | — | — | — | — | 31-53 |
| | — | — | — | • | 54-73 |
| | — | — | — | | 74-93 |
| | — | — | — | — | 94-113 |
| | — | — | — | — | 114-133 |
F I G. 27

Peptide concentration  0.1 0.3  1   3   10 30
($\mu$M)

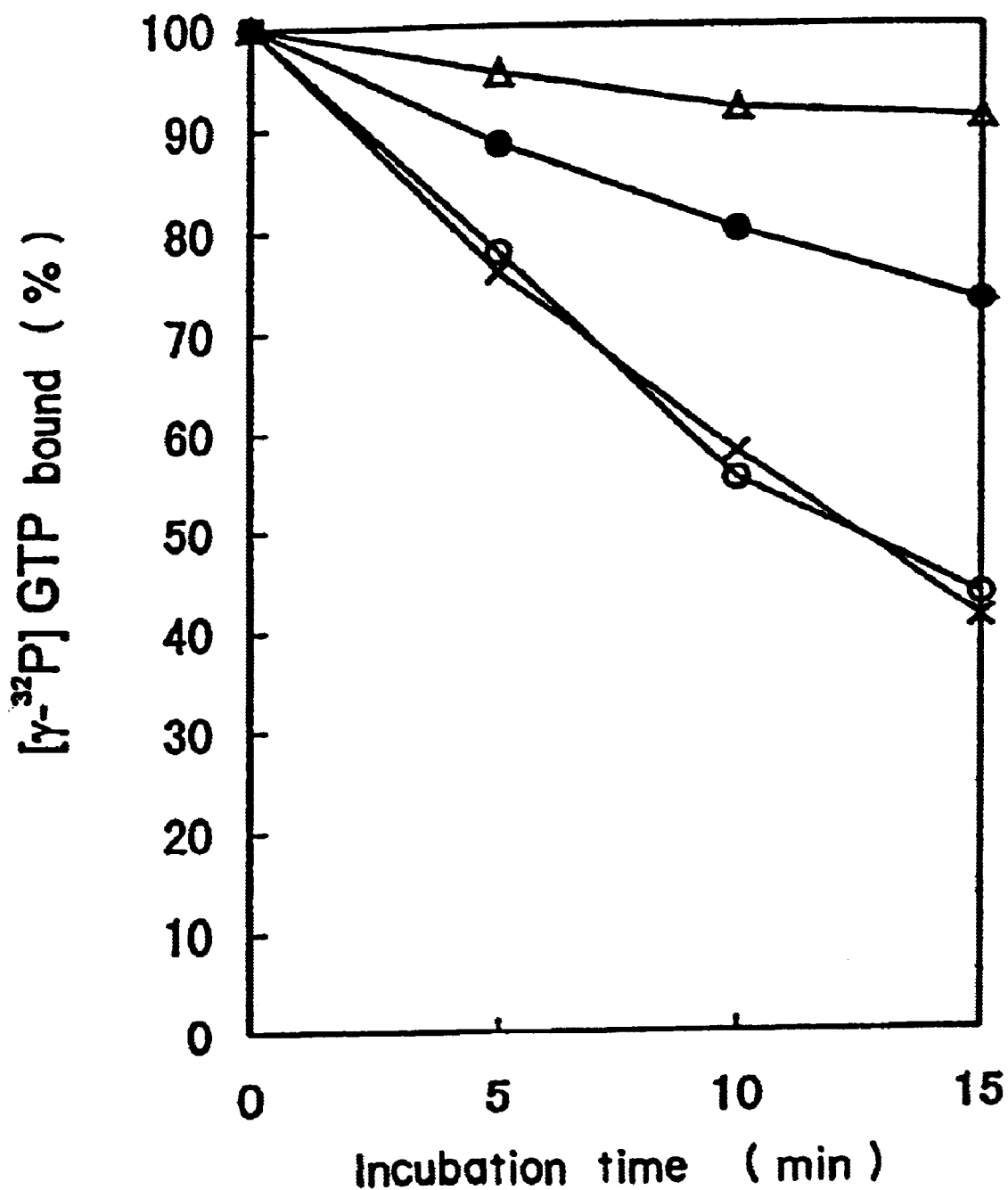
F I G. 29

NIH 3T3

Rat-1

Balb/c 3T3

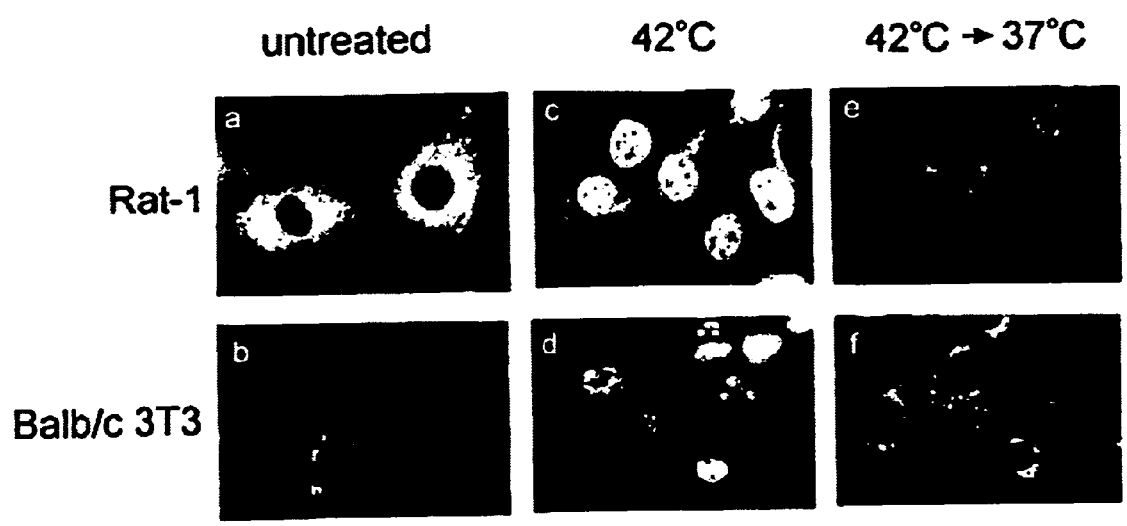
F I G. 35 a. untreated    b. sodium arsenite a. untreated    b. starved.    c. starv + FCS a. untreated    b. 42°C    c. 44°C

29—
      ─────────────      ─── ── ─── ──
           Input              +G-beads
```

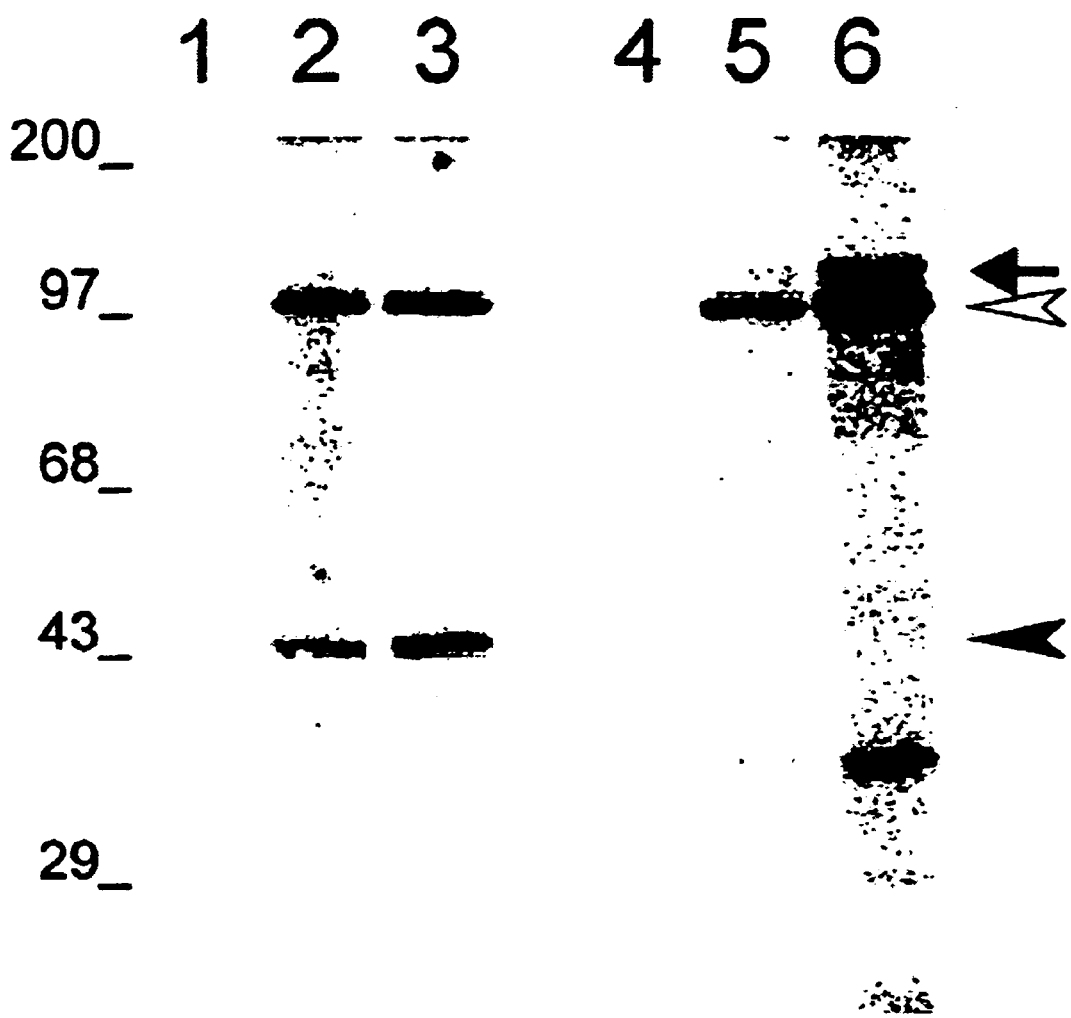
F I G. 49

# MODIFIED PROTEIN DERIVED FROM PROTEIN KINASE N

FIELD OF THE INVENTION

The present invention relates to a modified amino acid sequence of Protein Kinase N, and more particularly to a modified amino acid sequence of PKN having activated Rho protein binding activity.

BACKGROUND OF THE INVENTION

A group of low-molecular-weight GTP-binding proteins (G-proteins) with molecular weights of 20,000–30,000 with no subunit structures are observed in organisms. To date, over fifty or more members have been found as the super family of the low-molecular-weight G-proteins in a variety of organisms, from yeast to mammals. The low-molecular-weight G-proteins are divided into four families of Ras, Rho, Rab and the others based on homologies of amino acid sequences. It has been revealed that the small G-proteins control a variety of cellular functions. For example, the Ras protein is considered to control cell proliferation and differentiation, and the Rho protein is considered to control cell morphological change, adhesion and motility.

The Rho protein, having GDP/GTP-binding activity and intrinsic GTPase activity, is believed to be involved in cytoskeletal rearrangement in response to extracellular signals such as lysophosphatidic acid (LPA) and certain growth factors. When the inactive GDP-binding Rho is stimulated, it is converted to the active GTP-binding Rho protein (hereinafter referred to as "the activated Rho protein") by GDP/GTP exchange proteins such as Smg GDS, Dbl or Ost. The activated Rho protein then acts on target proteins to form stress fibers and focal contacts, thus inducing the cell adhesion and motility (Experimental Medicine, Vol. 12, No. 8, 97–102 (1994); Takai, Y. et al., Trends Biochem. Sci., 20, 227–231 (1995)). On the other hand, the intrinsic GTPase activity of the Rho protein converts the activated Rho protein to the GDP-binding Rho protein. This intrinsic GTPase activity is activated by what is called GTPase-activating proteins (GAP) (Lamarche, N. & Hall, A. et al., TIG, 10, 436–440 (1994)).

The Rho family proteins, including RhoA, RhoB, RhoC, Rac1, Rac2 and Cdc42, share more than 50% sequence identity with each other. The Rho family proteins are believed to be involved in inducing the formation of stress fibers and focal contacts in response to extracellular signals such as lysophosphatidic acid (LPA) and growth factors (A. J. Ridley & A. Hall, Cell, 70, 389–399 (1992); A. J. Ridley & A. Hall, EMBO J., 13, 2600–2610 (1994)). The subfamily Rho is also considered to be implicated in physiological functions associated with cytoskeletal rearrangements, such as cell morphological change (H. F. Parterson et al., J. Cell Biol., 111, 1001–1007 (1990)), cell adhesion (Morii, N. et al., J. Biol. Chem., 267, 20921–20926 (1992); T. Tominaga et al., J. Cell Biol., 120, 1529–1537 (1993); Nusrat, A. et al., Proc. Natl. Acad. Sci. USA, 92, 10629–10633 (1995)*; Landanna, C. et al., Science, 271, 981–983 (1996)*, cell motility (K. Takaishi et al., Oncogene, 9, 273–279 (1994), and cytokinesis (K. Kishi et al., J. Cell Biol., 120, 1187–1195 (1993); I. Mabuchi et al., Zygote, 1, 325–331 (1993)). (An asterisk hereinafter indicates a publication issued after the first filed application which provides the right of the priority of the present application.) In addition, it has been suggested that the Rho is involved in the regulation of smooth muscle contraction (K. Hirata et al., J. Biol. Chem., 267, 8719–8722 (1992); M. Noda et al., FEBS Lett., 367, 246–250 (1995); M. Gong et al., Proc. Natl. Acad. Sci. USA, 93, 1340–1345 (1996)*; K. Kimura, et al., Science, 273, 245–248(1996)*), and the expression of phosphatidylinositol 3-kinase (PI3 kinase) (J. Zhang et al., J. Biol. Chem., 268, 22251–22254 (1993)), phosphatidylinositol 4-phosphate 5-kinase (PI 4,5-kinase) (L. D. Chong et al., Cell, 79, 507–513 (1994)) and c-fos (C. S. Hill et al., Cell, 81, 1159–1170 (1995)).

Recently, it has also be found that Ras-dependent tumorigenesis is suppressed when the Rho protein of which the amino acid sequence has been partly substituted is introduced to cells, revealing that the Rho protein plays an important role in Ras-induced transformation, that is, tumorigenesis (G. C. Prendergast et al., Oncogene, 10, 2289–2296 (1995); Khosravi-Far, R. et al., Mol. Cell. Biol., 15, 6443–6453 (1995)*; R. Qiu et al., Proc. Natl. Acad. Sci. USA, 92, 11781–11785 (1995)*; Lebowitz, P. et al., Mol. Cell, Biol., 15, 6613–6622 (1995)*).

It has also been demonstrated that mutation of GDP/GTP-exchange proteins which act on the Rho protein results in cell transformation (Collard, J., Int. J. Oncol., 8, 131–138 (1996)*; Hart, M. et al., J. Biol. Chem., 269, 62–65 (1994); Horii, Y. et al., EMBO J., 13, 4776–4786 (1994)).

In addition, the Rho protein has been elucidated to be involved in cancer cell invasion, that is, metastasis (Yoshioka, K. et al., FEBS Lett., 372, 25–28 (1995)). The cancer cell invasion is closely associated with changes in cancer cell activity to form cell adhesion. In this context, the Rho protein is also known to be involved in the formation of cell adhesion (see above Morii, N. et al. (1992); Tominaga, T. et al. (1993); Nusrat, A. et al. (1995); Landanna C. et al. (1996)*).

On the other hand, a novel protein kinase having a molecular weight of approximately 120 kDa (hereinafter referred to as PKN or Protein Kinase N) has recently been isolated, and the whole amino acid sequence thereof has been determined. Furthermore, PKN has been proved to have a catalytic region highly homologous to that of Protein Kinase C and actually has serine/threonine kinase activity (Mukai, H. & Ono, Y. Biochem. Biophys. Res. Commun. 199, 897–904 (1994), Mukai, H. et al., Biochem. Biophys. Res. Commun. 204, 348–356 (1994), and Mukai, H. et al., Biochem. Biophys. Acta 1261, 296–300 (1995)). Substitution of Arg for Lys at position 644 of PKN leads to loss of the protein kinase activity (Mukai, H. et al., ibid.).

The protein kinase activity is activated by unsaturated fatty acids such as arachidonic acid (Mukai, H. et al., Biochem. Biophys. Res. Commun., 204, 348–356 (1994); and Kitagawa, M. et al., Biochem. J., 310, 657–664 (1994)). cDNAs of PKN of human beings, rat, and Xenopus have been cloned, and the amino acid sequences thereof have been determined (Mukai, H. & Ono, Y., Biochem. Biophys. Res. Commun., 199, 897–904 (1994); Mukai, H. et al., Biochim. Biophys. Acta., 1261, 296–300 (1995)). PKN from human is a protein of 942 amino acid residues, and the amino acid sequence of the carboxyl-terminal catalytic region is highly homologous to the amino acid sequence of the catalytic region of Protein Kinase C. Therefore, PKN is often called Protein Kinase C-related kinase 1 (Palmer, R. H. & Parker, P. J., FEBS Lett., 356, 5–8 (1994)).

The amino-terminal regulatory region of PKN contains some of leucine zipper sequences, and a polybasic region is located immediately at the amino terminal side of the leucine zipper sequence. Furthermore, it has been reported that, there are at least two isozymes concerning PKN (protein kinase C-associated kinases 2 and 3) (Palmer, R. H. & Parker, P. J., FEBS Lett. 356, 5–8 (1994)).

It is only recently (after the first filed application which provides the right of the priority of the present application) that a several proteins have been identified as candidates of Rho-targets in mammals different from PKN: citron (Madaule, P. et al., FEBS Lett., 377, 243–248 (1995)*), rhophilin (Watanabe, G. et al., Science, 271, 645–648 (1996)*), p160$^{ROCK}$ (Ishizaki, T. et al., EMBO J. 15, 1885–1893 (1996)*), Rho-associated kinase (Matsui, T. et al., EMBO J., 15, 1885–1893 (1996)*), ROKα(Leung, T. et al., J. Biol. Chem., 270, 29051–29054 (1995)*), rhotekin (Reid, T. et al., J. Biol. Chem., 271, 9816–9822 (1996)*), and myosin binding subunit(K. Kimura, et al., Science 273, 245–248 (1996)*). In addtion, Protein Kinase C1 (PKC1) (Nonaka, H. et al., EMBO J. 14, 5931–5938(1995)*) and 1,3-β-glucan synthase (Drgonova, J. et al., Science 272, 277–279(1996)*; Qadota, H. et al., Science 272, 279–281(1996*) have been identified as candidates of Rho-targets in yeasts (Saccharromyces cerevisiae).

Microtubules, actin filaments, and intermediate filaments may be mentioned as major fibrous components constituting cytoskeleton. It is known that the cytoskeleton is controlled by the phosphorylation of these fibrous components (N. Inagaki et al., Trend. Biochem. Sci., 19, 448–452 (1994)). Furthermore, regarding the intermediate filament, the structure has been elucidated on amino acid sequence level (Julien, J. et al., Biochim. Biophys. Acta 909, 10–20 (1987) (human neurofilament-L), Myers, M. et al., EMBO J., 6, 1617–1626 (1987) (human neurofilament-M), Lees, J., et al., EMBO J., 7, 1947–1955 (1988) (human neurofilament-H), and Honore, B., et al., Nucl. Acid. Res., 18, 6692 (1990) (human vimentin)). However, insofar as the present inventors know, the interaction between the intermediate filament and PKN has not been reported.

Furthermore, a wide variety of isoforms of cytoskeletal protein α-actinin, including skeletal muscle-, smooth muscle-, and non-muscle-types of α-actinins derived from various cells and tissues, has been characterized. In human, only clones of skeletal muscle-type of α-actinin (HuActSkl, designated in Beggs, A., et al., J. Biol. Chem. 267, 9281–9288 (1992)) and non-muscle-type of α-actinin (HuActNm, designated in Beggs, A., et al., J. Biol. Chem. 267, 9281–9288 (1992)) highly homologous to HuActSkl (89% similarity and 80% identity) have been isolated (Millake, D. B., et al., Nucleic Acids Res. 17, 6725 (1989); and Youssoufian, H., et al., Am. J. Hum. Genet. 47, 62–71 (1990)). The functional difference among these α-actinins is that binding of the muscle isoform to F-actin is inhibited by $Ca^{2+}$, whereas binding of the non-muscle isoform is insensitive to $Ca^{2+}$ (Burridge, K. & Feramiscoo, J. R. Nature 294, 565–567 (1981); Bennett, J. P., et al., Biochemistry 23, 5081–5086 (1984); Duhaiman, A. S. & Bamburg, J. R. Biochemistry 23, 1600–1608 (1984); and Landon, F., et al., Eur. J. Biochem. 153, 231–237 (1985)).

α-Actinin is a member of spectrin superfamily, including spectrin and dystrophin (Blanchard, A., et al., J. Muscle Res. Cell Motil. 10, 280–289 (1989); Dubreuil, R. R. Bioessays 13, 219–226 (1991); and Bennett, V, Physiol. Rev. 70, 1029–1065 (1990)). Family members are characterized by the N-terminal actin-binding domain, central rod-shaped spectrin-like repeats, and the C-terminal EF-hand-like domain. α-Spectrin contains 21 rod-shaped repeats in the N-terminal instead of the EF-hand-like domain. The C-terminus of α-spectrin is clearly identical to α-actinin, and especially the repeat 20 of α-spectrin is highly homologous to the repeat 3 of α-actinin (Wasenius, V. M., et al., J. Cell Biol. 108, 79–93 (1989); and Hong, W. J. & Doyle, D. J. Biol. Chem. 264, 12758–12764 (1989)). The positions of the repeat in these proteins are substantially identical to each other.

α-Actinin is composed of three domains: an N-terminal actin-binding domain, an extended rod-shaped domain with four internal 122 amino acid repeats (spectrin-like repeats), and a C-terminal region containing a pair of presumptive helix-loop-helix $Ca^{2+}$-binding motifs (often referred to as EF-hands ((Blanchard, A., et al., J. Muscle Res. Cell Motil, 10, 280–289 (1989)).

However, the interaction between α-actinin and PKN has not been reported insofar as the present inventors know.

Furthermore, many data recently indicate some signal transduction pathways induced by growth factors overlaps one induced by stress. Rac and Cdc42, other members of the Rho family small GTPases, are activated by not only growth factors but also stresses such as proinflammatory cytokines and ultraviolet radiation, and are involved in the activation of stress activated-MAP kinases (Minden, A. Cell 81, 1147–1157 (1995); Coso, 0. et al., Cell 81, 1137–1146 (1995); and Zhang, S. et al., J. Biol. Chem. 270, 23934–23936 (1995)). Recently, it has been reported that lysophosphatidic acid (LPA), serum, and stresses (for example, arsenite and osmotic shock) regulate c-fos transcription through the activation of serum response element (SRE) by serum response factor (SRF) and that functional Rho is necessary in this case (Hill, C. S. et al., Cell 81. 1159–1170 (1995)). SRE activation, however, is not mediated by other Rho family proteins such as Rac and Cdc42 (Hill, C. S. et al., Cell 81. 1159–1170 (1995)). The above finding suggests the presence of an unknown pathway, responsible for signal transduction to the cell nucleus, downstream of the Rho protein (Vojtek, A. & Cooper, J., Cell 82, 527–529 (1995)).

It should be noted that an asterisk hereinafter indicates a publication issued after the first filed application which provides the right of the priority of the present application.

SUMMARY OF THE INVENTION

The present inventors have now found that the activated RhoA protein binds to an amino-terminal region of PKN and that the protein kinase activity of PKN is activated in the activated Rho protein-dependent manner. Furthermore, they have found that a particular region of the amino terminal of PKN has an activity to inhibit binding between PKN and the activated Rho protein.

The present inventors have also found that PKN binds to and/or phosphorylates cytoskeletal proteins (intermediate filaments and α-actinin) which control the cell morphology. Specifically, they have found that neurofilament (hereinafter often referred to as NF) L, which is one of the subunits of the neuron-specific intermediate filament, binds to PKN, that the N-terminal regulatory region of PKN binds to head-rod domains of NFL as well as other intermediate filament proteins (other subunits (M and H) of NF and vimentin) or spectrin-like repeats of α-actinin and EF-motif hands, that the purified rat PKN phosphorylates native NF from bovine spinal cord and the head-rod domain of bacterially synthesized intermediate filament proteins (each subunit of NF and vimentin), and that phosphorylation of NFL by PKN inhibits the polymerization of NFL in vitro.

The present inventors have also found that the amino-terminal region of PKN binds to the carboxyl-terminal region of PKN and that a particular region of the amino terminal of PKN acts as a pseudosubstrate for the protein kinase of PKN (i.e., to inhibit the protein kinase activity of PKN).

In addtion, the present inventors have found that PKN is reversibly translocated from cytoplasm into the nucleus by exposing cells to stresses such as heat shock, sodium arsenite and serum starvation.

The present inventions are based on these findings.

Accordingly, an object of the present invention is to provide a peptide comprising a modified amino acid sequence of Protein Kinase N having activated Rho protein binding activity and not having protein kinase activity, and a peptide inhibiting binding between PKN and the Rho protein.

Another object of the present invention is to provide a peptide having cytoskeletal protein (intermediate filament and/or α-actinin) binding activity, a peptide having activity to bind to the protein kinase catalytic region of PKN, a peptide inhibiting the protein kinase activity of PKN, and a peptide inhibiting the translocation of PKN from cytoplasm to nucleus, and a peptide eligible for phosphorylation by PKN.

A further object of the present invention is to provide a base sequence encoding the peptide, a vector comprising the base sequence, a host cell transformed with the vector, a process for producing the peptide or protein, a tumorigenesis or metastasis suppressing agent comprising the protein, and a method for screening a material inhibiting binding between the activated Rho protein and PKN.

In addition, the present inventors have confirmed that the proteins according to the present invention are different from the other Rho protein binding proteins (citron, rhophilin, p160$^{ROCK}$, Rho-binding kinase, ROKα, rhotekin, myosin-binding subunit, Protein Kinase C1 (PKC1), and 1,3-β-glucan synthase). It should be noted that all the Rho protein binding proteins were identified after the first filed application which provides the right of priority of the present application.

Lane 1: 0.2 M NaCl-eluate from the GST-RhoA affinity column, lane 2: 75 mM NaCl-eluate from the DEAE Sepharose column.

FIG. 2 is an electrophoretic photograph showing the result of immunoblot analysis of p128 using an anti-PKN antibody.

Lane 1: preimmune serum, lane 2: anti-PKN antibody.

Figure 3:
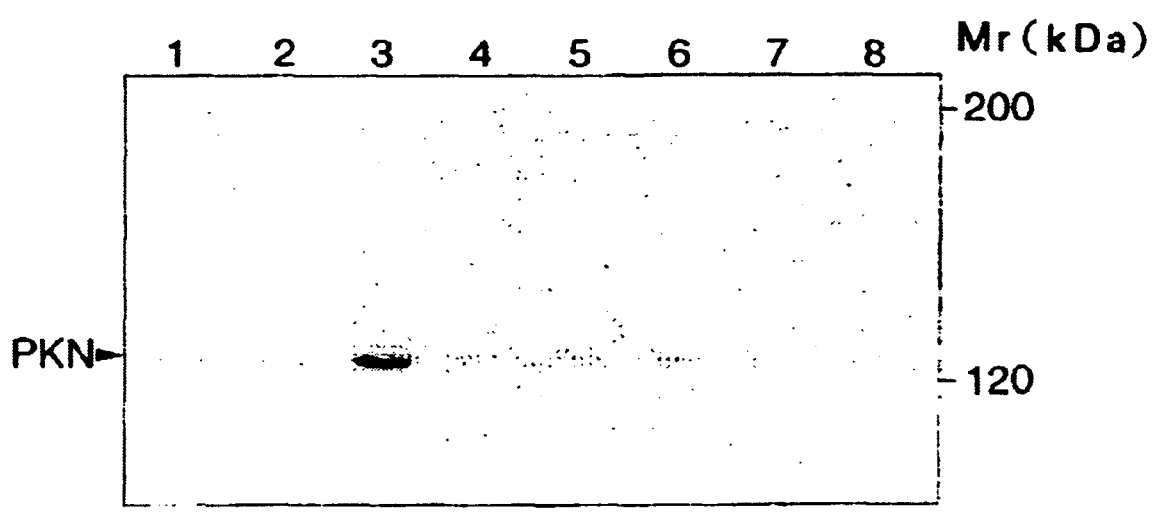

FIG. 3 is an electrophoretic photograph illustrating the autophosphorylation of PKN.

Lane 1: GST, lane 2: GDP*GST-RhoA, lane 3: GTPγS.GST-RhoA, lane 4: GTPγS.GST-RhoA$^{Asp38}$, lane 5: GDP.GST-Rac, lane 6: GTPγS.GST-Rac, lane 7: GDP.GST-H-Ras, lane 8: GTPγS.GST-H-Ras.

FIG. 4 illustrates the dose-dependent activation of PKN kinase activity by the RhoA protein on an αPKC peptide.

Figure 5:
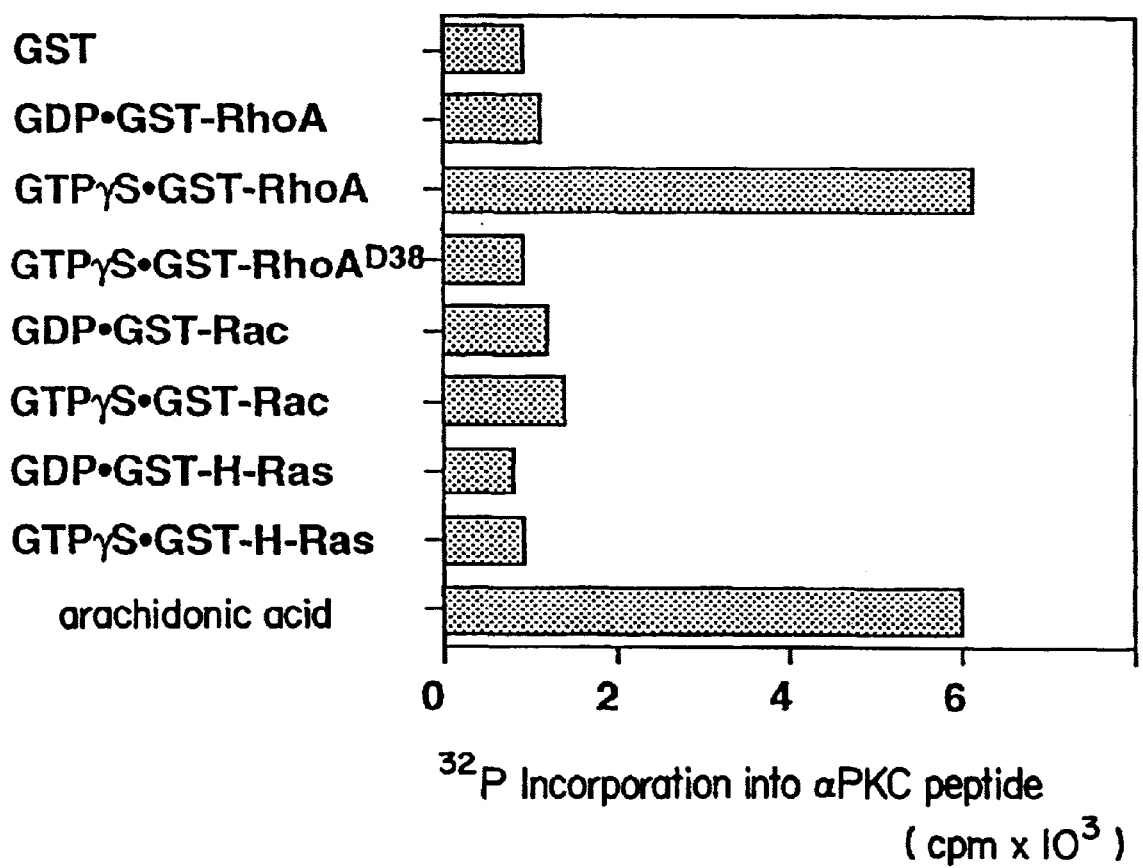

FIG. 5 illustrates the effects of various small G proteins on the kinase activity of PKN.

Figure 6:
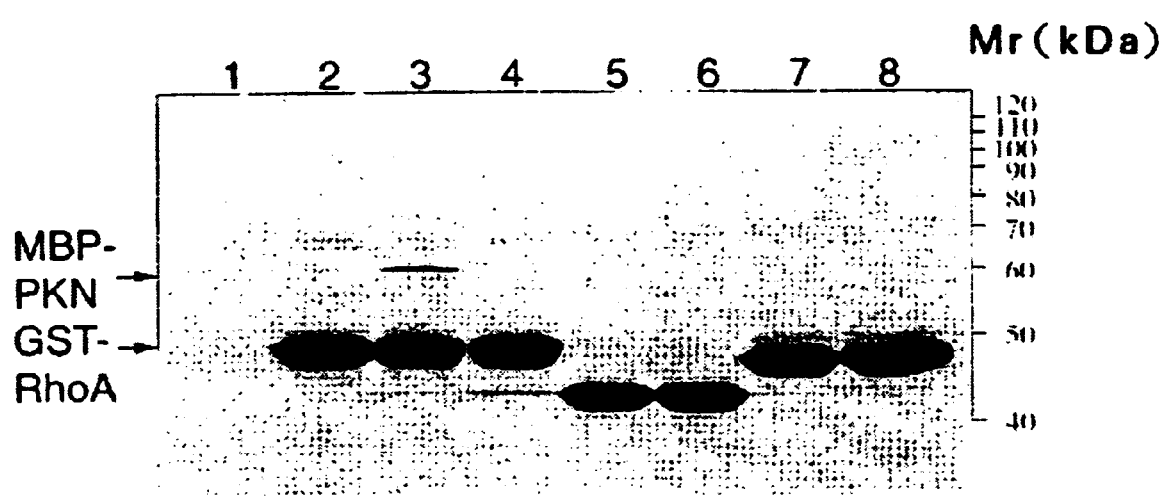

FIG. 6 is an electrophoretic photograph showing the complex formation between recombinant PKN and GTPγS.GST-RhoA in a cell-free system.

Lane 1: GST, lane 2: GDP.GST-RhoA, lane 3: GTPγS.GST-RhoA, lane 4: GTPγS.GST-RhoA$^{Asp38}$, lane 5: GDP.GST-Rac, lane 6: GTPγS.GST-Rac, lane 7: GDP.GST-H-Ras, lane 8: GTPγS.GST-H-Ras.

Figure 7:
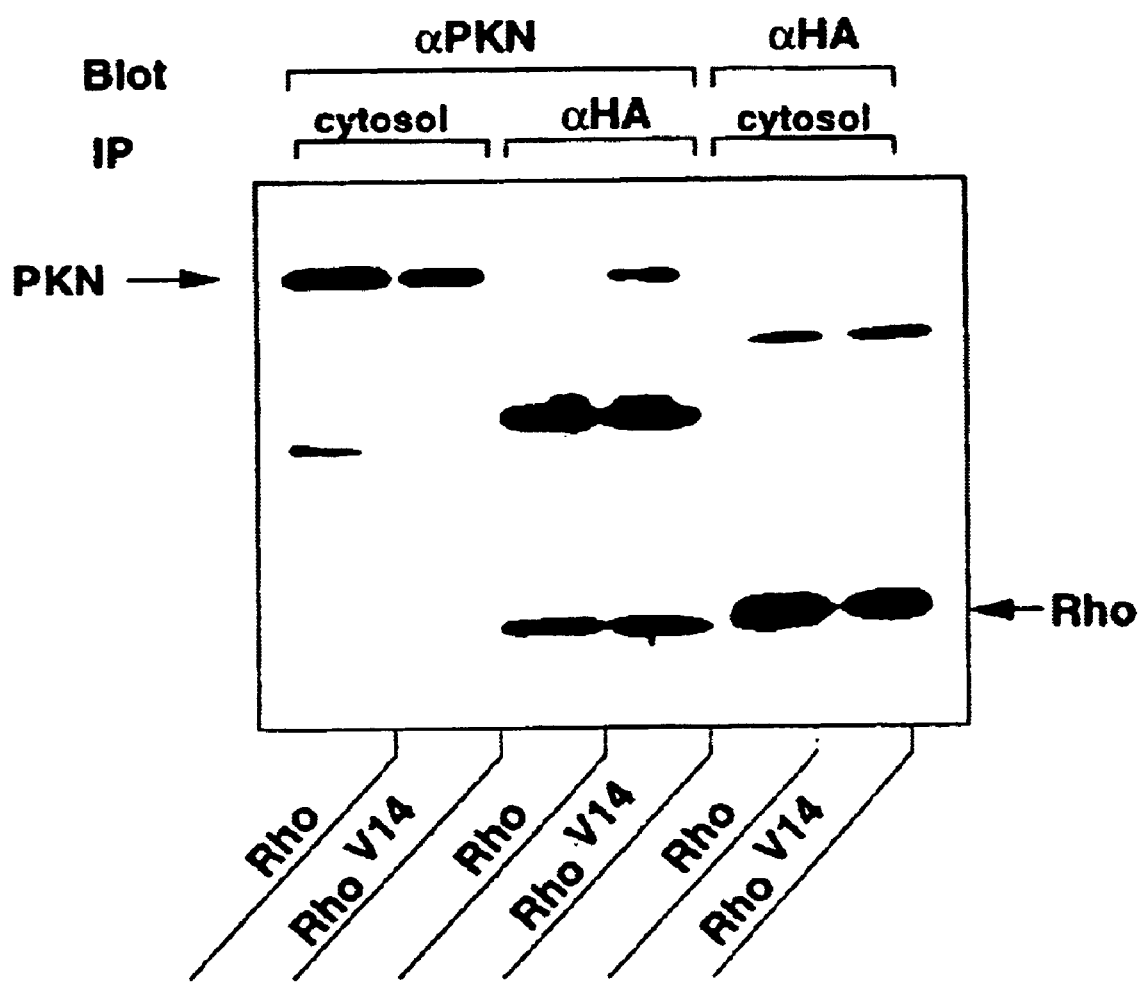

FIG. 7 is an electrophoretic photograph showing the complex formation between PKN and the RhoA protein in COS7 cells.

Figure 8:
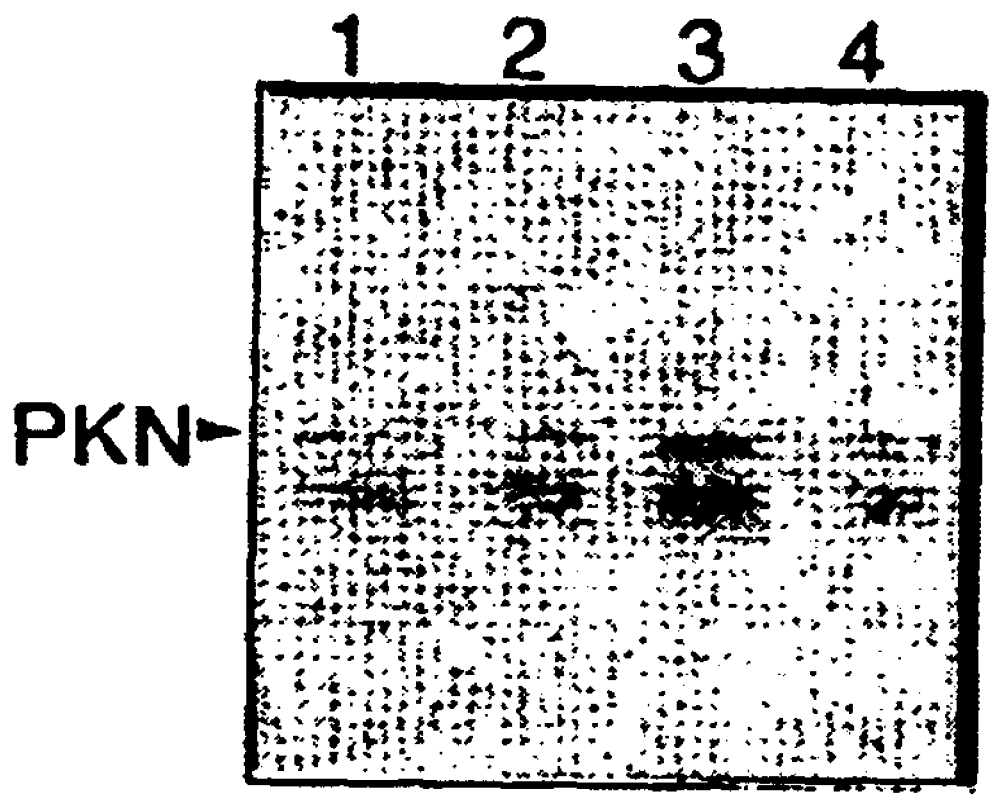

FIG. 8 is an electrophoretic photograph showing the stimulation of PKN autophosphorylation by LPA.

Lane 1: none, lane 2: C3, lane 3: LPA, lane 4: C3+LPA.

FIG. 9 is a photograph showing the binding between PKN and the RhoA protein in a two-hybrid system (a photograph of biological morphology).

Figure 10:
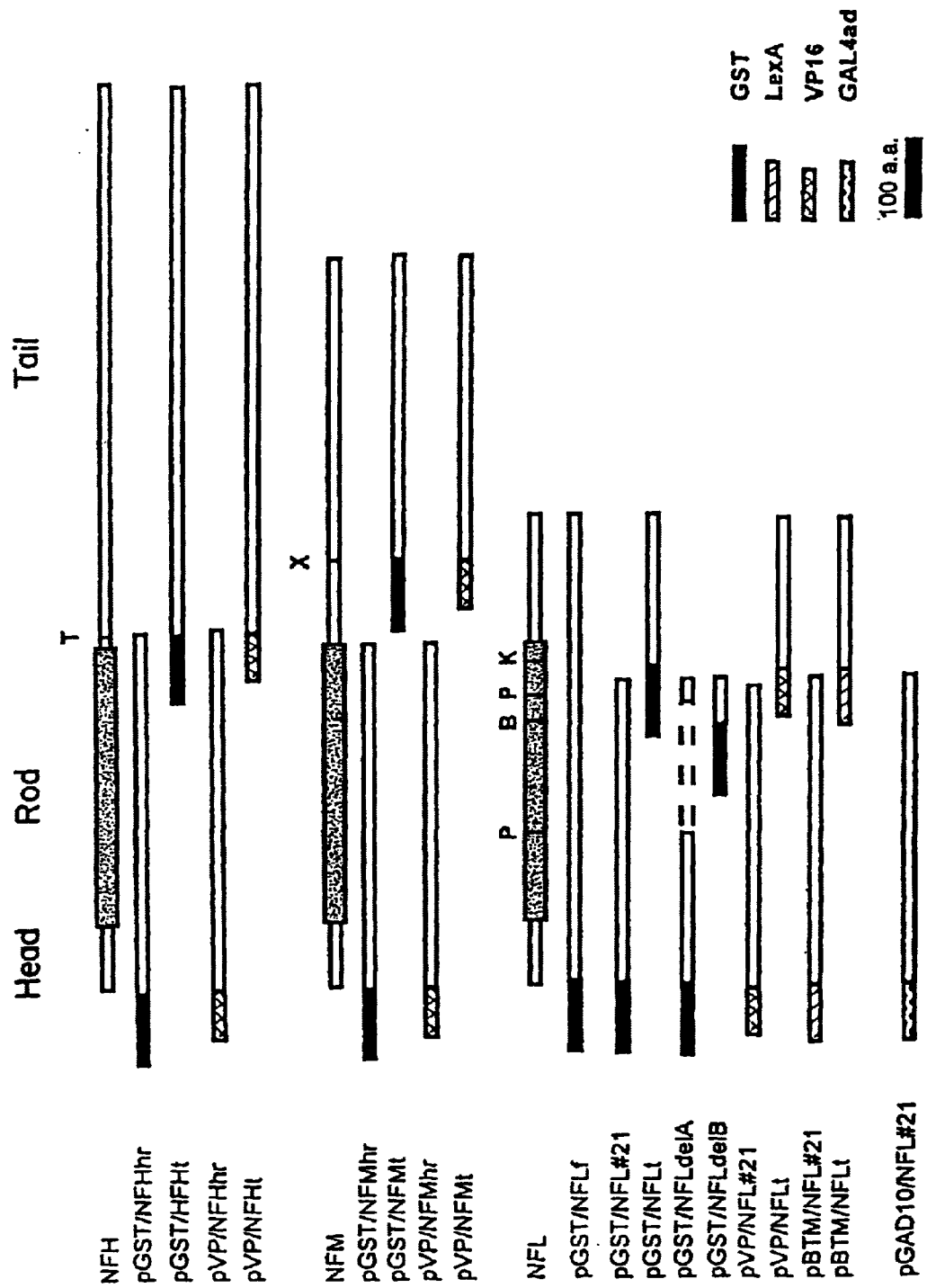

FIG. 10 is a schematic diagram showing the structure of a fusion construct for each subunit of NF.

Full sequence of each subunit of NF is represented by a dark box. Thick boxes indicate the location of the rod domain of each subunit of NF. The VP16 transactivation domains (cross-hatched boxes), or LexA DNA binding domains (hatched boxes), or glutathione S transferase (solid boxes) were fused to the various deletion mutant of NF (open boxes). pGAD10-NFL#21 isolated from this library was shown at the bottom of the figure. The dashed box indicates deleted sequence. T,Tth111I; X, XhoI; P, PstI; B, BglII; and K, KpnI.

FIGS. 11A and 11B are photographs showing the association between PKN and NF in a two-hybrid system (a photograph of biological morphology).

(A) The VP16 transcription activation domain plasmid (pVP16; lines 7 and 10) or fusion plasmids coding for the head-rod domain of NFL (pVP-NFL#21; lines 1–3), tail domain of NFL (pVP-NFLt; lines 4–6), PKNN1 (pVP-PKNN1; lines 8 and 11), and PKNC1 (pVP-PKNC1; lines 9 and 12) were transformed into yeast with the DNA-binding domain plasmid (pBTM116; lines 1 and 4), or fusion plasmid coding for the head-rod domain of NFL (pBTM-NFL#21; lines 7–9), tail domain of NFL (pBTM-NFLt; lines 10–12), PKNN1 (pBTM-PKNN1; lines 2 and 5), and PKNN1 (pBTM-PKNC1; line 3 and 6).

(B) The VP16 transcription activation fusion plasmids coding for the head-rod domain of NFL (pVP-NFL#21; line 1), NFM (pVP-NFMhr; line 2), and NFH (pVP-NFHhr; line 3) and the tail domain of NFL (pVP-NFLt; line 4), NFM (pVP-NFMt; line 5), and NFH (pVP-NFHt; line 6) were transformed into yeast with the DNA-binding domain fusion plasmids coding for PKNN1 (pBTM-PKNN1; lines 1–6).

For each transformation, five independent colonies were picked from nonselected (His+) plates, patched on an agar plate, and grown for 3 weeks before they were tested for production of β-galactosidase. The data are representative of three independent transformations.

FIG. 12 is an electrophoretic photograph showing the association of PKN with NF in vitro.

The N-terminal region (PKNN2) or C-terminal region (PKNC2) of $^{35}$S-labeled PKN prepared by in vitro translation was incubated with bacterially synthesized GST (lanes 4, 6, 10 and 12) or various deletion fragments of GST-NFL (GST-NFL#21, lanes 1, 5, 7, and 11; GST-NFLdelA, lanes 2 and 8; GST-NFLdelB, lanes 3 and 9). Proteins were collected with Glutathione-Sepharose beads (G-beads) and analyzed by using SDS-PAGE and autoradiography as described in Example 7. In the drawing, Input represents 10 μl of the binding reaction mixture before the G-Beads treatment, and G-Beads represents the precipitate after the G-Beads treatment. The drawing shows typical results from three independent experiments.

FIG. 13 is an electrophoretic photograph showing the association of PKN with NF in vitro.

$^{35}$S-labeled PKNN2 prepared by in vitro translation was incubated with bacterially synthesized GST (lanes 4 and 8) or the GST fused head-rod domain of NFL (GST-NFL#21, lanes 1 and 5), NFM (GST-NFMhr, lanes 2 and 6), and NFH (GST-NFHhr, lanes 3 and 7). Glutathione-Sepharose beads (G-Beads) were added, and samples were processed as in FIG. 12.

In the drawing, Input represents 10 µl of the binding reaction mixture before the G-Beads treatment, and +G-Beads represents the precipitate after the G-Beads treatment. The positions of labeled protein are indicated by arrowhead. The positions of markers for the molecular weight of proteins are shown on the left side of the drawing. The drawing shows typical results from three independent experiments.

FIG. 14 is an electrophoretic photograph illustrating the phosphorylation of NF by PKN.

a and b show protein silver staining and autoradiograph of SDS-PAGE of the purified bovine NFs incubated with purified rat PKN for 5 min at 30° C. in the presence (lane 2) or absence (lane 1) of 40 µM arachidonic acid. NFH, NFM, and NFL are indicated on the left side of lane 2 by H, M, and L, respectively.

FIG. 15 is an electrophoretic photograph illustrating the phosphorylation of NF by PKN.

It shows the time course of phosphorylation of purified bovine NF containing triplet proteins (complex of NFL, NFM, and NFH) by PKN. Autoradiograph of SDS-PAGE of the dephosphorylated form (lanes 1–5) and phosphorylated form (lanes 6–10) of NFs incubated with rat purified PKN and 40 M arachidonic acid for 0 min (lanes 1 and 6), 10 min (lanes 2 and 7), 30 min (lanes 3 and 8), 60 min (lanes 4 and 9), and 120 min (lanes 5 and 10) at 30° C. NFL, NFM, and NFH are indicated on the right side of lanes 5 and 10 by L, M, and H, respectively. The position of autophosphorylation of PKN is indicated by white arrowhead. The positions of molecular size markers are marked at left.

FIG. 16 illustrates the phosphorylation of NF by PKN.

Figure 17:
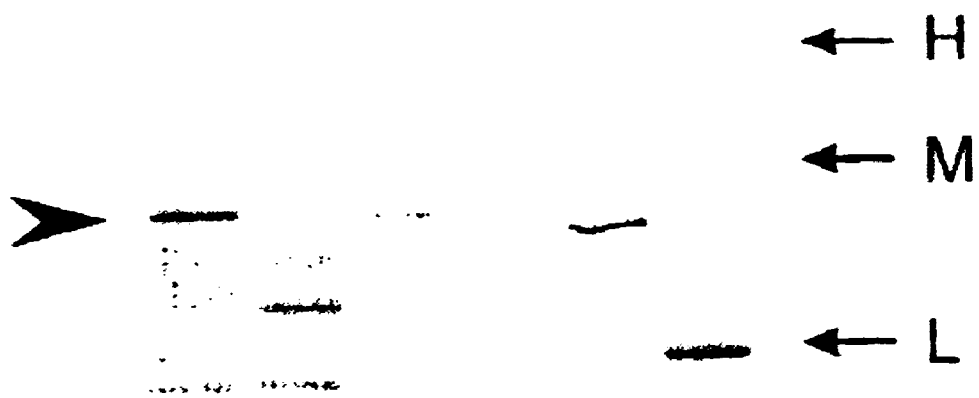
Figure 17:

It shows the amount of radiolabel incorporated into each NF protein. Open circles, NFL pretreated with alkaline phosphatase (indicated by dL); closed circles, NFL untreated with alkaline phosphatase (indicated by L); open triangles, NFH pretreated with alkaline phosphatase (indicated by dH); closed triangles, NFH untreated with alkaline phosphatase (indicated by H); open squares, NFM pretreated with alkaline phosphatase (indicated by dM); closed squares, NFM untreated with alkaline phosphatase (indicated by M). The data are representative of three independent experiments. FIG. 17 is an electrophoretic photograph illustrating the identification of phosphorylation of the head-rod domain of each subunit of NF.

(A) and (B) respectively show protein staining and autoradiograph of SDS-PAGE of GST fused NF proteins phosphorylated by PKN. The head-rod domain of GST-NFL (GST-NFL#21; lane 1), GST-NFM (GST-NFMhr; lane 3), and GST-NFH (GST-NFHhr; lane 5), and the tail domain of GST-NFL (GST-NFLt; lane 2), GST-NFM (GST-NFMt; lane 4), and GST-NFH (GST-NFHt; lane 6) were incubated with rat purified PKN and 40 µM arachidonic acid for 10 min at 30° C. as described in Example 9. The positions of the GST-NFL, NFM, and NFH are indicated on the right side of lane 6 in (A) by L, M, and H, respectively. The position of autophosphorylation of PKN is indicated by white arrowhead in (B). The position of the head-rod domain of GST-NF subunit is indicated by black arrowhead.

Figure 18:
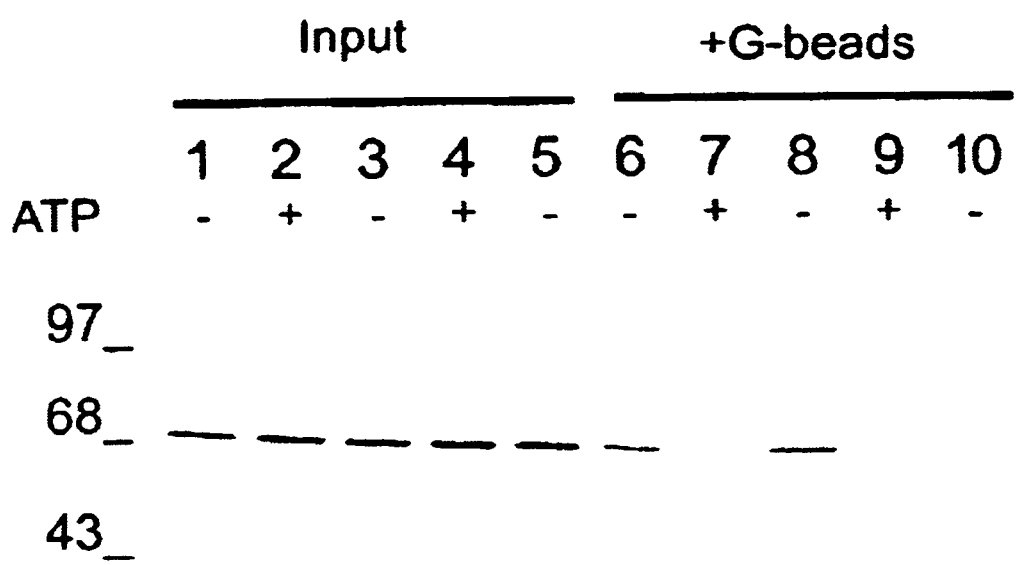

FIG. 18 is an electrophoretic photograph showing the effects of phosphorylation on the polymerization of NFL.

$^{35}$S-labeled NFL, prepared by in vitro translation, and rat PKN purified were incubated with bacterially synthesized GST (lanes 5 and 10), the head-rod domain of GST-NFL (GST-NFL#21; lanes 1, 2, 6, and 7), or GST-full length NFL (GST-NFLf; lanes 3, 4, 8, and 9) in the presence (lanes 2, 4, 7, and 9) or absence (lanes 1, 3, 5, 6, 8, and 10) of 100 µM ATP. GST or GST fusion proteins were collected with glutathione-Sepharose (G-Beads) and analyzed by SDS-PAGE, followed by autoradiography as described in Example 10. Input represents the reaction mixture before the G-Beads treatment, and +G-Beads represents the precipitate after the G-Beads treatment. The drawing shows typical results from three independent experiments.

Figures 19, 20:
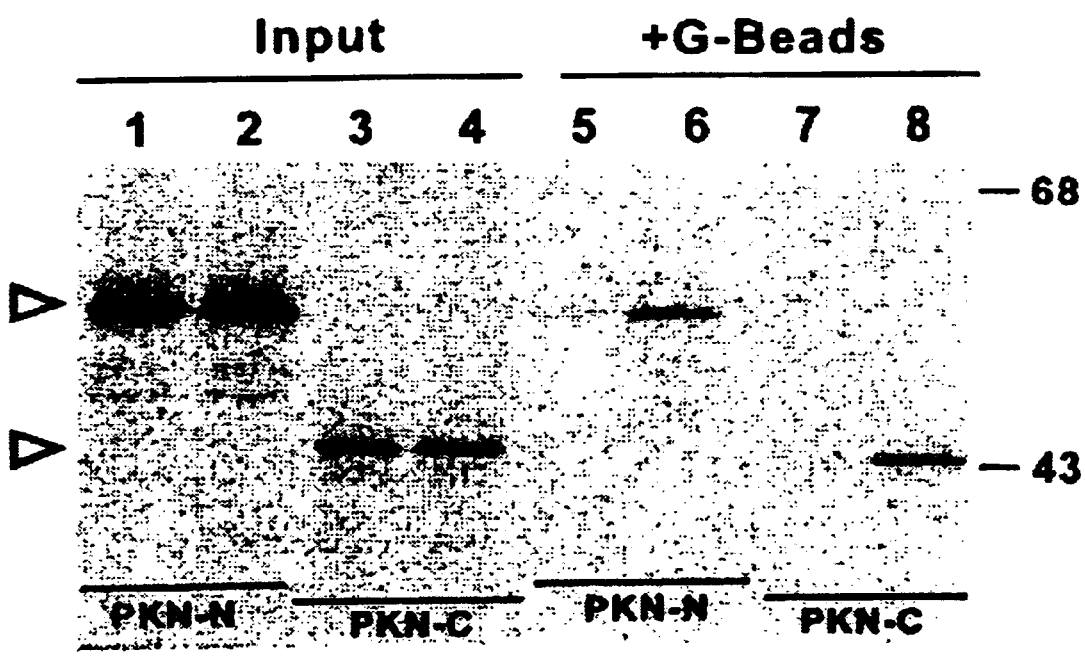

FIG. 19 is a photograph showing the binding of the amino-terminal region of PKN to the carboxyl-terminal region in a two-hybrid system (a photograph of biological morphology).

FIG. 20 is an electrophoretic photograph showing the binding of portions of PKN in vitro.

$^{35}$S-labeled in vitro translated amino-terminal region (lanes 1, 2, 5, and 6) or carboxyl-terminal region (lanes 3, 4, 7, and 8) were incubated with bacterially synthesized GST (lane 1, 3, 5, and 7) or GST fused to the amino-terminal region of PKN (lanes 4 and 8) or GST fused to the carboxyl-terminal region of PKN (lanes 2 and 6). Proteins were collected with glutathione-Sepharose beads (G-beads) and analyzed by SDS-PAGE, followed by autoradiography as described in Example 2.

Input shows 10 µl of the initial binding reaction mixture that was removed before precipitation. The positions of labeled protein are indicated by an arrow-head. Input represents the reaction mixture before the treatment with G-Beads. +G-Beads represents the precipitate after the G-Beads treatment. The positions of protein markers are shown at the right (kDa). The drawing shows typical results from three independent experiments.

Figure 21:
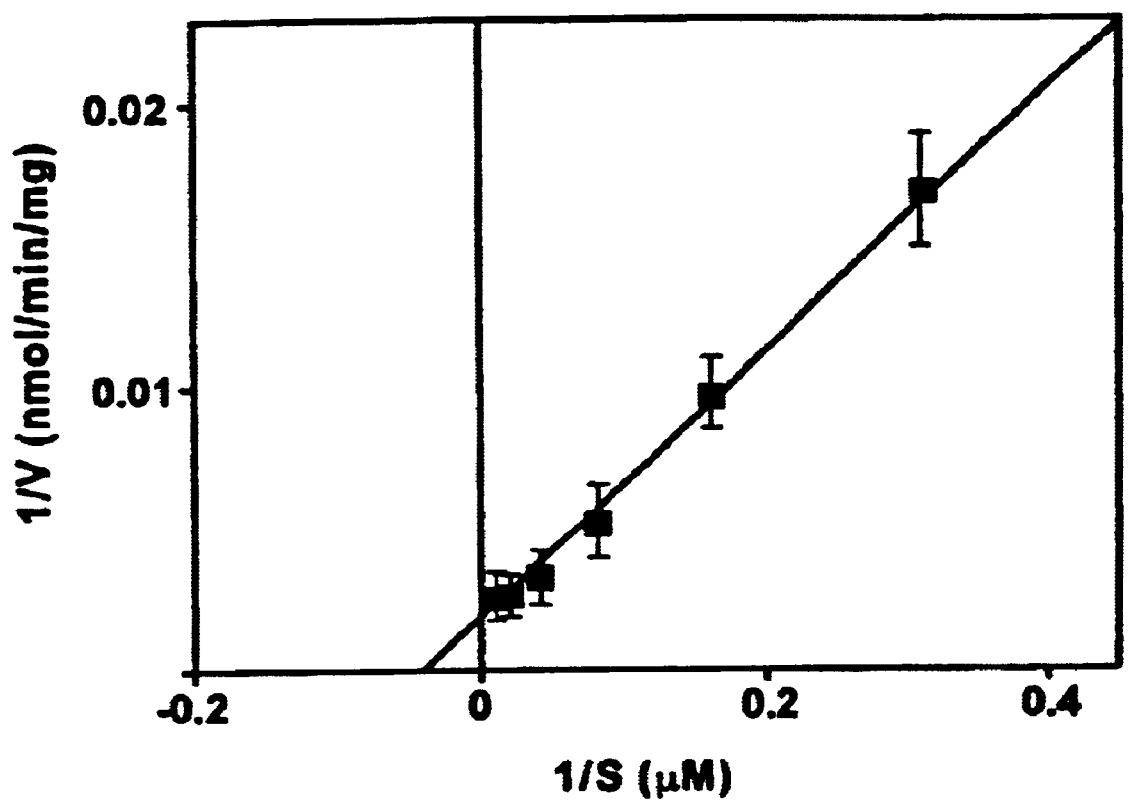

FIG. 21 illustrates the phosphorylation of [Ser$^{46}$] PKN (39–53) by PKN.

The [Ser$^{46}$] PKN (39–53) peptide was phosphorylated by the purified PKN as described in Example 13. A double-reciprocal plot of the data is shown. The results are means±S.E. from independent experiments performed in duplicate.

FIG. 22 illustrates the inhibition of the protein kinase activity of PKN with synthetic peptides.

Phosphorylated peptide substrates were used at corresponding Km concentrations (10 µM for δPKC peptide, 16 µM for Kemptide) in the presence of various concentrations of PKN (39–53) of peptide or PKN (54–73). PKN was measured by using PKN (39–53) peptide (closed circles) or PKN (54–73) peptide (open circles) as the inhibitor with δPKC peptide as the substrate. PKA was measured by using Kemptide as the substrate with PKN (39–53) peptide as the inhibitor (open squares). The protein kinase activity was determined as described in Examples 13 and 14. The results are means±S.E. from independent experiments performed in duplicate.

Figure 23:
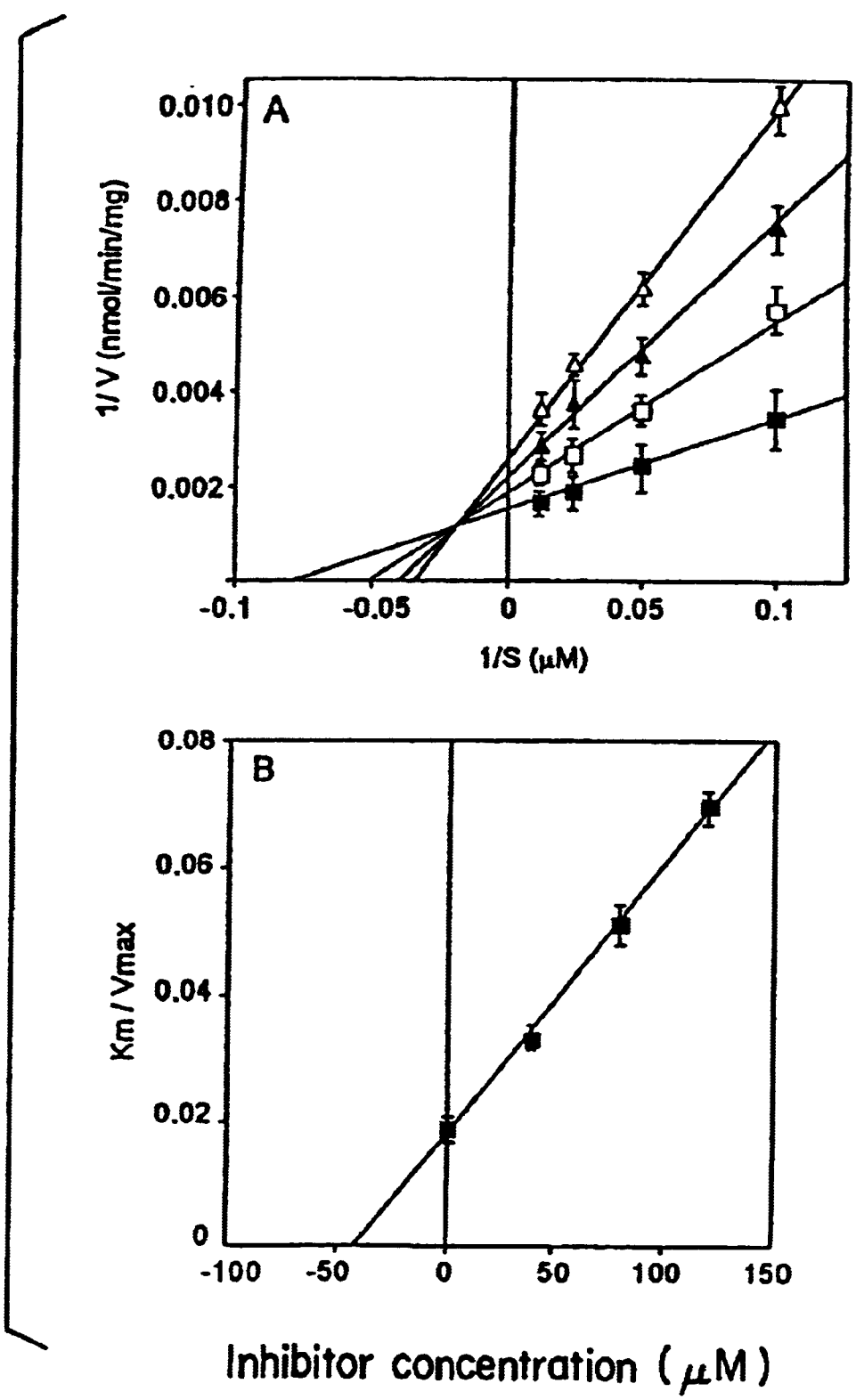

FIGS. 23A and 23B illustrate effects of PKN (39–53) peptide on the protein kinase activity of PKN.

(A) Double-reciprocal plots at varying PKN (39–53) concentrations. The PKN (39–53) concentrations were 0 (closed squares), 40 (open squares), 80 (closed triangles), and 120 (open triangles) µM, respectively. The δPKC peptide concentrations were 10, 20, 40, and 80 µM, respectively. The protein kinase activity was determined as described in Examples 13 and 14.

(B) Secondary plot of apparent Km/Vmax versus inhibitor. The results are means±S.E. from independent experiments performed in duplicate.

Figure 24:
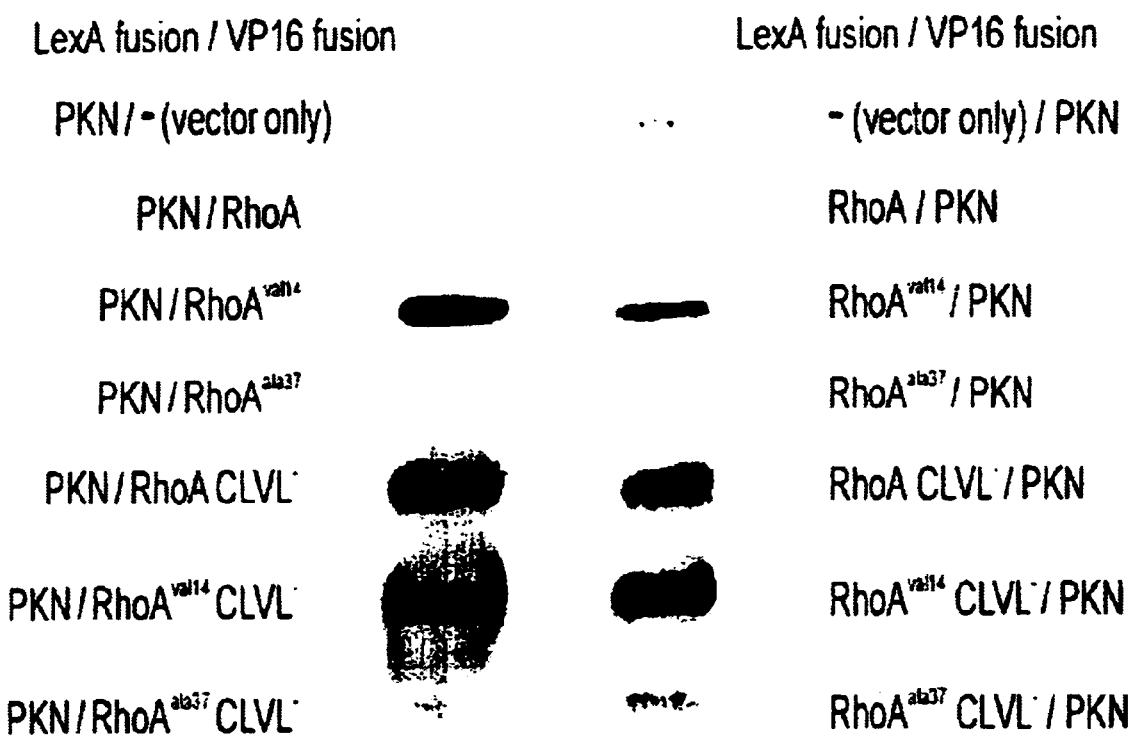

FIG. 24 is a photograph showing the binding between PKN and the Rho protein in a yeast two-hybrid system (a photograph of biological morphology). PKN indicates the N-terminal regulatory region of PKN. "CLVL⁻" indicates the deletion mutant of the RhoA protein which lacks the C-terminal lipid modification site. The drawing shows typical results from three independent experiments.

Figure 25:
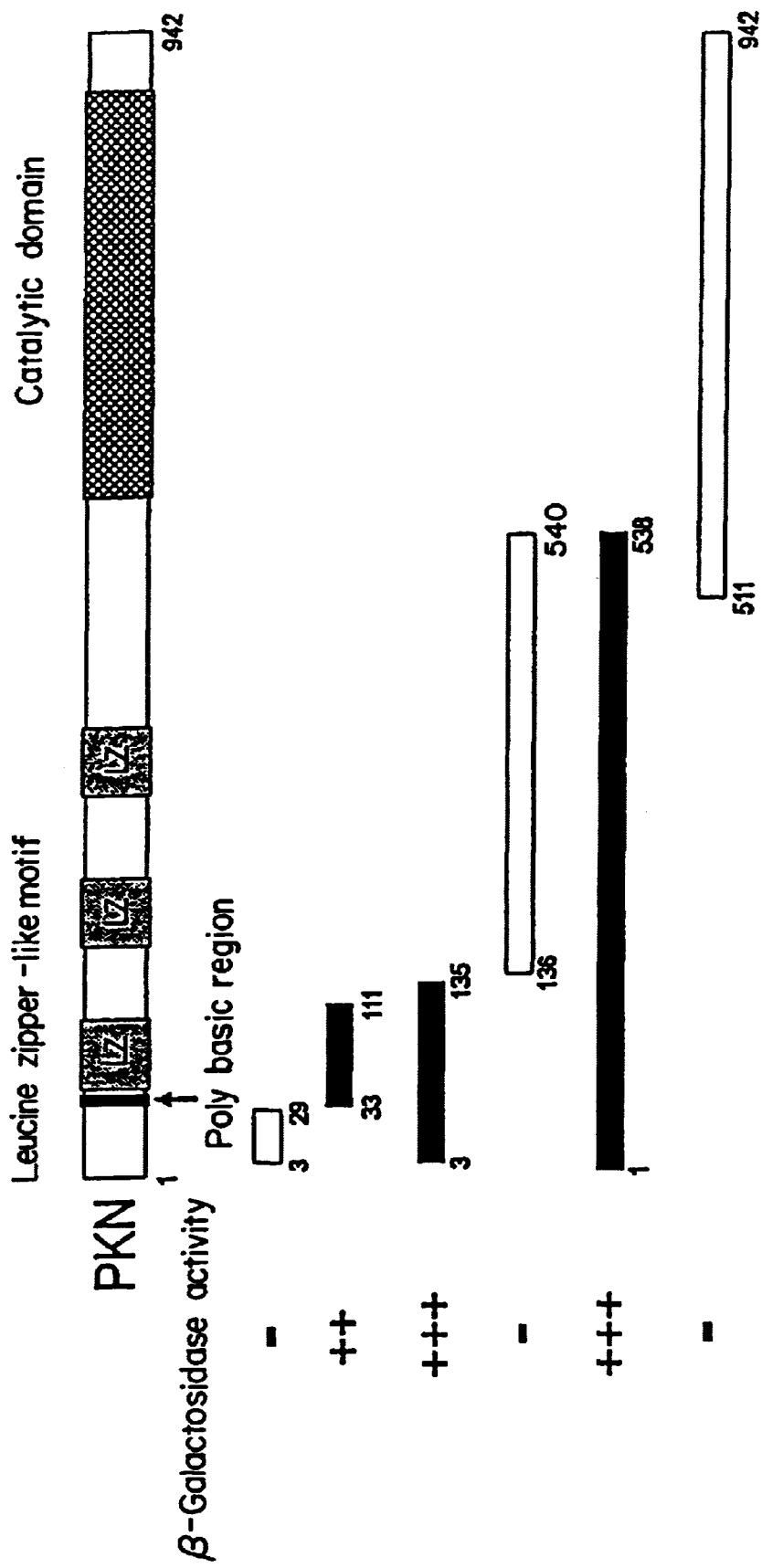

FIG. 25 illustrates the binding between PKN and the Rho protein in a yeast two-hybrid system. The degree of binding is expressed in terms of β-galactosidase activity. Schematic whole structure of PKN is represented at the top of the figure, and the deletion mutants are aligned below. "LZ" indicates leucine zipper-like motif. "+++" and "++" indicate development of strong color within 20 and 60 min from the initiation of the assay, respectively. "−" indicates no development of color within 24 hr.

FIG. 26 is an electrophoretic photograph showing the binding of the Rho protein to the N-terminal regulatory region of PKN. The results are representative of three independent experiments. "Input" shows the reaction mixture before the G-Beads treatment. "+G-Beads" represents the precipitate after the G-Beads treatment.

FIG. 27 is an electrophoretic photograph showing the inhibitory activity of partial peptide of PKN against binding between the Rho protein and N-terminal region of PKN. GTPγS.GST-RhoA was incubated with in vitro translated PKN in the presence of partial peptides of PKN at varying concentrations indicated in the drawing. The results are representative of three independent experiments.

Figure 28:
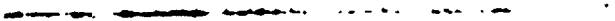

FIG. 28 is an electrophoretic photograph showing the inhibitory activity of partial peptide of PKN against binding between the Rho protein and N-terminal region of PKN. GTPγS.GST-RhoA was incubated with in vitro translated PKN in the presence of partial peptides of PKN at varying concentrations indicated in the photograph. The results are representative of three independent experiments.

FIG. 29 illustrates the effects of the N-terminal region of PKN on the endogenous GTPase activity of the RhoA protein. [γ-$^{32}$P]GTP.GST-RhoA (closed circle, open circle, mark X) or GST-RhoA$^{Val14}$ (open triangles) incubated in the presence (closed circle) or absence (open circles) of GST-PKN or with GST (mark X) for an indicated period of time and the bound radioactivity was determined by a filter binding assay. The remaining [γ-$^{32}$p] GTP bound to each protein was expressed as the percent of that measured at 0 min of incubation. The results are representative of three independent experiments.

Figure 30:
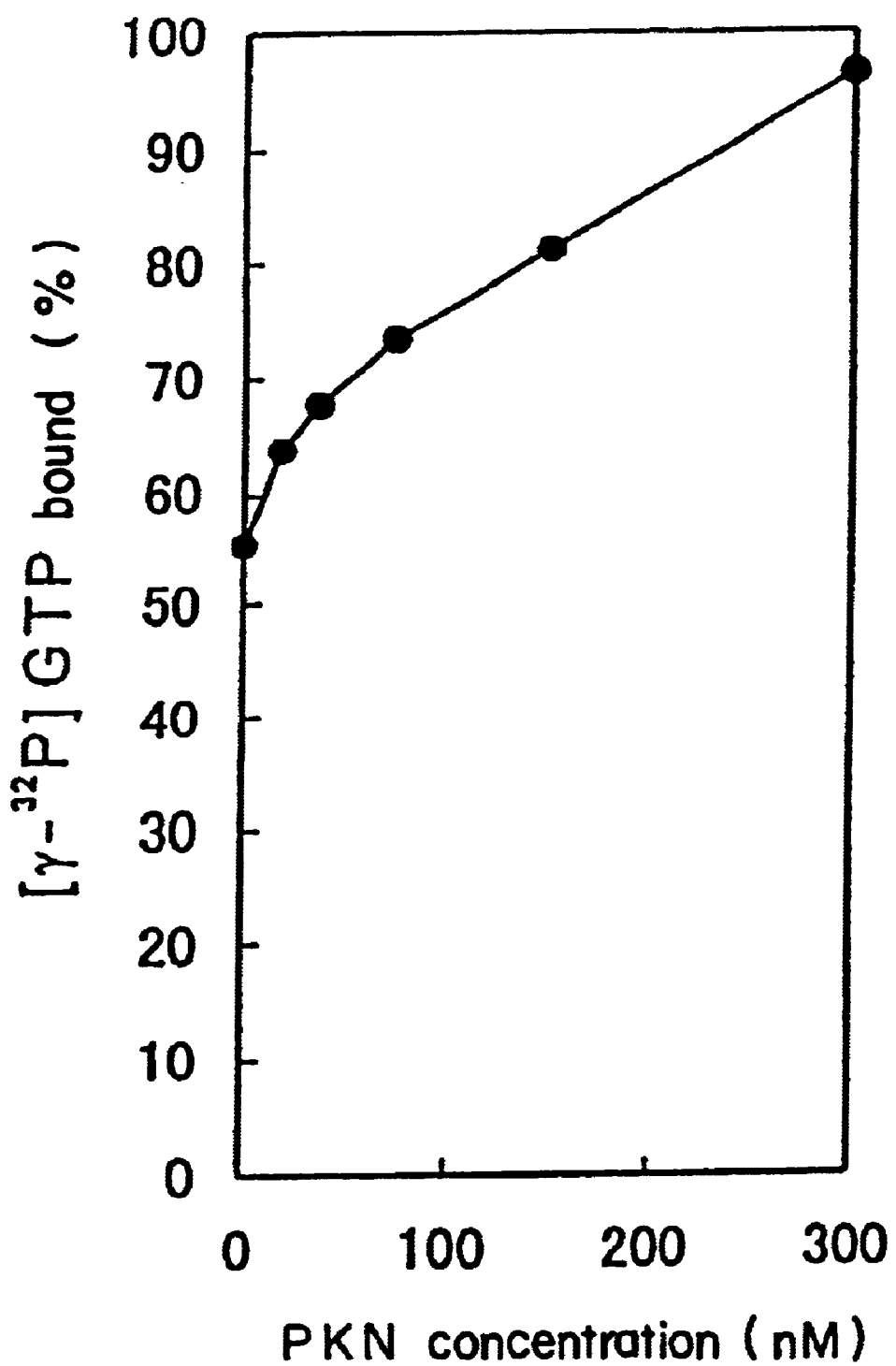

FIG. 30 is a diagram showing the influence of the N-terminal region of PKN on the GTPase activity of the RhoA protein. It shows the dose-dependent effect of PKN on GTPase. [γ-$^{32}$p] GTP.GST-RhoA was incubated with varied concentrations of the N-terminal region of PKN fused to GST for 10 min. The results are representative of three independent experiments.

Figure 31:
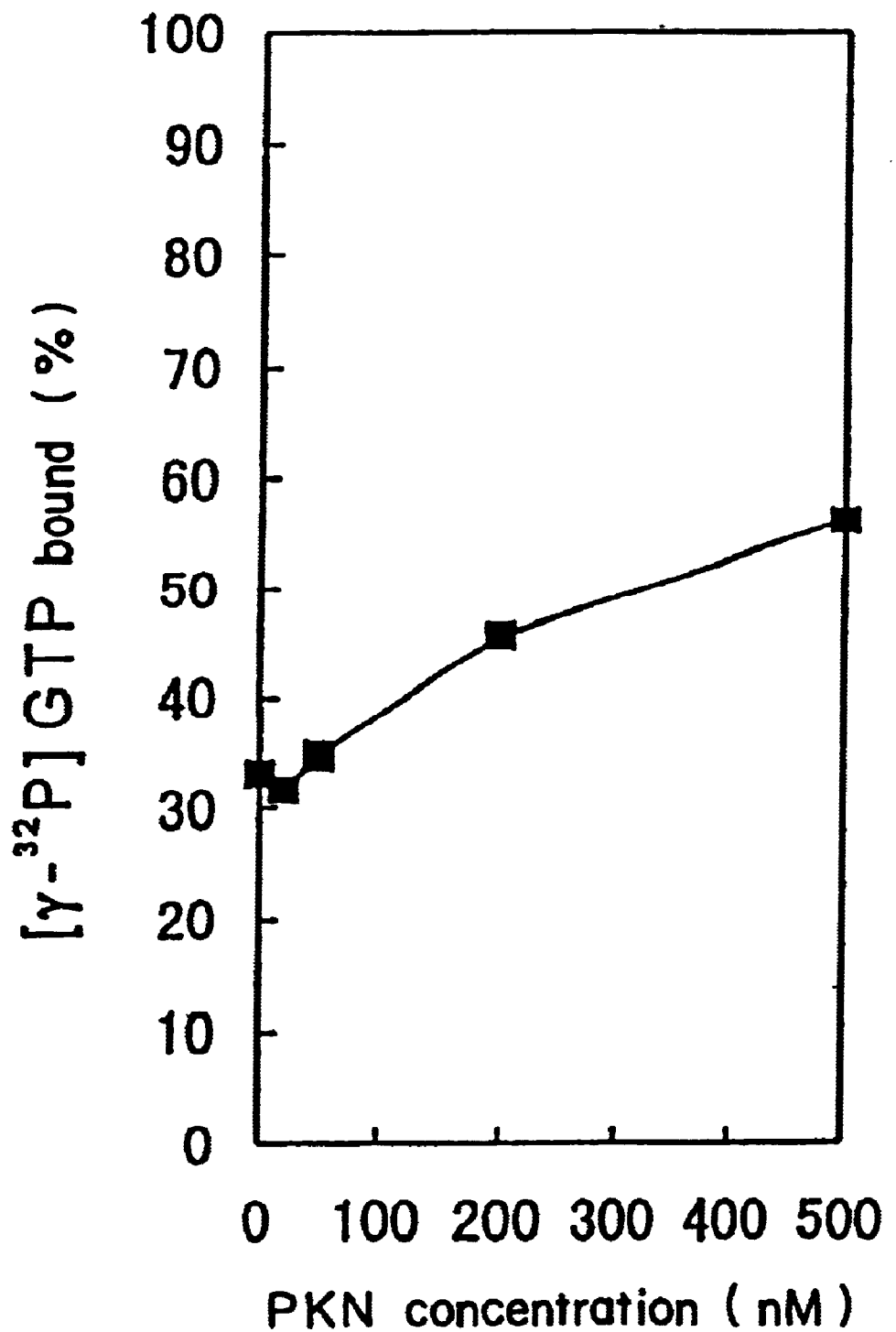

FIG. 31 illustrates the effects of PKN on the endogenous and GAP-stimulated GTPase activity of the Rho protein. 100 nM of [γ-$^{32}$p] GTP.GST-RhoA was incubated in the presence of GST-RhoGAP and MBP-PKN. The results were representative of three independent experiments.

Figure 32:
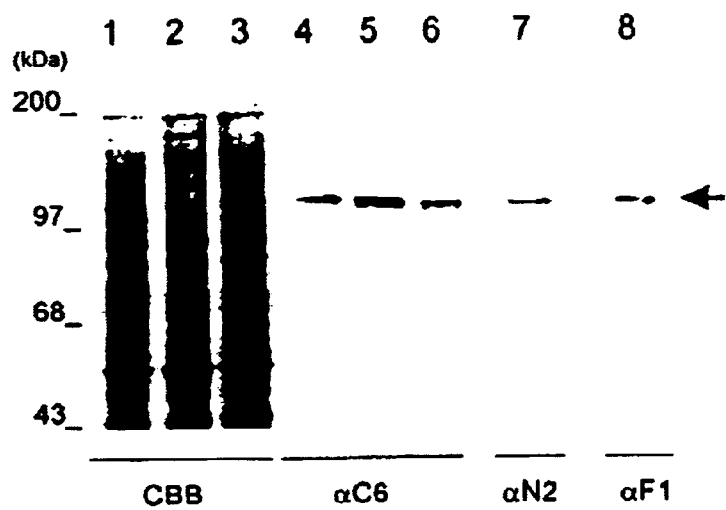

FIG. 32 is an electrophoretic photograph showing the immunoblottihg of PKN. Cell lysates (50 μg protein) from NIH 3T3 cells (lanes 1, 4, 7, and 8), Rat-1 cells (lanes 2 and 5), and Balb/c3T3 cells (lanes 3 and 6) were subjected to SDS-PAGE and then immunoblotting. Proteins were stained with Coomassie brilliant blue (CBB) (lanes 1–3). Immunostaining was performed with αC6 (lanes 4–6), αN2 (lane 7), and αF1 (lane 8). The positions of marker proteins are indicated in kDa, and the position of PKN is indicated by an arrow.

Figure 33:
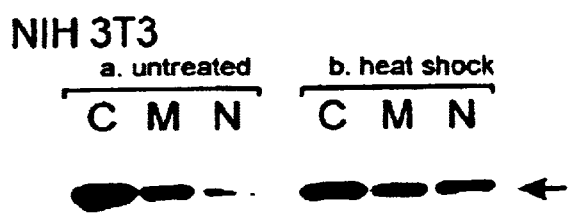
Figure 33:
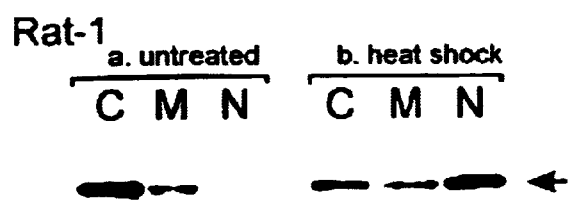
Figure 33:
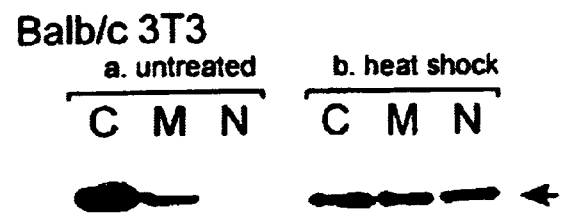

FIG. 33 is an electrophoretic photograph showing the effects of heat shock on subcellular distribution of PKN. Cells were treated at 42° C. for 90 min, homogenized, and fractionated into cytosolic (C), plasma membrane (M), and nuclear (N) fractions. PKN was detected by immunoblotting by using αC6. The positions of PKN in control untreated cells (a) and heat-shocked cells (b) are indicated by arrows. NIH3T3 cells: Each lane contains 19 μg of total protein. Rat-1 cells: Each lane contains 11 μg of total protein. Balb/c 3T3 cells: Each lane contains 11 μg of total protein.

Figure 34:
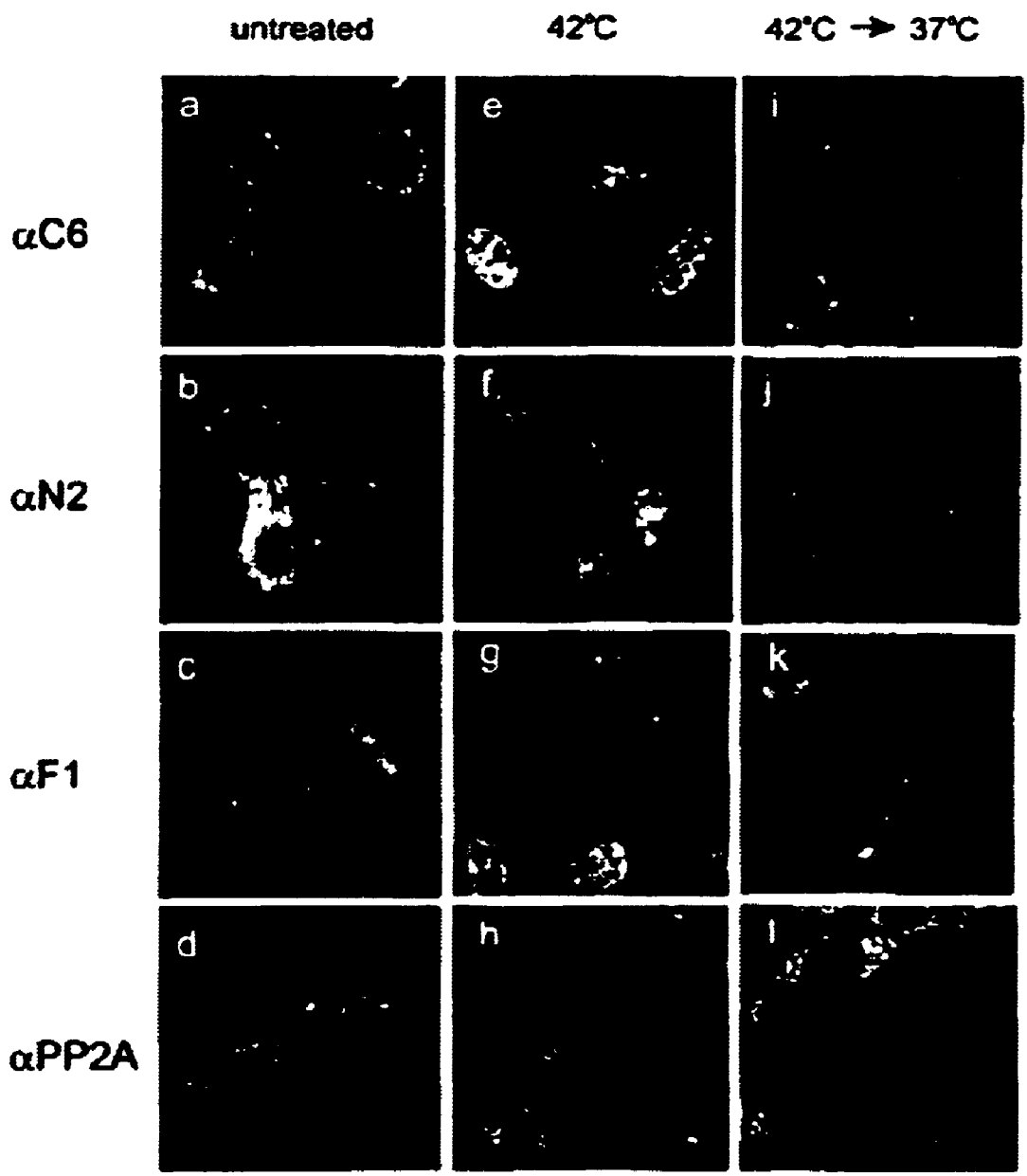

FIG. 34 is a photograph of PKN immunofluorescence staining showing the effects of heat shock on NIH 3T3 cells (a photograph of biological morphology). Control untreated cells (a–d), cells treated at 42° C. for 90 min (e–h), and cells incubated at 37° C. for 240 min following 90 min-heat shock (i–l) were immunostained by each antiserum. The first antiserum was αC6 (a, e, and i), αN2 (b, f, and j), αF1 (c, g, and k), and αPP2A (d, h. and l).

FIG. 35 is a photograph of PKN immunofluorescence staining showing the effects of heat shock on Rat-1 and Balb/c 3T3 cells (a photograph of biological morphology). Rat-1 (a, c, and e) and Balb/c 3T3 (b, d, and f) cells were exposed to heat shock at 42° C. The first antiserum was αC6. Control untreated cells (a and b); cells after 90 min-heat shock (c and d); cells after incubation at 37° C. for 240 min following 90 min-heat shock (e and f).

Figure 36:
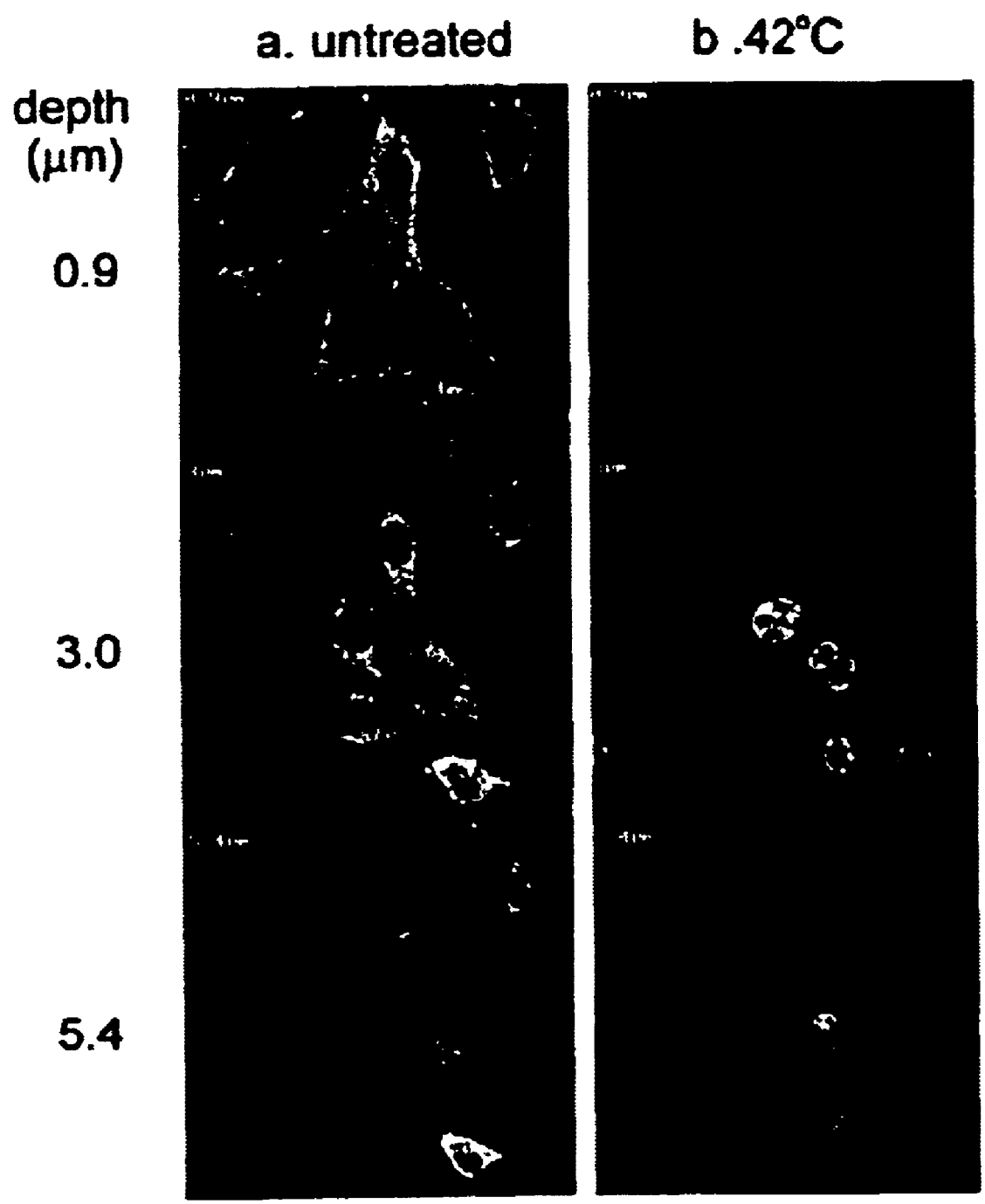

FIG. 36 is a photograph showing effects of heat shock on NIH 3T3 cells (a photograph of biological molphology). Control untreated cells (a) and cells treated at 42° C. for 90 min (b) were immunostained using αC6 and viewed on confocal laser scanning microscope. Optical sections from the bottom of the cells were performed at the indicated depths.

Figure 37:
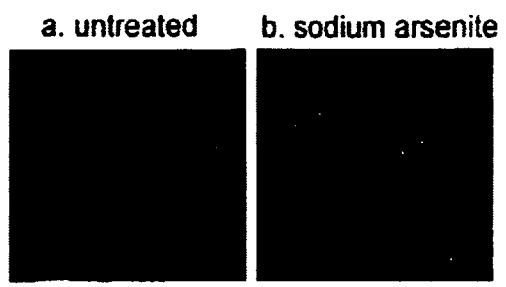

FIG. 37 is a photograph showing the effects of sodium arsenite on the immunofluorescence staining of PKN (a photograph biological molphology). Control untreated cells (a) and cells treated with 50 μM sodium arsenite at 37° C. for 2 hr (b), were immunostained using αC6.

Figure 38:
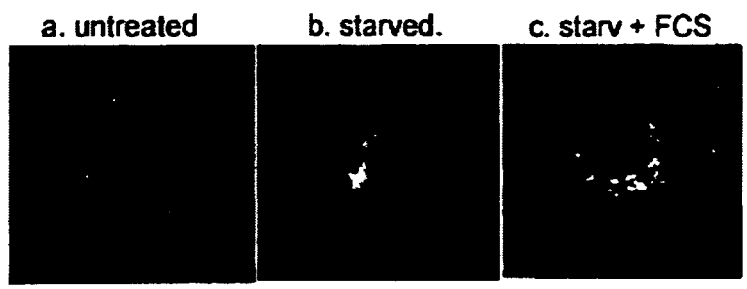

FIG. 38 is a photograph showing the effects of serum starvation on immunofluorescence staining of PKN (a photograph of biological molphology). Control untreated cells (a), cells serum starved for 24 hr at 37° C. (b), and cells incubated with 10% FCS at 37° C. for 4 hr following serum starvation (C), were immunostained using αC6.

Figure 39:
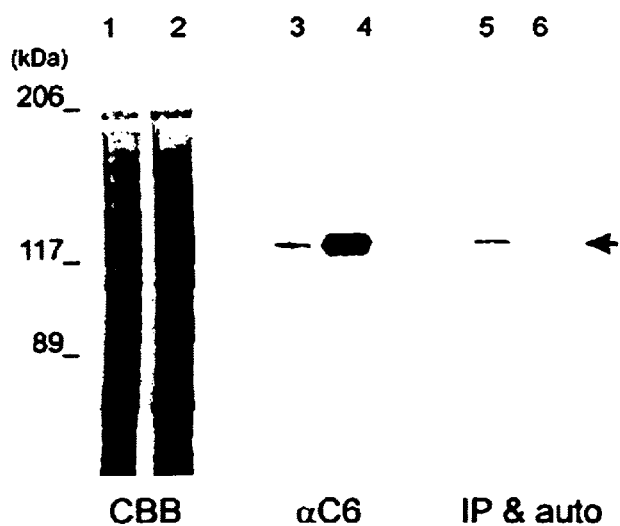

FIG. 39 is an electrophoretic photograph showing the effects by immunoblotting and autophosphorylation of PKN, of heat shock on PK⁻/neo#5 cells overexpressing PKN-PK⁻ mutant protein. Lysates of the wild type NIH 3T3 cells (lanes 1, 3, and 5) and of PK⁻/neo#5 cells (lanes 2, 4, and 6) were subjected to SDS-PAGE and proteins were stained with Coomassie brilliant blue (CBB) (lanes 1 and 2) and immunoblotting was performed using αC6 (lanes 3 and 4). Immunoprecipitation was carried out from these cells using αN2. Immunoprecipitates were autophosphorylated and subjected to SDS-PAGE followed by autoradiography (lanes 5 and 6). The positions of marker proteins are indicated in kDa, and the position of PKN is indicated by an arrow.

Figure 40:
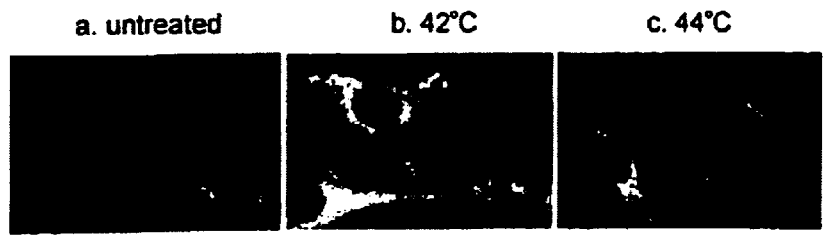

FIG. 40 is a photograph showing effects by immunofluorescence of PKN, of heat shock on PK⁻/neo#5 cells overexpressing PKN-PK⁻ mutant protein (a photograph of biological morphology). Control untreated cells (a), cells treated at 42° C. for 90 min (b), and cells treated at 44° C. for 90 min (c) were immunostained using antiserum αC6. Optical section in the center of the nuclei was performed at 2.5 μm from the bottom of the cells using confocal laser microscope.

Figure 41:
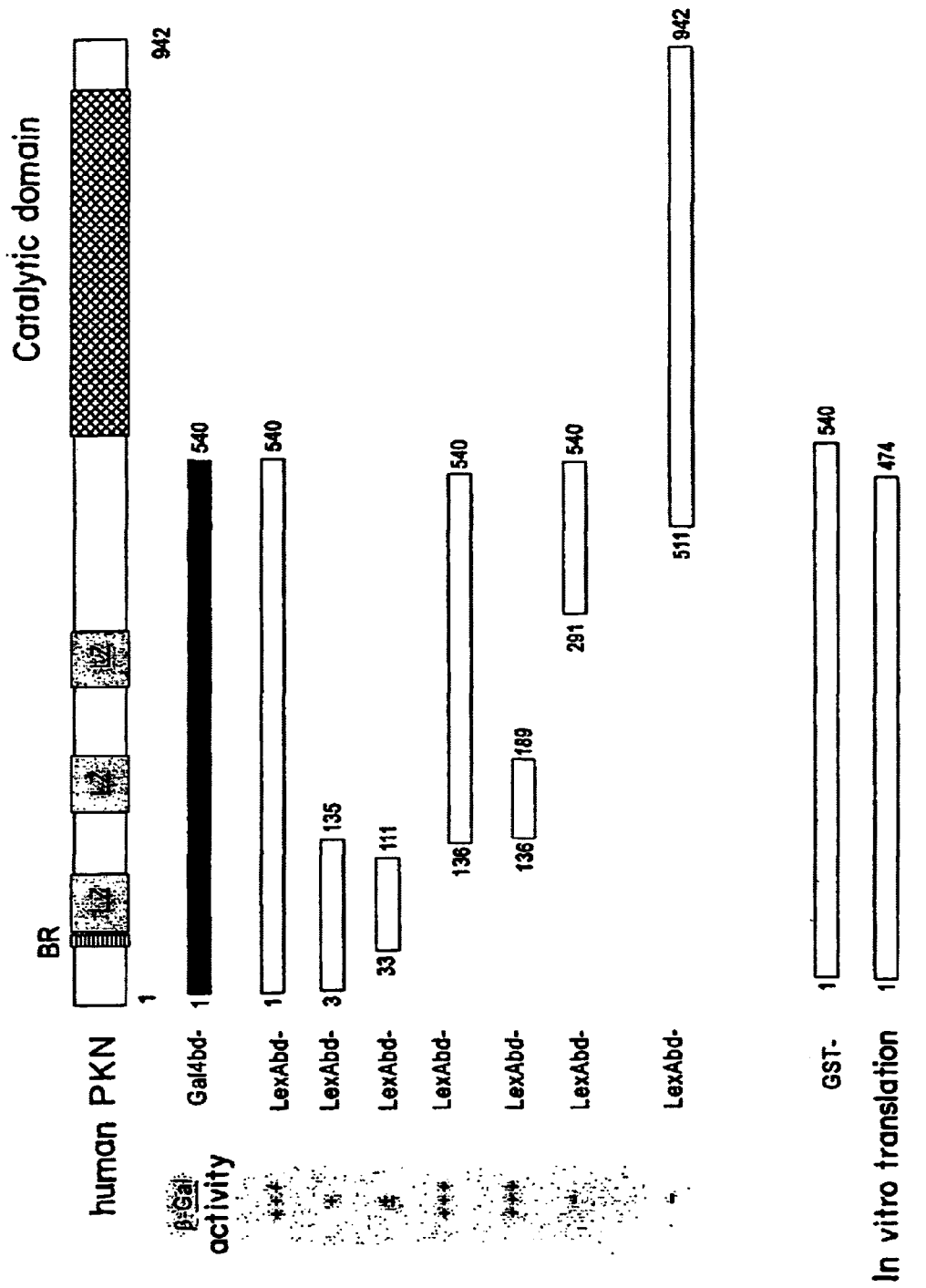

FIG. 41 schematically illustrates the expression constructs of human PKN and results of their interactions in the two-hybrid system. The schematic whole structure of each protein is represented at the top of each figure, and the deletion mutants of each protein are aligned below. The numbers preceding and following each line denote the positions of the most terminal amino acid residue of each clone, which is represented by solid or open box. The interaction in the two-hybrid system was examined by a filter assay for β-galactosidase activity. "+++" and "+" indicate the development of blue color within 20 min, and 24 hr from the initiation of the assay, respectively. "±" indicates the development of faint blue color after 24 hr from the initiation of assay, and "−" indicates no development of color within 24 hr. Gal4bd and LexAbd indicate the DNA binding domain of Gal4 and LexA, respectively. "LZ" indicates the leucine zipper-like motif. "BR" indicates the region rich in basic amino acid. Solid box indicates the bait construct.

Figure 42:
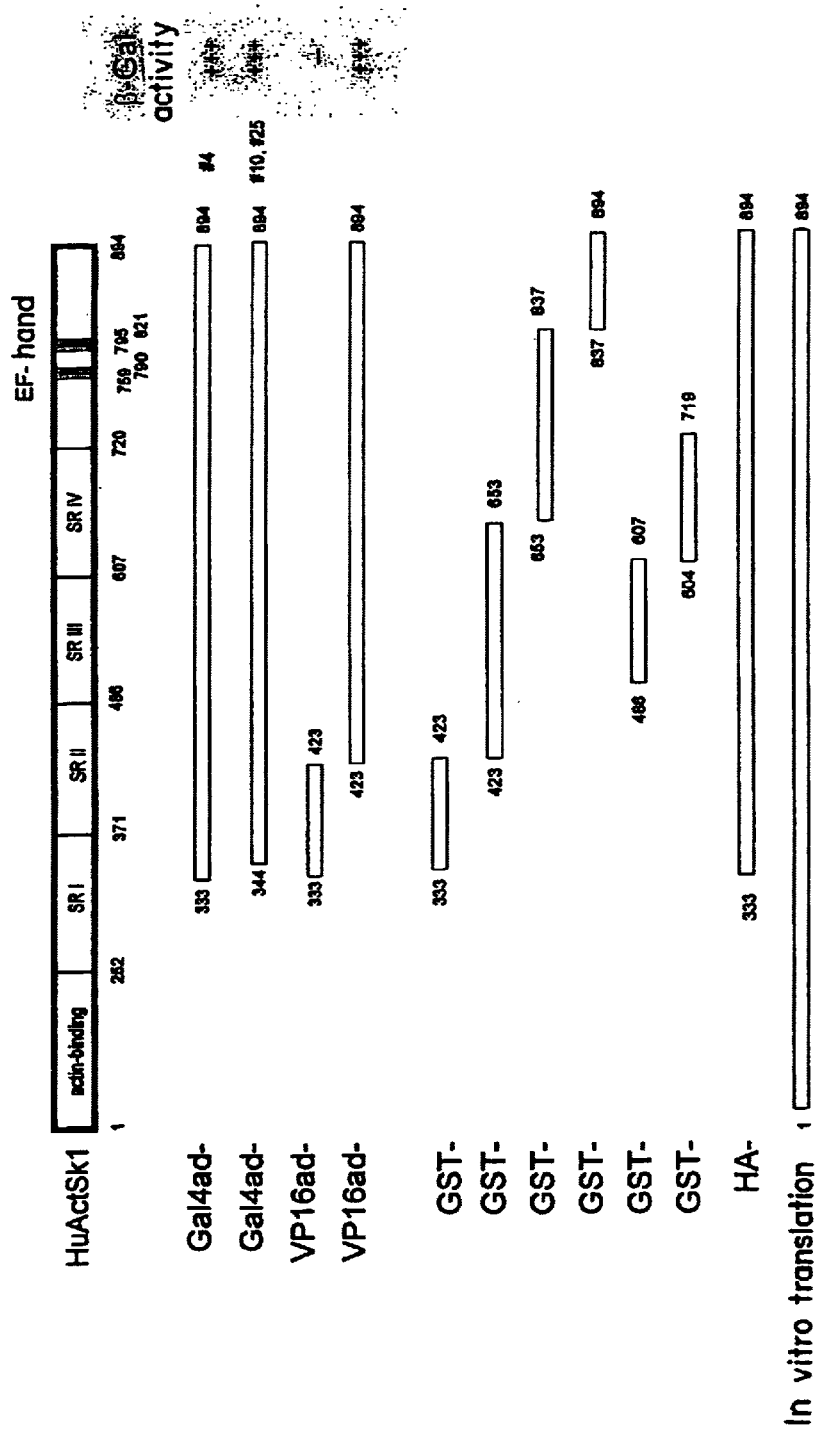

FIG. 42 schematically illustrates the expression constructs of HuActSkl (skeletal α-actinin) and HuActNm (non-skeletal muscle type α-actinin) and results of their interactions in the two-hybrid system. In the drawing, the abbreviations have the same meanings as those in FIG. 41. Gal4ad and VP16ad indicate the transcription activation domain of Gal4 and VP16, respectively. "SR" indicates spectrin-like repeats.

Figure 43:
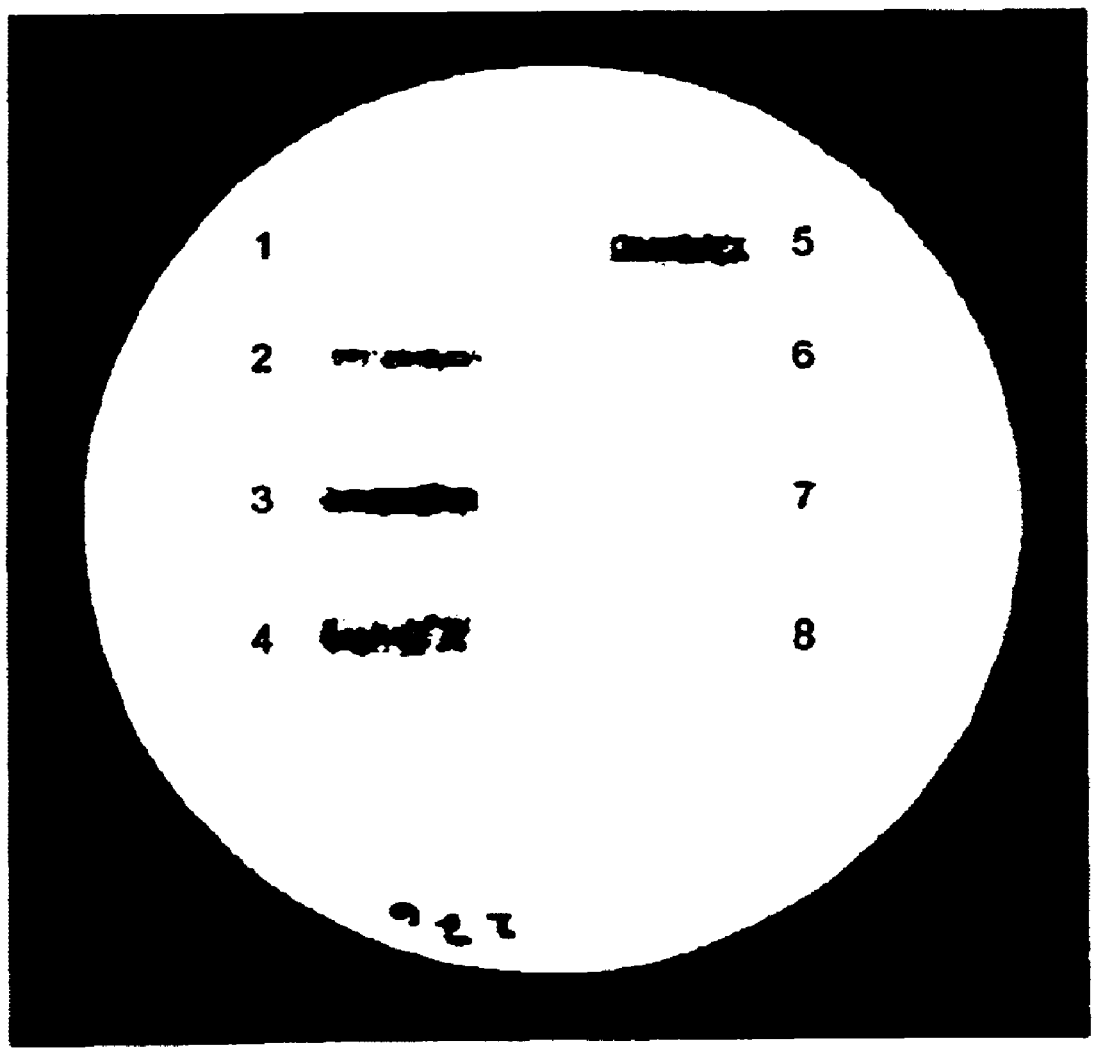

FIG. 43 is a photograph showing the interaction between PKN and HuActSkl in a two-hybrid system.

PKNN1 (lanes 1–4) or murine tumor suppresser P53 (amino acids 72–390) (lanes 5–8) was expressed as a fusion protein with LexA DNA binding domain, and its binding to SV40 larger T antigen (the amino acid sequence 84–708) (lanes 1 and 5), clone#21 protein (2 and 6), clone#4 protein (3 and 7), and clone#10 protein (4 and 8) expressed as fusion proteins with the Gal4 activation domain was examined by a filter assay for β-galactosidase activity. The clone#21 encodes the head-rod domain of neurofilament L protein (Mukai, H. et al., J. Biol. Chem., 271, 9816–9822 (1996)). The development of blue color 1 hr after the initiation of the filter assay of independent colonies picked from selected plates lacking Trp and Leu is shown in the photograph.

FIG. 44 is an electrophoretic photograph showing the analysis of in vitro binding between PKN and HuActSkl. $^{35}$S-Labeled in vitro translated N-terminal region of PKN (the amino acid sequence 1–474, this region being designated as PKNN2; lanes 1–7 and 11–17) or PKNΔBa1 (the amino acid sequence 136–474; lanes 8–10 and 18–20) was incubated with GST synthesized in E. coli or GST-fused various deletion mutants of HuActSkl as indicated in FIG. 42 and fusion proteins. Aliquots of the initial binding reaction mixtures (10 μl) were removed before precipitation and applied to electrophoresis, which were indicated as "Input" shown in the upper panel. GST or GST-fused proteins were collected with glutathione-Sepharose beads and analyzed by 10% SDS-PAGE, followed by autoradiography, which were indicated as "G-beads" shown in the lower panel.

Lanes 1 and 11, GST-HuActSkl (333–423); lanes 2, 8, 12, and 18, GST-HuActSkl (423–653); lanes 3, 9, 13, and 19, GST-HuActSkl (653–837); lanes 4 and 14, GST-HuActSkl (837–894); lanes 5 and 15, GST-HuActSkl (486–607); lanes 6 and 16, GST-HuActSkl (604–719); lanes 7, 10, 17, and 20, GST. White arrowheads indicate the position of labeled PKNN2, and black arrowheads the position of the labeled PKNΔBa1. Molecular mass markers are indicated in kDa.

FIGS. 45A and 45B are electrophoretic photographs showing the binding between PKN and HuActNm.

$^{35}$S-Labeled in vitro translated PKNN2 was incubated with GST synthesized in E. coli or GST-fused various deletion mutants of HuActNm as indicated in FIG. 42. Aliquots of the initial binding reaction mixtures (10 μl) were removed before precipitation and applied to electrophoresis, which were indicated as "Input". GST or GST-fused proteins were collected with glutathione-Sepharose beads and analyzed by 10% SDS-PAGE, followed by autoradiography. White arrowheads indicate the position of labeled protein. Molecular mass markers are indicated in kDa.

A: Specific binding of PKN to the deletion mutants of HuActNm. Lanes 1 and 4, GST-HuActNm (the amino acid sequence 479–600); lanes 2 and 5, GST-HuActNm (the amino acid sequence 712–834); lanes 3 and 6, GST.

B: Effect of $Ca^{2+}$ on binding of HuActNm to EF-hand-like region. GST-HuActNm (the amino acid sequence 712–834) was incubated with in vitro translated PKN in the absence of $Ca^{2+}$ (lanes 1 and 3) or in the presence of 1 mM $Ca^{2+}$ (lanes 2 and 4).

Figure 46:

FIG. 46 is an electrophoretic photograph showing the specific binding of PKN to spectrin-like repeats of α-actinin.

$^{35}$S-Labeled in vitro translated PKNN2 was incubated with GST synthesized in E. coli or GST-fused spectrin-like repeats of α-actinin or spectrin repeat of α-spectrin. Aliquots of the initial binding reaction mixtures (10 μl) were removed before precipitation and applied to electrophoresis, which were indicated as "Input". GST or GST-fused proteins were collected with glutathione-Sepharose beads and analyzed by 10% SDS-PAGE, followed by autoradiography. The white arrowhead indicates the position of the labeled protein. Molecular mass markers are indicated in kDa. Lanes 1 and 5, GST-spectrin-like repeat 3 of HuActSkl (the amino acid sequence 486–607); lanes 2 and 6, GST-spectrin-like repeat 3 of HuActNm (the amino acid sequence 479–600); lanes 3 and 7, GST-spectrin repeat 20 of α-spectrin; lanes 4 and 8, GST.

Figure 47:
Figure 47:
Figure 47:
Figure 47:
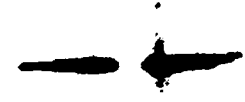
Figure 47:

FIG. 47 is an electrophoretic photograph showing the in vivo binding of PKN to HuActSkl.

A vector pHA-Act encoding HA epitope fused to the amino acid sequence 333–894 of HuActSkl (lanes 1, 3, and 5) or pHA vector (2, 4, and 6) was cotransfected into COS7 cells with the expression vector pMhPKN3 (Mukai, H. & Ono, Y., Biochem. Biopys. Res. Commun. 199, 897–904 (1994)) encoding the full-length human PKN. Cells were extracted, and recombinant polypeptides were immunoprecipitated using anti-HA antibody 12CA5. PKN and HuActSkl in each extract (lanes 3–6) and in each immunoprecipitate (lanes 1–2) were detected by immunoblotting with anti-PKN antiserum αC6 (lanes 1–4) and 12CA5 (lanes 5 and 6), respectively. A white arrow indicates the position of PKN. A black arrow indicates the position of HA-HuActSkl.

FIGS. 48A and 48B are electrophoretic photographs showing the effects of PI4,5P2 on binding between PKN and α-actinin. $^{35}$S-Labeled in vitro translated full-length coding region of HuActSkl was incubated with GST synthesized in E. coli or GST-fused PKNN1. Aliquots of the initial binding reaction mixtures (10 μl) were removed before precipitation and applied to electrophoresis, which were indicated as "Input". GST or GST-fused proteins were collected with glutathione-Sepharose beads and analyzed by 8% SDS-PAGE, followed by autoradiography. Arrows indicate the position of labeled HuActSkl.

A: Specific binding of full-length α-actinin to PKN in the absence (lanes 1, 2, 5, and 6) or presence (lanes 3, 4, 7 and 8) of 10 μM PI4,5P2. Lanes 1, 3, 5 and 7, GST-PKNN1; lanes 2, 4, 6 and 8, GST.

B: Effects of concentration of PI4,5P2 on binding activity of full-length α-actinin to PKN. Lanes 1 and 6, 0 μM of PI4,5P2; lanes 2 and 7, 2.5 μM of PI4,5P2; lanes 3 and 8, 10 μM of PI4,5P2; lanes 4 and 9, 30 μM of PI4, 5P2; lanes 5 and 10, 100 μM of PI4,5P2.

FIG. 49 is an electrophoretic photograph showing phosphorylation of actin and actin-binding proteins by PKN. 100 ng of purified G-actin (lanes 1–3) or caldesmon (lanes 4–6) was incubated in the assay mixture without (lanes 1 and 4) or with (lanes 2, 3, 5 and 6) of PKN purified from rat testis in the absence (lanes 2 and 5) or presence (lanes 3 and 6) of 40 μM arachidonic acid. Phosphorylation was detected by an autoradiograph of 10% SDS-PAGE. A white arrowhead indicates the position of autophosphorylation of PKN, a black arrow the position of caldesmon, and a back arrowhead the position of G-actin.

DETAILED DESCRIPTION OF THE INVENTION

Definition

The term "amino acid" herein refers to the meaning including either of optical isomers, i.e., an L-isomer and a D-isomer. Thus, the term "peptide" herein refers to the meaning including not only peptides constituted by L-amino acids solely but also peptides comprising D-amino acids partially or totally.

Furthermore, the term "amino acid" herein refers to the meaning including not only twenty α-amino acids which constitute natural proteins but also other α-amino acids as well as β-, δ- and γ-amino acids, non-natural amino acids, and the like. Thus, amino acids with which peptides are substituted or amino acids inserted into peptides as shown below are not restricted to twenty α-amino acids which constitute natural proteins but may be other α-amino acids as well as β-, γ- and δ-amino acids, non-natural amino acids, and the like. Such β-,γ- and δ-amino acids include β-alanine, γ-aminobutyric acid or ornithine. In addition, the amino acids other than those constituting natural proteins or the non-natural amino acids include 3,4-dihydroxyphenylalanine, phenylglycine, cyclohexylglycine, 1,2,3,4-tetrahydroisoquinolin-3-carboxylic acid or nipecotinic acid.

Activated Rho Protein Binding Protein

The activated Rho protein binding protein according to the present invention is a peptide comprising a modified amino acid sequence of Protein Kinase N having activated Rho protein binding activity and not having protein kinase activity, or derivatives thereof. As used herein, the term modified amino acid sequence refers to an amino acid sequence modified by addition and/or insertion of one or more amino acid sequences and/or by substitution and/or deletion of one or more amino acids. Therefore, the partial amino acid sequence of PKN (constituted by a partial sequence of the full amino acid sequence of PKN) having the activated Rho protein binding activity and not having protein kinase activity is also an embodiment of the modified amino acid sequences. The term protein used herein refers to peptides. The term peptide used herein refers to derivatives of peptides.

The full amino acid sequence of PKN, for example, the sequence of amino acids derived from human being, is known in the art and described in SEQ ID NO: 3. The full amino acid sequence of PKN derived from a species other than human being (for example, rat, bovine, and xenopus), which is homologous to the sequence of the human PKN, is also included in the expression of full amino acid sequence of PKN used herein.

PKN can be obtained, for example, by expressing the cDNA sequence in a host such as bacteria according to a conventional method. The cDNA sequence can be obtained by screening a commercially available cDNA library with a base sequence encoding a part of the amino acid sequence as a probe. The sequence of PKN derived from human being can be isolated as described in Mukai, H. & Ono, Y. Biochem. Biophys. Res. Commun. 199. 897–904 (1994).

There are isozymes for PKN, and such isozymes include Protein Kinase C-related kinase 2 and Protein Kinase C-related kinase 3 (Palmer, R. et al., ibid.). The term "Protein Kinase N" used herein refers to isozymes of PKN.

The origin of PKN is not particularly limited, and PKN may be derived from mammals including human being or other origins. PKN can be obtained, for example, as described in H. Mukai et al., Biochem. Biophys. Res. Commun., 204, 348–356 (1994), or Example 1.

The Rho protein includes RhoA, RhoB, RhoC, and RhoG proteins.

Furthermore, the term Rho protein used herein refers to Rho proteins which have been modified so that binding between the Rho protein and PKN is not substantially damaged. Such modified Rho proteins include RhoA mutant in which the amino acid 14 has been substituted by valine (RhoA$^{Val14}$), RhoA mutant which lacks the C-terminal lipid modification site (CLVL$^-$), and RhoA mutant in which the amino acid 14 has been substituted by valine with the C-terminal lipid modification site being deleted (RhoA$^{Val14}$CLVL$^-$).

The wording "amino acid sequence having activated Rho protein binding activity" used herein means an amino acid sequence which is evaluated by one skilled in the art to bind to the activated Rho protein, for example, proteins which are evaluated to bind to the activated Rho protein when examined under the same conditions as in Examples 1, 4, 5 and 16–18.

The activated Rho protein binding protein has no protein kinase activity. The wording "not having protein kinase activity" used herein refers to not having serine/threonine protein kinase catalytic activity of PKN and more specifically refers to the amino acid sequence from 541 onward or from 112 onward in SEQ ID No: 1 not having protein kinase catalytic activity by addition and/or insertion of one or more amino acid sequences and/or by substitution and/or deletion of one or more amino acids and, in the case of a sequence other than that of human being, a sequence corresponding to the above sequence.

The activated Rho protein binding protein may also be a peptide which binds to cytoskeletal proteins (intermediate filaments and/or α-actinin), or a peptide which, under stress, inhibits the translocation of PKN from cytoplasm to nucleus (see examples described hereinafter).

The term "derivatives of peptides" herein includes peptides in which an amino group at an amino terminal (N-terminal) or all or a part of amino groups of side chains of amino acids, and/or a carboxyl group at a carboxyl terminal (C-terminal) or all or a part of carboxyl groups of side chains of amino acids, and/or functional groups other than the amino groups and carboxyl groups of the side chains of the amino acids such as hydrogen, a thiol group or an amido group have been modified by appropriate other substituents. The modification by the appropriate other substituents is carried out in order to, for example, protect functional groups in the peptide, improve safety and tissue-translocation of the protein or enhance the protein activity.

The derivatives of the peptides include:

(1) peptides in which one or more hydrogen atoms of the amino group at the amino terminal (N-terminal) or a part or all of the amino groups of the side chains of the amino acids are replaced by substituted or unsubstituted alkyl groups (which may be straight chain or branched chain or cyclic chain) such as a methyl group, an ethyl group, a propyl group, an isopropyl group, an isobutyl group, a butyl group, a t-butyl group, a cyclopropyl group, a cyclohexyl group or a benzyl group, substituted or unsubstituted acyl groups such as a formyl group, an acetyl group, a caproyl group, a cyclohexylcarbonyl group, a benzoyl group, a phthaloyl group, a tosyl group, a nicotinoyl group or a piperidincarbonyl group, urethane-type protective groups such as a p-nitrobenzyloxycarbonyl group, a p-methoxybenzyloxycarbonyl group, a p-biphenylisopropyl-oxycarbonyl group or a t-butoxycarbonyl group, or urea-type substituents such as a methylaminocarbonyl group, a phenylcarbonyl group or a cyclohexylaminocarbonyl group;

(2) peptides in which the carboxyl groups at the carboxyl terminal (C-terminal) or a part or all of the side chains of the amino acids are esterified (for example, the hydrogen atom(s) are replaced by methyl, ethyl, isopropyl, cyclohexyl, phenyl, benzyl, t-butyl or 4-picolyl), or amidated (for example, unsubstituted amides or C1-C6 alkylamide such as an methylamide, an ethylamide or an isopropylamide are formed; or (3) peptides in which a part or all of the functional groups other than the amino groups and the carboxyl groups of the side chains of the amino acids such as hydrogen, a thiol group or an amino group are replaced by the substituents described before or a trityl group.

Examples of the activated Rho protein binding protein include those comprising a modified amino acid sequence of human Protein Kinase N having activated RhoA protein binding activity and not having serine/threonine-protein kinase activity. Furthermore, examples thereof include those comprising the sequence of the amino acids sequence 7–540, 7–155, 1–538, 3–135, or 33–111 in SEQ ID NO: 1 and a modified amino acid sequence of said sequence (for example, partial sequence) having activated Rho protein binding activity.

In addition, the activated Rho protein binding proteins include those comprising the amino acid sequence 74–93, 94–113, or 82–103 in SEQ ID NO: 1 or a modified amino acid sequence of the sequence (for example, partial sequence) having activated Rho protein binding activity. As Shown in examples described hereinafter, the peptide comprising the amino acid sequence 82–103 in SEQ ID NO: 1 has an excellent inhibitory activity against binding between the Rho protein and PKN.

Activated Rho protein binding proteins which bind to cytoskeletal proteins (for intermediate filaments and α-actinin) include, for example, the amino acid sequence 1–474 and the amino acid sequence 136–189 in SEQ ID NO: 1.

Activated Rho protein binding proteins which inhibit the translocation of PKN from cytoplasm to nucleus include, for example, the amino acid sequence of SEQ ID NO: 1 with Lys 644 being substituted by Arg (PKN-PK⁻).

The activated Rho protein binding protein can bind to the activated Rho protein. The Rho protein is closely involved in tumorigenesis and metastasis and, in addition, the expression of cell functions such as cell morphology, cell movement, cell adhesion, cell division, and gene transcription activation (Takai, Y., et al., ibid.; G. C. Prendergast. et al., ibid.; Khosravi-Far, R., et al., ibid.; R. Qiu et al., ibid.; Lebowitz, P., et al., ibid.; and Yoshioka, K. et al., ibid.). Therefore, the activated Rho binding protein is considered to be useful in elucidating the mechanism of tumorigenesis and metastasis. Furthermore, it is considered to be useful in the elucidation of cell functions.

Protein Having Inhibitory Activity Against Binding Between the Activated Rho Protein and PKN The protein inhibiting binding between activated Rho protein and PKN according to the present invention consists of a peptide comprising a modified amino acid sequence of Protein Kinase N inhibiting binding between the activated Rho protein and Protein Kinase N or derivatives thereof. The term "modified amino acid sequence" used herein has the same meaning as described above. Therefore, the partial amino acid sequence of PKN (constituted by a partial sequence of the full amino acid sequence of PKN) inhibiting the binding between the activated Rho protein and Protein Kinase N is also an embodiment of the modified amino acid sequences.

In the present invention, the wording "amino acid sequence inhibiting binding between the activated Rho protein and Protein Kinase N" is an amino acid sequence which is evaluated by one skilled in the art to inhibit the binding between the actiavated Rho protein and Protein Kinase N, for example, amino acid sequences which are evaluated to inhibit the binding between the activated Rho protein and Protein Kinase N when examined under the same conditions as in Example 17.

Examples of proteins inhibiting the binding between the activated Rho protein and PKN include those comprising the amino acid sequence 7–540, 7–155, 1–540, 3–135, or 33–111 in SEQ ID NO: 1 and a modified amino acid sequence of said sequence (for example, partial sequence) inhibiting the binding between the activated Rho protein and PKN.

Furthermore, proteins inhibiting the binding between the activated Rho protein and PKN include those comprising the amino acid sequence 74–93, 94–113, or 82–103 in SEQ ID NO: 1 or a modified amino acid sequence of the sequence (for example, partial sequence) inhibiting the binding between the activated Rho protein and PKN. As shown in examples described hereinafter, the peptide comprising the amino acid sequence 82–103 in SEQ ID NO: 1 has an excellent inhibitory activity against the binding between the activated Rho protein and PKN.

The protein inhibiting the binding between the activated Rho protein and PKN according to the present invention may comprise a modified amino acid sequence of Protein Kinase N having the activated Rho protein binding activity and not having the protein kinase activity.

The activated Rho protein binding protein may have the inhibitory activity against the binding between the activated Rho protein and Protein Kinase N.

Thus, according to the present invention, there is provided a peptide comprising a modified amino acid sequence of Protein Kinase N having the activated Rho protein binding activity, not having the protein kinase activity, and inhibiting the binding between the activated Rho protein and Protein Kinase N or derivatives thereof.

The protein inhibiting the binding between the activated Rho protein and PKN can inhibit the binding between the activated Rho protein and PKN. The Rho protein is closely involved in tumorigenesis and metastasis and, in addition, the expression of cell functions such cell morphology, cell adhesion, cell movement, cell division, and gene transcription activation (Takai, Y., et al., ibid.; G. C. Prendergast. et al., ibid.; Khosravi-Far, R., et al., ibid.; R. Qiu et al., ibid.; and Lebowitz, P., et al., ibid.). Therefore, the protein inhibiting the binding between the activated Rho protein and PKN is considered to be useful in elucidating the mechanism of tumorigenesis and metastasis. Furthermore, it is considered to be useful in elucidating cell functions.

Intermediate Filament Binding Protein

The intermediate filament binding protein according to the present invention consists of a peptide comprising a modified amino acid sequence of Protein Kinase N having intermediate filament binding activity and not having protein kinase activity or derivatives thereof. The term "modified amino acid sequence" used herein has the same meaning as described above. Therefore, the partial amino acid sequence of PKN (constituted by a partial sequence of the full amino acid sequence of PKN) having intermediate filament binding activity and not having protein kinase activity is also an embodiment of the modified amino acid sequences.

"Intermediate filaments" referred to in the present invention include vimentin, neurofilament-L (NFL), neurofilament-M (NFM), neurofilament-H (NFH), acidic keratin, neutral keratin, basic keratin, desmin, glia fibrillary acidic protein (GFAP), lamin, and nestin.

In the present invention, the wording "amino acid sequence having intermediate filament binding activity" refers to an amino acid sequence which is evaluated by one skilled in the art to bind to the intermediate filament or the head-rod domain of the intermediate filament, for example, amino acid sequences which are evaluated to bind to the intermediate filament, the amino acid sequence 1–349 in human NFL, or the amino acid sequence 1–411 in human NFM.

The intermediate filament binding protein does not have protein kinase activity. In the present invention, the wording "not having protein kinase activity" refers to not having serine/threonine protein kinase catalytic activity of PKN and more specifically refers to the amino acid sequence from 475 onward or from 541 onward in SEQ ID No: 1 not having serine/threonine protein kinase catalytic activity by addition and/or insertion of one or more amino acid sequences and/or by substitution and/or deletion of one or more amino acids and, in the case of a sequence other than that of human being, a sequence corresponding to the above sequence.

Examples of intermediate filament binding proteins include those comprising a modified amino acid sequence of human PKN having intermediate filament binding activity and not having serine/threonine protein kinase activity. Furthermore, examples thereof include those comprising the amino acid sequence 1–474, 1–540, 1–32, 112–540, or 112–474 in SEQ ID NO: 1 or a modified amino acid sequence of the sequence (for example, partial sequence) having the intermediate filament binding activity.

The intermediate filament binding protein has the intermediate filament binding activity. The intermediate filament is known to have an important role in signal transduction in the cytoskeleton (N. Inagaki et al., Trend. Biochem. Sci., 19, 448–452 (1994)). Therefore, the intermediate filament binding protein is considered to be useful in elucidating the mechanism of tumorigenesis and metastasis. Furthermore, it is considered to be useful in elucidating the mechanism of information transduction.

α-actinin Binding Protein

The α-actinin binding protein according to the present invention consists of a peptide comprising a modified amino acid sequence of Protein Kinase N having α-actinin binding activity and not having protein kinase activity or derivatives thereof. The term "modified amino acid sequence" used herein has the same meaning as described above. Therefore, the partial amino acid sequence of PKN (constituted by a partial sequence of the full amino acid sequence of PKN) having α-actinin binding activity and not having protein kinase activity is also an embodiment of the modified amino acid sequences.

"α-actinins" referred to in the present invention include a skeletal muscle type α-actinin and a non-skeletal muscle type α-actinin.

In the present invention, the wording "amino acid sequence having α-actinin binding activity" refers to an amino acid sequence which is evaluated by one skilled in the art to bind to α-actinin or intermediate portions of α-actinin (for example, spectrin-like repeats and EF-hand-like motifs, and the amino acid sequence 423–653, 653–837, 486–607, or 333–894 of human skeletal muscle type α-actinin or the amino acid sequence 479–600 or 712–843 of human non-skeletal muscle type α-actinin.

The α-actinin binding protein does not have the protein kinase activity. In the present invention, the wording "not having protein kinase activity" means not having serine/threonine protein kinase catalytic activity of PKN and more specifically refers to the amino acid sequence from 475 onward or from 541 onward in SEQ ID No: 1 not having the serine/threonine protein kinase catalytic activity by addition and/or insertion of one or more amino acid sequences and/or by substitution and/or deletion of one or more amino acids and, in the case of a sequence other than that of human being, a sequence corresponding to the above sequence.

Examples of α-actinin binding proteins include those comprising a modified amino acid sequence of human PKN having the α-actinin binding activity and not having the serine/threonine protein kinase activity. Furthermore, examples thereof include those comprising the amino acid sequence 1–540, 3–135, 136–540, or 136–189 in SEQ ID NO: 1 or a modified amino acid sequence of the sequence (for example, partial sequence) having the α-actinin binding activity.

The α-actinin binding protein has the α-actinin binding activity. The α-actinin is a cytoskeletal protein which causes crosslinking between actinin filaments or between an actinin filament and a cell adhesion machinery or the like and is known to play an important role in cell morphology, cell adhesion, cell movement and the like (see prior art noted above). Therefore, the α-actinin binding protein is considered to be useful in elucidating the mechanism of control of the cell morphology and cell adhesion by Rho and PKN. Furthermore, it is considered to be useful in elucidating the mechanism of such signal transduction.

Protein Having Activity to Bind to Catalytic Region of PKN

The protein having activity to bind to the catalytic region of PKN comprises a peptide comprising a modified amino acid sequence of PKN having activity to bind to the catalytic region of PKN and not having protein kinase activity or derivatives thereof. The term "modified amino acid sequence" used herein has the same meaning as described above. Therefore, the partial amino acid sequence of PKN (constituted by a partial sequence of the full amino acid sequence of PKN) having activity to bind to the catalytic region of PKN and not having protein kinase activity is also an embodiment of the modified amino acid sequences.

In the present invention, the wording "amino acid sequence having activity to bind to the protein kinase catalytic domain of Protein Kinase N" refers to an amino acid sequence which is evaluated by one skilled in the to bind to the protein kinase catalytic region of PKN, for example, amino acid sequences which are evaluated to bind to the protein kinase catalytic region of PKN when examined under the same conditions as in Example 11 or 12.

Protein kinase catalytic domains of Protein Kinase N, to which the protein having activity to bind to the catalytic domain of PKN binds, include, for example, the amino acid sequence 511–942, the amino acid sequence 614–942, and the amino acid sequence 634–942 in SEQ ID NO: 1.

The protein having activity to bind to the catalytic region of PKN according to the present invention does not have protein kinase activity. In the present invention, the wording "not having any protein kinase activity" refers to not having serine/threonine protein kinase catalytic activity of PKN and more specifically refers to the amino acid sequence from 541 onward or from 475 onward in SEQ ID No: 1 not having the serine/threonine protein kinase catalytic activity by addition and/or insertion of one or more amino acid sequences and/or by substitution and/or deletion of one or more amino acids and, in the case of a sequence other than that of human being, a sequence corresponding to the above sequence.

Examples of proteins having activity to bind to the catalytic domain of PKN include a protein having a modified amino acid sequence of human PKN having the activity to bind to the catalytic domain of PKN and not having the serine/threonine protein kinase activity. Furthermore, examples thereof include those comprising the sequence of the amino acid sequence 1–540 or 1–474 in SEQ ID NO: 1 or a modified amino acid sequence of the sequence (for example, partial sequence) having the activity to bind to the catalytic domain of PKN.

The protein having the activity to bind to the catalytic domain of PKN has the activity to bind to the protein kinase catalytic domain of PKN. Therefore, the protein having the activity to bind to the catalytic domain of PKN is considered to be useful in elucidating the mechanism of tumorigenesis and metastasis. Furthermore, it is considered to be useful in elucidating the signal transduction by PKN.

Peptide Having Inhibitory Activity Against Protein Kinase Activity of PKN

The peptide inhibiting the protein kinase activity of PKN according to the present invention is a peptide comprising a modified amino acid sequence of Protein Kinase N inhibiting protein kinase activity of Protein Kinase N and not having protein kinase activity or derivatives thereof. The term "modified amino acid sequence" used herein has the same meaning as described above. Therefore, the partial amino acid sequence of PKN (constituted by a partial sequence of the full amino acid sequence of PKN) inhibiting the protein kinase activity of PKN and not having the protein kinase activity is also an embodiment of the modified amino acid sequences.

In the present invention, the wording "amino acid sequence inhibiting protein kinase activity of Protein Kinase N" refers to an amino acid sequence which is evaluated by one skilled in the art to inhibit the protein kinase activity of PKN, for example, amino acid sequences which are evalu-ated to inhibit the protein kinase activity of PKN when examined under the same conditions as in Example 14 or 15.

The peptide inhibiting the protein kinase activity of PKN does not have the protein kinase activity. In the present invention, the wording "not having protein kinase activity" refers to not having serine/threonine protein kinase catalytic activity of PKN and more specifically refers to the amino acid sequence from 541 onward or from 475 onward in SEQ ID No: 1 not having serine/threonine protein kinase catalytic activity by addition and/or insertion of one or more amino acid sequences and/or by substitution and/or deletion of one or more amino acids and, in the case of a sequence other than that of human being, a sequence corresponding to the above sequence.

Examples of peptides inhibiting the protein kinase activity of PKN include proteins comprising a modified amino acid sequence of human PKN inhibiting the protein kinase activity of Protein Kinase N and not having the serine/threonine protein kinase activity. Furthermore, examples thereof include those comprising the amino acid sequence 39–53 in SEQ ID NO: 1, or a modified amino acid sequence of the sequence (for example, partial sequence) inhibiting the protein kinase activity.

The peptide inhibiting the protein kinase activity of PKN inhibits the protein kinase activity of PKN. Therefore, the peptide having the inhibitory activity against the protein kinase activity of PKN is considered to be useful in elucidating the mechanism of tumorigenesis and metastasis. Furthermore, it is considered to be useful in elucidating the cell signal transduction by PKN.

The protein having the activity to bind to the catalytic region of PKN may have inhibitory activity against the protein kinase activity of PKN. The peptide inhibiting the protein kinase activity of PKN may also have the activity to bind to the protein kinase catalytic region of PKN.

Thus, according to the present invention, there is provided a peptide comprising a modified amino acid sequence of Protein Kinase N having the activity to bind to the protein kinase catalytic region of Protein Kinase N, inhibiting the protein kinase activity of Protein Kinase N, and not having the protein kinase activity or derivatives thereof. The modified amino acid sequence may comprise the amino acid sequence 1–540, 1–474, or 39–53 in SEQ ID NO: 1 or a partial sequence thereof having the activity to bind to the protein kinase catalytic region of PKN and inhibiting the protein kinase activity of PKN. Therefore, the peptide having the inhibitory activity against the protein kinase activity of PKN is considered to be useful in elucidating the mechanism of tumorigenesis and metastasis. Furthermore, it is considered to be useful in elucidating the cell signal transduction by PKN.

Peptide Eligible for Phosphorylation

The peptide eligible for phosphorylation according to the present invention is a peptide comprising a modified amino acid sequence of Protein Kinase N eligible for phosphorylation by Protein Kinase N or derivatives thereof. The term "modified amino acid sequence" used herein has the same meaning as described above. Therefore, the partial amino acid sequence of PKN (constituted by a partial sequence of the full amino acid sequence of PKN) eligible for phosphorylation by Protein Kinase N is also an embodiment of the modified amino acid sequences.

In the present invention, the wording "amino acid sequence eligible for phosphorylation by Protein Kinase N" refers to an amino acid sequence which is evaluated by one skilled in the art to be phosphorylated by PKN, for example, amino acid sequences which are evaluated to be phosphorylated by PKN when examined under the same conditions as in Example 9, 10 or 13.

The peptide eligible for phosphorylation does not have the protein kinase activity. In the present invention, the wording "not having protein kinase activity" refers to not having serine/threonine protein kinase catalytic activity of PKN and more specifically refers to the amino acid sequence from 541 onward in SEQ ID No: 1 not having the serine/threonine protein kinase catalytic activity by addition and/or insertion of one or more amino acid sequences and/or by substitution and/or deletion of one or more amino acids and, in the case of a sequence other than that of human being, a sequence corresponding to the above sequence.

Examples of peptides eligible for the phosphorylation according to the present invention include peptides comprising a modified amino acid sequence of human PKN eligible for the phosphorylation by PKN and not having the protein kinase activity. Furthermore, examples thereof include, for example, the amino acid sequence 39–53 in SEQ ID NO: 1 with Ile 46 being substituted by Ser, the amino acid sequence of SEQ ID NO: 2, and modified amino acid sequences thereof (for example, partial sequence) eligible for the phosphorylation by PKN.

The peptide eligible for the phosphorylation by PKN may be a peptide comprising a modified amino acid sequence of the intermediate filament eligible for phosphorylation by Protein Kinase N or derivatives thereof.

Intermediate filaments include vimentin, neurofilament-L, neurofilament-M, neurofilament-H, acidic keratin, neutral keratin, basic keratin, desmin, glia fibrillary acidic protein (GFAP), lamin, and nestin.

The term "modified amino acid sequence" used herein has the same meaning as described above. Therefore, a partial amino acid sequence of the intermediate filament (constituted by a partial sequence of the full amino acid sequence of the intermediate filament) eligible for the phosphorylation by PKN is also an embodiment of the modified amino acid sequences.

Partial amino acid sequences of the intermediate filament include the head-rod domain of vimentin, the head-rod domain of neurofilament-L, the head-rod domain of neurofilament-M, and the head-rod domain of neurofilament-H.

The full amino acid sequences of the intermediate filament exemplified above, for example, the amino acid sequence derived from human being, are known in the art and described in Julien, J. et al., Biochim. Biophys. Acta 909, 10–20 (1987) (neurofilament-L), Myers, M. et al., EMBO J., 6, 1617–1626 (1987) (neurofilament-M), Lees, J., et al., EMBO J., 7, 1947–1955 (1988) (neurofilament-H), and Honore , B., et al., Nucl. Acid. Res., 18, 6692 (1990) (vimentin).

The full amino acid sequence of the intermediate filament derived from a species other than human being (for example, rat, bovine, or xenopus), which is homologous to the sequence of the human intermediate filament, is also included in the wording full amino acid sequence of the intermediate filament used herein.

The peptide eligible for the phosphorylation according to the present invention may be cytoskeletal proteins other than the intermediate filament (for examples, G-actin and caldesmon) and peptides or derivatives thereof comprising modified amino acid sequences thereof.

The origin of the intermediate filament, G-actin, and caldesmon is not particularly limited, and the intermediate filament, G-actin, and caldesmon may be derived from mammals including human being or other origins.

The peptide eligible for phosphorylation according to the present invention is considered to be useful in elucidating the mechanism of tumorigenesis and metastasis. Furthermore, it is considered to be useful in elucidating the mechanism of the cell signal transduction by PKN.

PKN-binding Cytoskeletal Protein

The PKN binding protein according to the present invention comprises a peptide having a modified amino acid sequence of a cytoskeletal protein having PKN binding activity (for example, an intermediate filament or an α-actinin) or derivatives thereof. The term "modified amino acid sequence" used herein has the same meaning as described above. Therefore, a partial amino acid sequence of a cytoskeletal protein (constituted by a partial sequence of the full amino acid sequence of the intermediate filament or α-actinin) having PKN binding activity is also an embodiment of the modified amino acid sequences.

"Intermediate filaments" referred to in the present invention include vimentin, neurofilament-L (NFL), neurofilament-M (NFM), neurofilament-H (NFH), acidic keratin, neutral keratin, basic keratin, desmin, glia fibrillary acidic protein (GFAP), lamin, and nestin.

"α-actinins" referred to in the present invention include skeletal muscle and non-skeletal muscle α-actinins.

In the present invention, the wording "amino acid sequence having PKN binding activity" refers to an amino acid sequence which is evaluated by one skilled in the art to bind to PKN.

Examples of PKN binding cytoskeletal proteins include the head-rod domain of the intermediate filament, spectrin-like repeats and EF-hand-like motifs of α-actinin. Furthermore, examples thereof include a protein comprising the amino acid sequence 1–349 of human-neurofilament-L, a protein comprising the amino acid sequence 1–411 of human-neurofilament-M, a protein comprising the amino acid sequence 423–653, 653–837, or 486–607 of human skeletal muscle type α-actinin, and a protein comprising the amino acid sequence 479–600 or 712–843 of human non-skeletal muscle type α-actinin, and proteins comprising modified amino acid sequences thereof (for example, partial sequences) having PKN binding activity.

The PKN binding cytoskeletal protein has PKN binding activity. Therefore, the PKN-binding protein is considered to be useful in elucidating the mechanism of tumorigenesis and metastasis. Furthermore, it is considered to be useful in elucidating the mechanism of the cell signal transduction by PKN.

Base Sequence

The present invention provides a base sequence encoding the peptide. A typical base sequence of PKN has a part or all of the DNA sequence described in SEQ ID NO: 1. The term base sequence used herein means both a DNA sequence and an RNA sequence.

When the modified amino acid sequence is given, the base sequence encoding the modified amino acid is easily determined, and a variety of base sequences encoding the amino acid sequences described in SEQ ID NO: 1 or 2 can be selected. The base sequence encoding the peptide according to the present invention thus means, in addition to a part or all of the DNA sequence described in SEQ ID NO: 1 or 2, another sequence encoding the same amino acid sequence and containing a DNA sequence of a degenerate codon(s), and also includes RNA sequence corresponding to the DNA sequences.

The base sequence according to the present invention may be either one derived from a naturally occurring source or entirely synthesized one. It may also be one synthesized using a part of a sequence derived from a naturally occurring source. DNAs may be typically obtained by screening a chromosome library or a cDNA library in accordance with a method commonly used in the field of genetic engineering, for example, by screening a chromosome library or a cDNA library with an appropriate DNA probe obtained based on information of the partial amino acid sequence.

Base sequences encoding the activated Rho protein binding protein and the protein inhibiting the binding between the activated Rho protein and PKN include, for example, DNA sequences of bases 55–1656, 55–501, 37–1650, 43–441, 133–369, 256–315, 316–375, and 280–345 in SEQ ID NO: 1.

Examples of base sequences encoding the intermediate filament binding protein include, for example, DNA sequences of bases 37–1656, 373–1656, and 373–1458 in SEQ ID NO: 1.

Examples of base sequences encoding α-actinin binding proteins include, for example, DNA sequences of bases 37–1656, 43–441, 442–1656, and 442–603 in SEQ ID NO: 1.

Examples of base sequences encoding the protein having activity to bind to the catalytic domain of PKN include, for example, DNA sequences of bases 37–1656 and 37–1458 in SEQ ID NO: 1.

Examples of base sequences encoding the peptide inhibiting the protein kinase activity of PKN include, for example, a DNA sequence of bases 151–195 in SEQ ID NO: 1.

Vector and Transformed Host Cell

According to the present invention, there is provided a vector comprising the aforementioned base sequence in such a manner that the vector can be replicable and expresses the protein encoded by the base sequence in a host cell. In addition, according to the present invention, there is provided a host cell transformed by the vector. The host-vector system is not particularly limited. It may express protein fused with other proteins. Examples of the fusion protein expression system include those expressing MBP (maltose binding protein), GST (glutathione-S-transferase), HA (hemagglutinin), histidine (His) repeats, myc, and Fas.

Examples of the vector include plasmid vectors (for example, expression vectors for prokaryotic cells, yeast, insect cells, or animal cells), virus vectors (for example, retrovirus vectors, adenovirus vectors, adeno-associated virus vectors, herpesvirus vectors, Sendai virus vectors, or HIV vectors), and liposome vectors (for example, cationic liposome vectors).

In order to actually introduce a vector into host cells and to express a desired amino acid sequence, the vector according to the present invention may contain, in addition to the base sequence according to the present invention, other sequences for controlling the expression and a gene marker for selecting a microorganism or animal cultured cell. In addition, the vector may contain the base sequence according to the present invention in a repeated form (e.g. tandem). The base sequences may also be introduced in a vector according to the conventional manner, and microorganisms or animal cultured cells may be transformed by the vector based on the method conventionally used in this field.

The vector according to the present invention may be constructed based on the procedure and manner which have been conventionally used in the field of genetic engineering.

Host cells include, for example, *Escherichia coli*, yeasts, insect cells, animal cells (for example, COS cells, lymphocytes, fibroblasts, CHO cells, blood cells, and tumor cells).

The transformed host cells are cultured in an appropriate medium, and the protein or peptide according to the present invention may be obtained from the cultured product. Thus, according to another embodiment of the present invention, there is provided a process for preparing the protein or peptide of the present invention. The culture of the transformed host cells and culture conditions may be essentially the same as those for the cells to be used. In addition, the protein according to the present invention may be recovered from the culture medium and purified according to the conventional manner.

When the cells to be transformed are cancer cells of patients suffering from carcinoma (for example, myelogenic leukemia cells, gastrointestinal cancer cells, lung cancer cells, pancreas cancer cells, ovarian cancer cells, uterine cancer cells, melanoma cells, and cerebral tumor cells), a vector comprising the base sequence according to the present invention may be introduced by a suitable method into cancer cells in an organism including human being to express the protein or peptide according to the present invention, thereby conducting gene therapy for malignant tumors.

For example, it is considered that the expression of a modified amino acid sequence of PKN having the activated Rho protein binding activity and not having protein kinase activity or a modified amino acid sequence of PKN having the inhibitory activity against binding between PKN and the activated Rho protein according to the present invention in an organism including human being causes the activated Rho protein to bind this (i.e., the binding between PKN and the activated Rho protein to be inhibited), resulting in blocked signal transduction from the activated Rho protein to PKN and thus suppressing tumorigenesis and metastasis in which the Rho protein is involved.

Furthermore, the cytoskeletal protein binding proteins, that is, the intermediate filament binding protein and the α-actinin binding protein, can block signal transduction from PKN to the intermediate filament and the α-actinin, respectively and the protein having an activity to bind to the catalytic domain of Protein Kinase N or the peptide having the inhibitory activity against the protein kinase activity of PKN can inhibit the phosphorylation mediated by PKN. As shown in the following description, since the Rho protein is closely involved in the tumorigenesis and metastasis, PKN responsible for signaling in a site downstream of the Rho protein and the cytoskeletal protein responsible for signaling in a site downstream of PKN are considered to be closely involved in the tumorigenesis and metastasis. Therefore, it is considered that the expression of these proteins in an organism including human being can suppress the tumorigenesis and metastasis in which the Rho protein is involved.

Regarding vectors for gene therapy, see "Experimental Medicine(extra edition), Fumimaro Takaku, vol. 12, No. 15, Forefront of Gene therapy (1994)".

Use/Pharmaceutical Composition

It is considered that, as described above, the activated Rho protein binding protein according to the present invention binds to the activated Rho protein (inhibits binding between PKN and the activated Rho protein), enabling blocking of signal transduction from the activated Rho protein to PKN. Furthermore, it is considered, the intermediate filament binding protein and the α-actinin binding protein binds to the regulatory region of PKN, enabling blocking of signal transduction from PKN to the intermediate filament and to α-actinin. Furthermore, the protein having the activity to bind to the catalytic region of PKN and the peptide having the inhibitory activity against the protein kinase activity of PKN can inhibit the phosphorylation mediated by PKN by binding to the catalytic region of PKN.

The activated Rho protein binding protein according to the present invention inhibits the translocation of PKN from cytoplasm to nucleus (see examples described below). Therefore, it is considered that the activated Rho protein binding protein can suppress the cancer gene transcription activity of the Rho protein, inhibiting the tumorigenesis. This will be described as follows.

Firstly, according to Hill, C. S. et al, ibid., lysophosphatidic acid, serum, and stresses such as arsenite and osmotic shock, regulates c-fos transcription through the activation of SRE by SRF. In this case, functional Rho protein is necessary. This suggests an unknown pathway which is located downstream of the Rho protein and responsible for signal transduction.

On the other hand, the present inventors have found that PKN is a target protein of the Rho protein (Examples 1 and 2) and heat shock, sodium arsenite, or serum starvation lead to the translocation of the intracellular distribution of PKN from cytoplasm to nucleus (Examples 19–21). Furthermore, overexpression of PKN-PK⁻ prevents the translocation of even endogenous wild type PKN (Example 22).

Therefore, the activated Rho protein binding protein with the kinase being inactivate or the peptide having the PKN protein kinase inhibitory activity can be used as a dominant negative inhibitor of PKN. In other words, intracellular overexpression of the activated Rho protein binding protein with the kinase activity being inactivated or the kinase domain being deleted or the peptide having PKN protein kinase inhibitory activity enables signal transduction molecules upstream of PKN to be neutralized. This blocks signal transduction (signal transduction to cytoskeleton or to nucleus) in which endogenous wild type PKN is involved. Consequently, the transcriptional activation of an Oncogene by Rho could be inhibited.

Thus, the protein according to the present invention is considered to be useful in inhibiting the tumorigenesis or metastasis.

Therefore, the activated Rho protein binding protein and the peptide having the PKN protein kinase inhibitory activity can be used as a tumorigenesis or metastasis suppressing agent (hereinafter referred to as "an tumorigenesis suppressing agent") in which the Rho protein is involved (that is, tumorigenesis by signal transduction by way of the Rho protein).

Examples of the tumorigenesis and metastasis include tumor formation in which Rho, other small G proteins such as Ras, Rac, Cdc42, and Ral, GDP/GTP exchange proteins for small G proteins (for example, Dbl and Ost), lysophosphatidic acid (LPA), a receptor type tyrosine kinase such as a PDGF receptor or an EGF receptor, a transcription regulating proteins (myc, p53 and the like), or various human tumor viruses are involved.

The tumorigenesis suppressing agent according to the present invention may be administered orally or parenterally (e.g. intramuscular injection, intravenous injection, subcutaneous administration, rectal administration, transdermal administration, nasal administration, and the like), preferably orally. The pharmaceutical agent may be administered to human beings and animals other than human being in a variety of dosage forms suited for oral or parenteral administration.

The tumorigenesis suppressing agents may be prepared in either of preparation forms including oral agents such as tablets, capsules, granules, powders, pills, grains, and troches, injections such as an intravenous injection and an intramuscular injection, rectal agents, fatty suppositories, and water-soluble suppositories depending on their intended uses. These preparations may be prepared according to methods well known in the art with conventional excipients such as fillers, binding agents, wetting agents, disintegrants, surfacactants, lubricants, dispersants, buffering agents, preservatives, dissolution aids, antiseptics, flavors, analgesic agents and stabilizing agents. Examples of the non-toxic additives which can be used include lactose, fructose, glucose, starch, gelatin, magnesium carbonate, synthetic magnesium silicate, talc, magnesium stearate, methylcellulose, carboxymethylcellulose or a salt thereof, acacia, polyethylene glycol, syrup, vaseline, glycerine, ethanol, propylene glycol, citric acid, sodium chloride, sodium sulfite, sodium phosphate, and the like.

The content of the protein according to the present invention in a pharmaceutical agent varies depending on its dosage forms. The pharmaceutical generally contains about 0.1—about 50% by weight, preferably about 1—about 20% by weight, of the protein.

The dose of the protein for the treatment of the tumorigenesis and metastasis may appropriately be determined in consideration of its uses and the age, sex and condition of a patient, and is desirably in the range of about 0.1—about 500 mg, preferably about 0.5—about 50 mg, per day for an adult, which may be administered once or divided into several portions a day.

According to the present invention, there is provided a method for suppressing the tumorigenesis or metastasis, comprising the step of providing the protein or peptide according to the present invention in cells suffering from tumor or cells suspected of metastasis. In this case, the effective dose, administration method, and dosage forms may be the same as those described above in connection with the agent for suppressing tumorigenesis.

The base sequence encoding the protein or peptide according to the present invention may be used in such a manner that a target cell is transformed with the vector having the base sequence encoding the protein or peptide to suppress the tumorigenesis or metastasis. That is, the base sequence may be used as a therapeutic agent for suppressing the tumorigenesis or metastasis.

Screening Method

According to the present invention, there is provided a method for screening a material having an inhibitory activity against the binding between an activated Rho protein and Protein Kinase N, comprising the steps of:

(1) providing a material to be screened in a screening system comprising the activated Rho protein and Protein Kinase N or the activated Rho protein binding protein; and (2) measuring degree of inhibition of binding between the activated Rho protein and Protein Kinase N or the activated Rho protein binding protein.

Examples of the method for "measuring degree of inhibition of binding" include a method for measuring binding between a recombinant PKN and GTPγS.GST-RhoA protein in a cell-free system by using glutathione-Sepharose beads, a method for measuring binding between PKN and the Rho protein in animal cells (cell system) by immunoprecipitation and immunoblotting, a method using a two-hybrid system (M. Kawabata, Experimental Medicine 13, 2111–2120 (1995); and A. B. Vojetk et al., Cell 74, 205–214 (1993)), and a method for measuring degree of inhibition of the Rho protein GTPase activity or enhancement thereof. For example, the degree of inhibition of binding can be measured by the methods described in Example 1, (1) and (2) of Example 4, Example 5, and Examples 16–18. The wording measuring degree of inhibition of binding used herein refers to the determination of the presence or absence of the binding.

The screening system may be either a cell system or a cell-free system. Cell systems used herein include, for example, yeast cells, COS cells, E. coli, insect cells, nematode cells, lymphocytes, fibroblasts (e.g., NIH 3T3 cells, Balb/c3T3 cells, and Rat-1 cells), CHO cells, blood cells, and tumor cells.

Materials to be screened include, but are not limited to, for example, peptides, analogous of peptides, microorganism culture broth, and organic compounds.

The term "screening" used herein includes "assay".

According to the present invention, there is provided a method for screening a material inhibiting the activity of Rho protein GTPase, comprising the steps of:
(1) providing a material to be screened in a screening system comprising the activated Rho protein and activated Rho protein binding protein; and
(2) measuring degree of inhibition of the activity of the Rho protein GTPase.

Furthermore, according to the present invention, there is provided a method for screening a material inhibiting the activity of Rho protein GTPase or the enhancement of the activity, comprising the steps of:
(1) providing a material to be screened in a screening system comprising the activated Rho protein, activated Rho protein binding protein, and Rho protein GTPase activating protein (GAP) in a screening system; and
(2) measuring degree of inhibition of the activity of the Rho protein GTPase of the Rho protein or the enhancement of activity.

Example of the method for measuring "degree of inhibition of the activity of the Rho protein GTPase or the enhancement of the activity" includes a method wherein a reduction in radioactivity of $[\gamma\text{-}^{32}p]$ GTP.GST-Rho in the presence of MBP-PKN (see Example 4) in a cell-free system. For example, the activity of Rho protein GTPase or the enhancement of the activity can be measured according to the method described in Example 18.

Materials to be screened in this aspect of the invention include those described in the above screening method.

According to the present invention, there is provided a method for screening a material inhibiting binding between an intermediate filament and Protein Kinase N, comprising the steps of:
(1) providing a material to be screened in a screening system comprising an intermediate filament and Protein Kinase N or an intermediate filament binding protein; and
(2) measuring degree of inhibition of the binding between the intermediate filament and Protein Kinase N or the intermediate filament binding protein.

Examples of the method for "measuring degree of binding" include a method for measuring binding between a recombinant Protein Kinase N and a recombinant intermediate filament in a cell-free system by using glutathione-Sepharose beads, a method using a yeast two-hybrid system, and a method for measuing the binding between an intermediate filament and PKN in animal cells by immunoprecipitation and immunoblotting. For example, the degree of inhibition of binding may be measured according to the method described in Examples 6 to 8.

The screening system and the material to be screened in this aspect of the present invention include those described above.

Furthermore, according to the present invention, there is provided a method for screening a material inhibiting the polymerization of an intermediate filament, comprising the steps of:
(1) providing a material to be screened in a screening system comprising an intermediate filament and Protein Kinase N or a peptide or derivatives thereof having a modified amino acid sequence of Protein Kinase N and possessing protein kinase activity; and
(2) measuring degree of inhibition of the polymerization of the intermediate filament.

Methods for "measuring degree of inhibition of polymerization" include a method for measuring the binding between head-rod domains of a recombinant intermediate filament in a cell-free line by using glutathione-Sepharose beads (G-Beads). For example, the degree of inhibition of polymerization may be measured according to a method described in Example 10. Furthermore, the wording "measuring the degree of inhibition of polymerization" used herein includes the determination of the presence or absence of the polymerization.

The screening system and the materials to be screened in this aspect of the present invention include those described above.

According to the present invention, there is provided a method for screening a material inhibiting the binding between a skeletal muscle α-actinin and Protein Kinase N, comprising the steps of:
(1) providing a material to be screened in a screening system comprising a skeletal muscle α-actinin and Protein Kinase N or an α-actinin binding protein; and
(2) measuring degree of inhibition of the binding between the skeletal muscle α-actinin and the protein kinase N or α-actinin binding protein.

Furthermore, according to the present invention, there is provided a method for screening a material inhibiting the binding between a non-skeletal muscle α-actinin and Protein Kinase N, comprising the steps of:
(1) providing a material to be screened in a screening system comprising a non-skeletal muscle α-actinin, Protein Kinase N or an α-actinin binding protein, and a calcium ion ($Ca^{2+}$); and
(2) measuring degree of inhibition of the binding between the non-skeletal muscle α-actinin and the Protein Kinase N or the α-actinin binding protein.

Methods for "measuring degree of inhibition of binding" include a method for measuring the binding between a recombinant Protein Kinase N and a recombinant α-actinin in a cell-free system by using glutathione-Sepharose beads, a method using a yeast two-hybrid system, and a method for measuring the binding between an α-actinin and PKN in animal cells by immunoprecipitation and immunoblotting. For example, the degree of inhibition of binding may be measured according to the method described in Examples 24–29.

The screening system and the material to be screened in this aspect of the present invention include those described above.

According to the examples described below, the presence of PI4, 5P2 in the screening system renders the binding between PKN and the α-actinin more strong. Therefore, incorporation of PI4, 5P2 in the screening system is preferred in view of more distinct screening.

According to the present invention, there is provided a method for screening a material inhibiting the activity of Protein Kinase N, comprising the steps of:

(1) providing a material to be screened in a screening system comprising Protein Kinase N or a peptide or derivative thereof having a modified amino acid sequence of the Protein Kinase N and having protein kinase activity; and (2) measuring degree of inhibition of the protein kinase activity of the Protein Kinase N.

Furthermore, according to the present invention, there is provided a method for screening a material inhibiting the activated Rho protein dependent protein kinase activity of Protein Kinase N or the enhancement of the activity, comprising the steps of:

(1) providing a material to be screened in a screening system comprising the activated Rho protein and Protein Kinase N or a peptide or derivative thereof having a modified amino acid sequence of said Protein Kinase N and having the activated Rho protein binding activity and protein kinase activity; and (2) measuring degree of inhibition of the protein kinase activity of the Protein Kinase N or degree of inhibition of the enhancement of the activity.

Methods for measuring "degree of inhibition of the activity of the protein kinase" or "degree of inhibition of the enhancement of the protein kinase activity" include a method for measuring the autophosphorylation activity of Protein Kinase N or the activity of the enzyme, which undergoes a change of activity upon phosphorylation. For example, the degree of inhibition of the protein kinase activity of Protein Kinase N or the degree of inhibition of the enhancement in the activity can be measured according to the method described in Example 3, Example 4 (3), Example 9, Example 10, and Examples 13–15. Furthermore, the wording "measuring the degree of inhibition of the activity of the protein kinase" or "measuring the degree of inhibition of the enhancement of the protein kinase activity" include the determination of the presence or absence of the inhibition of the activity or the enhancement of the activity of the protein kinase.

The degree of inhibition of the protein kinase activity or the degree of the enhancement of the activity is measured using a substrate selected from the group consisting of vimentin, neurofilament-L, neurofilament-M, neurofilament-H, triplet proteins neurofilament (composite of NF-L, NF-M, and NF-H), αPKC peptide, δPKC peptide, the peptide described in SEQ ID NO: 2, caldesmon, and G-actin.

The screening system and the material to be screened in this aspect of the invention include those described in the above screening method.

Methods for measuring "the degree of inhibition of the activity of the protein kinase" or "the degree of inhibition of the enhancement of the protein kinase activity" include a method wherein the translocation of PKN by an immunofluorescence technique or the like. For example, the degree of inhibition of the activity of the protein kinase or the degree of inhibition of the enhancement of the protein kinase activity can be measured according to the method described in Examples 19–21. In this case, the screening system may be a cell system (for example, NIH 3T3 cells, Rat-1 cells, or Balb/c3T3 cells).

As described above, the activated Rho protein has been confirmed to be closely involved in the tumorigenesis and metastasis. Furthermore, the present invention has demonstrated that PKN receives signal transduction from the activated Rho protein. Therefore, it is considered that PKN also is closely involved in the tumorigenesis and metastasis. Thus, the above screening methods can be used as a method for screening a material which can inhibit the tumorigenesis and metastasis.

EXAMPLES

The present invention will be described with reference to the following examples, though it is not limited to these examples only.

In the following examples, the Rho protein is often referred to simply as "Rho," and the RhoA protein is often referred to simply as "RhoA."

Example 1

Purification of Protein Bound to Activated Rho

Figure 1:
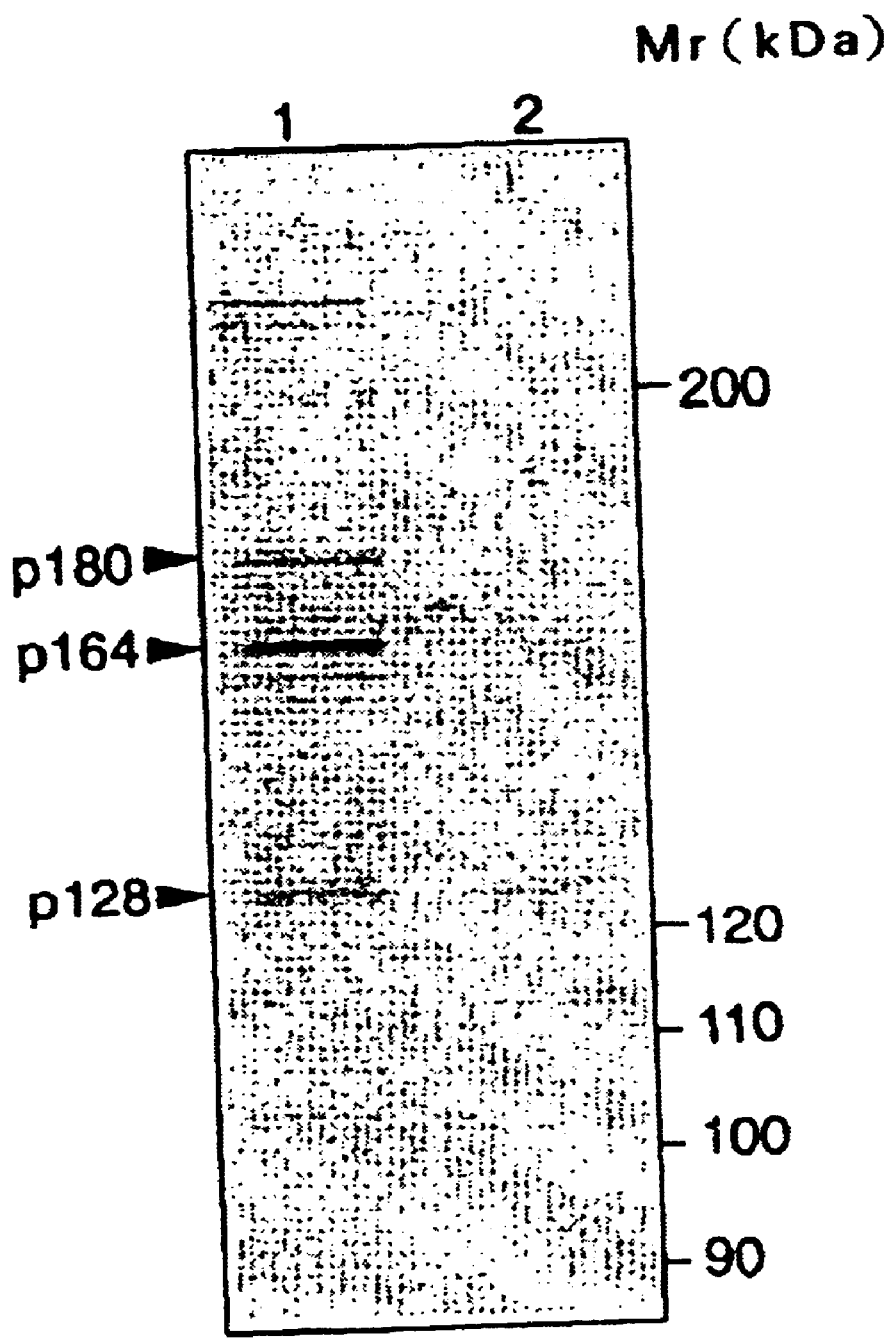
FIG. 1 is an electrophoretic photograph showing the result of purification of p128 by DEAE Sepharose column chromatography.

The crude membrane fraction was prepared from 200 g of bovine brain gray matter. The proteins of the membrane fraction were extracted by addition of an equal volume of homogenizing buffer (25 mM Tris/HCl at pH 7.5, 5 mM EDTA, 1 mM dithiothreitol, 10 mM $MgCl_2$, 10% sucrose) (100 ml) containing 4 M NaCl, and the extract was dialyzed against Buffer A (20 mM Tris/HCl at pH 7.5, 1 mM EDTA, 1 mM dithiothreitol, 5 mM $MgCl_2$). Solid ammonium sulfate was added to a final concentration of 40% saturation. The 0–40% precipitate was dissolved in 16 ml of Buffer A and dialyzed against Buffer A and then passed over a 1 ml glutathione-Sepharose column. One eighth of the pass-through fraction (2 ml) was loaded on a 0.25 ml glutathione-Sepharose column containing 6 nmol of respective GST-small G proteins preloaded with guanine nucleotides as indicated. After washing with 2.5 ml of Buffer A, bound proteins were coeluted with respective GST-small G proteins by addition of 0.825 ml of Buffer A containing 10 mM glutathione. For purification of 128 kD protein (hereinafter referred to as "p128"), the pass-through fraction from the glutathione-Sepharose column was loaded on a 1 ml glutathione-Sepharose column containing 24 nM of GTPγS·GST-RhoA. p128 was eluted by addition of Buffer A containing 0.2 M NaCl. The sample was dialyzed against Buffer A and subjected to a 0.3 ml DEAE Sepharose column equilibrated with Buffer A. After washing with 1.5 ml of Buffer A containing 50 mM NaCl, proteins were eluted with 1.5 ml of Buffer A containing 75 mM NaCl and fractions of 0.3 ml each were collected. Aliquots of fractions (30 μl each) were subjected to SDS-PAGE followed by silver staining. The results are as shown in FIG. 1. They are representative of three independent experiments. p128 appeared as a single peak in fractions 1–3.

GST-RhoA protein and GST-Rac1 used herein were purified according to the procedure described in Shimizu, K. et al., J. Biol. Chem. 269, 22917–22920 (1994) and loaded with guanine nucleotide.

Example 2

Identification of Protein, Bound to Activated Rho, as PKN

Purified p128 was subjected to SDS-PAGE and transferred to a polyvinylidene difluoride membrane. The band corresponding to p128 was digested by lysyl-endo-peptidase (Achromobacter protease I). The resulting peptides were fractionated by C18 column chromatography, and subjected to amino acid sequencing for identification. Five internal sequences from the peptides were obtained. They were in agreement with a part of the sequence of PKN described in SEQ ID NO: 1.

Further, immunoblotting of p128 was carried out by use of anti-PKN antibody (Mukai, H. et al. Biochem. Biophys. Res. Commun. 204, 348–356 (1994)). As a result, a cross-reaction with p128 was observed. The results were as shown in FIG. 2.

Example 3

PKN kinase Activity Dependent Upon Activated Rho

The kinase reaction was carried out in 50 μl of kinase buffer (50 mM Tris/HCl at pH 7.5, 1 mM EDTA, 5 mM $MgCl_2$, 0.06% CHAPS) containing 2 μM [γ-$^{32}$P]ATP (600–800 MBq/mmol) and purified PKN (10 ng of protein) with or without 40 μM αPKC peptide. After incubation for 10 min at 30° C., the reaction mixtures were boiled in SDS-sample buffer and subjected to SDS-PAGE for the autophosphorylation assay. The radiolabeled bands were visualized by autoradiography. The reaction mixtures were spotted onto a Whatman p81 paper for the kinase assay. Incorporation of $^{32}$p into the αPKC peptide was assessed by scintillation counting.

(1) Autophosphorylation of PKN

PKN was autophosphorylated in the presence of various small G proteins (50 pmol each). The results were as shown in FIG. 3.

(2) Dose-dependent Activation by RhoA of PKN Kinase Activity on an αPKC Peptide

The kinase reaction was carried out with 40 μM αPKC peptide in the presence of the indicated doses of GDP.GS T-RhoA or GTPγS.GST-RhoA. The results were as shown in FIG. 4.

(3) Effect of Various Small G Proteins in Kinase Activity of PKN

The kinase reaction was carried out with 40 μM αPKC peptide in the presence of various small G proteins (50 pmol each) or arachidonic acid (2 nmol) as indicated. The results were as shown in FIG. 5. The results shown are representative of three independent experiments.

Example 4

Complex Formation Between PKN and Activated Rho, and Rho-induced Autophosphorylation of PKN in Vivo (1) Complex Formation Between Recombinant PKN and GTPγS.GST-RhoA in a Cell-free System.

The N-terminal region of PKN was made by PCR amplification by the conventional method using primers (SEQ ID NO: 4) (5'-AATTTGGATCCTTGCAGAGTGAGCCTCGCA-3' and (SEQ ID NO: 5) 5'-TATATGGATCCTCAGCCATTGCTGTAGGTCTGGAT-3') with PKN full length cDNA (H. Mukai & Y. Ono, Biochem. Biophys. Res., Commun., 199, 897–904 (1994) used as a template. The N-terminal region of PKN (the amino acid sequence 7–155 in SEQ ID NO: 1) was expressed as MBP fusion protein (hereinafter referred to as "MBP-PKN") and purified by amylose resin (New England Biolab).

MBP-PKN (0.2 nmol) was mixed with 30 μl of glutathione-Sepharose beads containing 0.75 nmol of either GST, GDP.GST-RhoA, GTPγS.GST-RhoA, GTPγS.GST-RhoA$^{AsP38}$, GDP.GST-Rac, GTPγS.GST-Rac, GDP.GST-H-Ras, or GTPγS.GS T-H-Ras in Buffer A (0.75 ml) containing 1 mg/ml of bovine serum albumin. MBP-PKN was eluted by addition of 0.1 ml of Buffer A containing 0.2 M NaCl three times and then by addition of 0.1 ml of Buffer A containing 10 mM glutathione three times. Aliquots (30 μl each) of the first fraction of the glutathione-eluate were subjected to SDS-PAGE followed by silver staining. The results were as shown in FIG. 6.

The N-terminal region of PKN (the amino acid sequence 7–540 in SEQ ID NO: 1) was expressed as MBP fusion protein, and the same experiment as described above was carried out, providing the same results.

(2) Binding between PKN and activated RhoA in COS7 cells.

For assay of complex formation in COS7 cells (ATCC CRL 1651), pMh-PKN7 and pTB701-HA-RhoA or pTB701-HA-RhoA$^{Val14}$ was transfected into COS7 cells, as described in Mukai, H. & Ono. Y, Biochem. Biophys. Res. Commun. 199, 897–904 (1994). After 48 hr, cells were harvested, suspended in a homogenizing buffer (30 mM Tris/HCl at pH 7.5, 0.5 mM $Na_3VO_4$, 5 mM NaF, 2.5 μg/ml leupeptin, 0.05% NP-40, 0.05 M NaCl), and then homogenized in Dounce homogenizer. Each cytosolic extract was subjected to immunoprecipitation by use of anti-HA antibody.

In order to determine the presence or absence of a PKN or RhoA protein, the washed immunoprecipitates and the cytosolic extracts were subjected to SDS-PAGE followed by immunoblotting using anti-PKN antibody and anti-HA antibody. The results were as shown in FIG. 7.

(3) Stimulation of PKN Autophosphorylation by LPA.

Swiss 3T3 cells were cultured in a 35 mm dish and labelled with 0.5 mCi of $^{32}$p or thiophosphate for 2 h. $^{32}$P-labelled Swiss 3T3 cells were stimulated by LPA (200 ng/ml) for 10 min. In order to study the influence of Botulinum C3 exoenzyme, a selective inhibitor of Rho, the cells were treated with Botulinum C3 enzyme (10 μg/ml) as described in Kumagai, K. et al, J. Biol. Chem. 268, 24535–24538 (1993). The cells were then lysed and subjected to immunoprecipitation by use of anti-PKN antibody. The washed immunoprecipitates were subjected to SDS-PAGE for autoradiography. The results were as shown in FIG. 8. Specifically, autophosphorylation of PKN in Swiss 3T3 cells was stimulated twice by LAP and blocked by Botulinum C3 exoenzyme. The results shown are representative of three independent experiments.

Example 5

Assay of Binding Between Rho and PKN in Yeast Two-hybrid System

According to a method described in A. B. Vojetk et al. Cell 74, 205–214 (1993), wild type H-Ras, wild type RhoA with C-terminal CAAX structure removed (S. Ando et al. Jikken Igaku 11, 1973–1980 (1993)), and variant RhoA$^{Val14}$cDNA fragment, were introduced into pBTM116 vector (A. B. Vojetk et al, ibid.) to construct vectors (designated as pBTM116-RasWT, pBTM116-RhoWT, and pBTM116-Rho$^{Val14}$), for expression thereof and LexA as fusion protein in yeast cells, which were then transformed into yeast (strain L40).

cDNA in N-terminal region (the amino acid sequence 7–155 in SEQ ID NO: 1) of PKN was introduced into BamHI site of pACT vector (MATCHMAKER Library Kit, manufactured by Clontech Laboratories, Inc.) to construct a vector (designated as pACTIIHK-PKN-N) for expression thereof and GAL4 as fusion protein in yeast cells. The cDNA fragment, used here, corresponding to the N-terminal region of PKN was prepared as described in Example 4 (1).

Yeast transformed with pBTM116-RasWT, pBTM116-RhoWT, and pBTM116-Rho$^{Val14}$ was further transformed with pACTIIHK-PKN-N. Transformants were screened based on histidine requirement (A. B. Vojetk et al, Cell 74, 205–214 (1993).

As a result, as shown in FIG. 9, it was found that the N-terminal region (amino acids 7–155) of PKN binds to both wild type RhoA and variant RhoA$^{Val14}$.

Example 6

Isolation of PKN-Binding Protein Using Yeast Two-Hybrid System

The yeast two-hybrid system was used to identify proteins that interact with N-terminal region of human PKN, The chimeric protein used contained the DNA-binding domain of the GAL4 protein fused to the N-terminal region of human PKN. Specifically, EcoRI/BamHI fragment encoding the amino acid sequence 1–540 in SEQ ID NO: 1 (this domain being hereinafter referred to as "PKNN1") of PKN was inserted into the vector pGBT9 (Clontech Laboratories). This vector directs the expression of a fusion protein between the DNA-binding domain (the amino acid sequence 1–147) of Gal4 and the N-terminal regulatory region of PKN from a crippled ADH promoter. This plasmid, which contains a TRP1 marker, was cotransfected with the human brain cDNA library (Clontech Laboratories, Inc.; Each plasmid contains LEU2 marker.) into the yeast strain YGH1 (a, ura3-52, his3-200, ade2-101, lys2-801, trp1-901, leu2-3, Can$^r$, gal4-542, gal80-538, LYS2::gall$_{uas}$-gall$_{tata}$-HIS3, URA3::gall-lacZ). Transformants were plated on yeast dropout media lacking leucine, tryptophan, and histidine and containing 10 mM 3-amino-1,2,4,triazole (3-AT).

About 1×10$^6$ transformants were analyzed. After 7–14 days of growth, HIS+ colonies were scored for β-galactosidase activity as follows: Colonies (or patches derived from the original positive colonies) were picked up from plates directly onto Hybond-N nylon membrane (Amersham), quickly frozen in liquid nitrogen (about 40 sec), and immediately overlaid onto Whatman 3MM filters that had been soaked in β-galactosidase assay buffer (60 mM Na$_2$HPO$_4$, 60 mM NaHPO$_4$, 10 mM KCl, 1 mM MgSO$_4$, 5 mM DTT, 0.01% 5-bromo-4-chloro-3-indolyl-β-D-galactopyranoside (X-gal)). Filters were placed in dishes and incubated at 30° C. Plasmid DNA was recovered from positive colonies and introduced by electroporation into *E. coli* HB101. Primary positive clones were retransfected into original yeast host strains in combination with the Gal4 DNA-binding domain-PKN or the Gal4 DNA-binding domain-p53 tumor suppressor protein. Library plasmids that activated marker expression only in the presence of PKN were analyzed further. The 82 plasmids were isolated representing 16 different cDNAs as judged by DNA sequencing. As a result of base sequencing, one of these cDNAs was found to encode the head-rod domain of NFL protein.

Example 7

Binding Assay for Characterizing Interaction Between PKN and Various NFs in Yeast Two-Hybrid System Specificity of the interaction between PKN and various NFs was investigated by measuring the ability of the two-hybrid constructs, pBTM116(Vojtek, A. B. et al., Cell, 74, 205–214 (1993)) (instead of pGBT9)-PKN and pVP16 (Vojtek, A. B. et al., Cell, 74, 205–214 (1993)) (instead of pGAD10)-NF or in reverse, to support lacZ expression in L40 cells. The results have revealed a specific interaction between the N-terminal region of PKN and the head-rod domain of each subunit (NFL, NFM, and NFH) of NF. Scheme of the fusion gene construct for each subunit of NF used by the present inventors was as shown in FIG. 10.

Yeast expression vectors were prepared as follows. Yeast expression vector pVP/NFL#21 for the VP16 transcription activation domain-head-rod domain of human NFL was made by subcloning a EcoRI insert (amino acid sequence 1–349) of a library plasmid #21 originally isolated from two-hybrid screening into pVP16 vector (Vojtek, A. B. et al., Cell, 74, 205–214 (1993)). Yeast expression vectors for the VP16 transcription activation domain—tail domain of NFL and NFH or the VP16 transcription activation domain—head-rod domain or tail domain of NFM were constructed by subcloning BamHI/NotI insert of pGST/NFLt, pGST/NFHt, pGST/NFMhr, and pGST/NFMt (described in Example 8) into pVP16 in frame, respectively (designated respectively as pVP/NFLt, pVP/NFHt, pVP/NFMhr, and pVP/NFMt). Expression vector pVP/NFHf for VP16-full length of NFH fusion protein was constructed by digesting pBH, a plasmid containing the entire coding region of NFH in pBluescript II SK vector (available from Strantagene), with BglII and the fulllength cDNA insert was subcloned into pVP16. Expression vector pVP/NFHhr for the VP16-head-rod domain of NFH fusion protein was made by digesting pVP-NFHf with Tth111I/EcoRI and filling in the ends with T4 DNA polymerase and ligating them together with T4 DNA ligase. This removed the DNA sequences C-terminal of the Tth111I site which encodes the tail domain of NFH. Yeast expression vector pBTM/NFL#21 or pBTM/NFLt for the LexA DNA binding domain-head-rod domain of NFL or -tail domain of NFL was constructed as described above except for using pBTM116 (Vojtek, A. B. et al., Cell, 74, 205–214 (1993)) instead of pVP16. Expression vector pBTM/or pVP/PKNN1 for LexA- or VP16-PKNN1 was constructed by subcloning EcoRI/BamHI fragment (the amino acid sequence 1–540 in SEQ ID NO: 1) of human PKN into pBTM116 or pVP16. Expression vector pBTM/or pVP/PKNC1 for LexA- or VP16- C-terminal region of PKN (the amino acid sequence 511–942 in SEQ ID NO: 1, this region was designated as "PKNC1") was constructed by subcloning ClaI/EcoRI fragment of human PKN into pBTM116 or pVP16.

Figure 11:
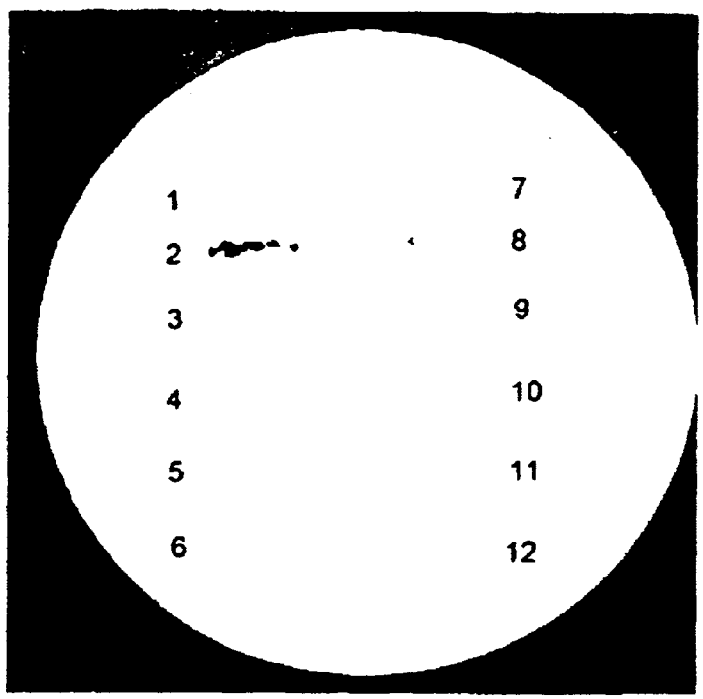
Figure 11:
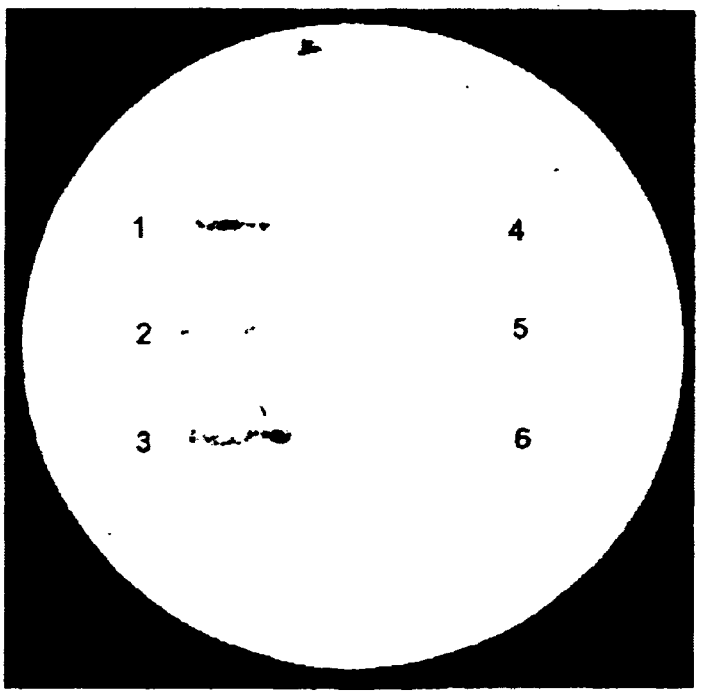

FIG. 11 (A) shows a specific interaction between the N-terminal region of PKN and the head-rod domain of NFL. To determine whether N-terminal region of PKN binds to NFM or NFH as well as NFL, corresponding region to the head-rod domain of NFM or NFH was ligated to pVP16 and lacZ expression was measured in two-hybrid system. The N-terminal region of PKN bound to each head-rod domain of NF subunit (FIG. 11(B)), and also interacted with the corresponding head-rod domain of vimentin, a ubiquitously expressed member of intermediate filament, in two-hybrid system (data not shown).

Example 8

Binding Assay for Characterizing Interaction Between in vitro Translated PKN and GST-NF (Each Sub-unit) Fusion Protein To further characterize the interaction between PKN and NF, the present inventors tested the ability of in vitro translated PKN to bind to GST-NFL, GST-NFM, GST-NFH, or GST alone in an in vitro binding assay.

(1) Preparation of PKN By in vitro Translation

For in vitro transcription, truncated human PKN was made as follows; Expression vector pPKNN2 for N-terminal region of PKN (the amino acid sequence 1–474 in SEQ ID NO: 1, this region was designated as "PKNN2") was made by digesting phPKN-H4 (a plasmid containing human PKN cDNA in pBluescript II SK (Mukai, H. & Ono, Y., Biochem. Biophys. Res. Commun. 199, 897–904 (1994)) with Bst EII, and filling in the ends with T4 DNA polymerase, and self-legation. This removed the original amino acid sequences C-terminal downstream of the BstEII site (1425 nucleotides from initiating ATG codon), and a stop codon was created in the plasmid sequence. Fragment coding for the amino acid sequence 614–942 in SEQ ID NO: 1, (This region was designated as "PKNC2") containing the conserved catalytic domain of human PKN was made by PCR amplification. Expression vector pPKNC2 was made by subcloning this fragment into pRc/CMV (Invitfrogen Corp.). These plasmids were linealized by cutting with XbaI, and CRNA was transcribed using T7 RNA polymerase. For NFL, pBL (Nakagawa, T. et al., J. Cell. Biol. 129, 411–429 (1995)) was linealized by cutting with HindIII, and CRNA was transcribed using T3 RNA polymerase. For in vitro translation, these cRNAs were translated in rabbit reticulocyte lysate (Promega) in the presence of [$^{35}$S] methionine.

(2) Preparation of GST Fusion Proteins

Expression vector pGST/NFL#21 for GST-NFL#21 (the amino acid sequence 1–349 of human NFL) was made by subcloning a EcoRI insert of the plasmid #21 into pGEX4T vector (Pharmacia Biotech). Expression vector pGST/NFLdelA for GST/NFLdelA (the amino acid sequences 1–175 and 335–349 of human NFL) was made by digesting a pGST/NFL#21 with PstI, and removing the 480 bp fragment, and self-ligating with T4 DNA ligase. Expression vector pGST/NFLdelB for GST-NFLdelB (the amino acid sequence 245–349 of human NFL) was made by subcloning BglII/EcoRI fragment of pGST/NFL#21 into pGEX4T vector. Expression vector pGST/NFLt for the GST-tail domain of NFL fusion protein was made by subcloning an about 700 bp KpnI-EcoRI fragment of pBL into pGEX4T vector. Expression vector pGST/NFMhr for the GST-head-rod domain (the amino acid sequence 1–411 of human NFM) fusion protein was made by PCR amplification from human hippocampus cDNA library and subcloning into pGEX4T vector. Expression vector pGST/NFLf for GST-full length of NFL was constructed by subcloning BamHI/EcoRI insert of pBL into pGEX4T vector. Expression vector pGST/NFMt for the GST-tail domain of NFM fusion protein was made by subcloning an about 1.0 kbp XhoI-NotI fragment of pBM (Nakagawa, T. et al., J. Cell. Biol. 129, 411–429 (1995)) into pGEX4T vector. Expression vector pGST/NFHf for GST-full length of NFH fusion protein was constructed by digesting pBH (Nakagawa, T. et al., J. Cell. Biol. 129, 411–429 (1995)) with BglII and insertion fragment was subcloned into BamHI restriction site of pGEX4T. Expression vector pGST/NFHhr for the GST-head-rod domain of NFH fusion protein was made by digesting pGST/NFHf with Tth111I/EcoRI and filling in the ends with T4 DNA polymerase and ligating them together with T4 DNA ligase. This removed the DNA sequences C-terminal of the Tth111I site which encodes the tail domain of NFH. Expression vector pGST/NFHt for the GST-tail domain of NHF fusion protein was made by digesting pBH with Tth111I/BglII and filling the ends, and subcloning an about 2 kbp fragment into pGEX4T.

Expression of GST or GST fusion proteins was induced with 0.1 mM IPTG. Cells were centrifuged at 5000×g for 5 min, and the resultant pellet was resuspended in GST lysis buffer (50 mM Tris/HCl at pH8.0, 1 mM EDTA, 1 µg/ml leupeptin, 1 mM DTT, 1 mM PMSF) containing 1% Triton X-100 with/without 1 M urea. And the cells were lysed by sonication. Cell debris was removed by centrifugation (30000×g for 10 min), and the supernatant was added to Glutathione-Sepharose 4B (Pharmacia Biotech Inc.). The Sepharose 4B was washed with 40 column volumes of GST lysis buffer. The GST and GST fusion proteins were eluted with GST elution buffer (100 mM Tris/HCl at pH 8.0, 20 mM Glutathione, 120 mM NaCl, 1 mM EDTA, 1 mM DTT, 1 µg/ml leupeptin) containing or not containing 1 M urea. The eluate was dialyzed overnight against 10 mM Tris/HCl (pH 8.8) containing 1 mM EDTA, 1 mM DTT, and 0.1 µg/ml leupeptin.

(3) in vitro Binding Assay

For in vitro NF binding experiment, 2.5 µl of in vitro translated PKNN2 or PKNC2 was mixed with 5 µg of each GST-NF fusion protein or 25 µg of GST alone in 400 µl of GST binding buffer (20 mM Tris/HCl at pH 7.5, 0.5 mM DTT, 150 mM NaCl, 0.05% Triton-X100, 1 mM EDTA, 1 µg/ml leupeptin) and incubated for 1 hr at 4° C. Twenty five µl of Glutathione-Sepharose 4B pretreated with 10 mg/ml of E. coli extract to block non-specific binding, was then added, and the binding reactions were then carried out while rotating for an additional 30 min at 4° C. The Glutathione-Sepharose 4B was then washed three times in GST wash buffer (20 mM Tris/HCl at pH 7.5, 0.5 mM DTT, 1 mM EDTA, 1 µg/ml leupeptin) containing 0.5 M NaCl and 0.5% Triton X-100 and further washed with GST wash buffer. Bound proteins were eluted with GST elution buffer and subjected to 10% SDS-PAGE electrophoresis. Quantitation of the binding reactions was carried out by a FUJI BAS1000 bio-imaging analyzer.

The results are shown in FIG. 12. As can be seen from the drawing, the N-terminal region of PKN bound to the head-rod domain of NFL and little binding was observed between the C-terminal catalytic domain of PKN and the head-rod domain of NFL in the in vitro binding assay. Furthermore, the ability of in vitro translated PKN to bind to GST-NF (each subunit) fusion proteins, and revealed that PKN directly bound to each subunit of NF at the head-rod domain in vitro (FIG. 13).

As indicated in Examples 4 and 5, Rho binds to N-terminal region (the amino acid sequence 7–155 in SEQ ID NO: 1) of PKN. On the other hand, the head-rod domain of NF binds to N-terminal regulatory region (the amino acid sequence 1–540 or 1–474 in SEQ ID NO: 1) of PKN. Therefore, there is a possibility that the head-rod domain of NF and Rho might compete for binding to Rho-binding domain of PKN. To investigate this, studies were made on the competition of RhoA and NFL for binding to the N-terminal region (the amino acid sequence 1–540 in SEQ ID NO: 1) of PKN in an in vitro assay. As a result, bacterially synthesized NFL did not compete with bacterially synthesized RhoA for binding to the N-terminal region of PKN (data not shown). From this, it has been found that the NF-binding region within the N-terminal regulatory region of PKN is present in a region different from the Rho-binding region (the amino acid sequence 33–111 in SEQ ID NO: 1) (Example 16). That is, the NF-binding region was estimated to be included in the amino acid sequence 1–32 or 112–540 in SEQ ID NO: 1. Furthermore, as described above, the amino acid sequence 1–474 in SEQ ID NO: 1 also bound to NF, and, hence, the NF-binding region was estimated to be included in the amino acid sequence 1–32 or 112–474 in SEQ ID NO: 1.

Example 9

Phosphorylation of NF by PKN (1) Phosphorylation of Native NF by PKN

To test the ability of PKN to phosphorylate each subunit of NF, NF was purified from spinal cord and subject to in vitro phosphorylation by PKN.

Native NFs were prepared from bovine spinal cords according to a method described in Hisanaga, S. & Hirokawa, N., J. Mol. Biol. 202, 297–305 (1988). Kinase assay was carried out according to the following method.

Soluble cytosolic extract of spinal cord or purified NF proteins were boiled for 5 min to destroy endogenous protein kinase activity prior to their use as phosphate acceptors. The phosphorylation of NF preparations was carried out at 30° C. in an assay mixture containing 20 mM Tris/HCl at pH 7.5, 8 mM $MgCl_2$, 100 μM ATP, 185 kBq of [$\gamma$-$^{32}$P] ATP, each subunit of NF, 20 ng/ml of purified PKN from rat testis, and with/without 40 μM arachidonic acid as indicated in each experiment. Reactions were terminated after various times by the addition of an equal volume of Laemli's sample buffer, and separation was performed on 7% SDS-PAGE. The gels were dried under vacuum and exposure to BAS1000 bio-imaging analyzer. Dephosphorylation of NF proteins was conducted with calf intestine alkaline phosphatase according to a method described in Carden, M. J. et al., J. Biol. Chem. 260, 9805–9817 (1985) and terminated after boiling for 5 min.

The results were as shown in FIGS. 14–18. PKN was able to phosphorylate efficiently all three NF subunits.

Initial velocity of phosphorylation of each subunit by PKN was about 5–10 times higher in the presence of arachidonic acid than in the absence of it (FIG. 14). In the presence of arachidonic acid, phosphate incorporation into NF subunits reached a maximum about 60 min after the initiation of the reaction and then continued in the plateau state to 120 min (FIGS. 15 and 16). Although purified PKN was labile in its diluted state, it was unlikely that the decline in phosphorylation speed was mainly due to the inactivation of PKN, because phosphorylation level was not so decreased from 60 min to 120 min in the absence of arachidonic acid (data not shown). As estimated for this experiment by image quant, the extent of maximal phosphorylation by PKN per mol subunit of protein was about 2 mol/mol of NFH, about 6 mol/mol of NFM, and about 1 mol/mol of NFL, respectively. The NFH, which was reported to be the most intensely radiolabeled subunit in vivo (Sihag, R. K. & Nixon, R. A. J. Biol. Chem. 264, 457–464 (1989)), was poorer substrate for PKN in vitro than NFM.

Since NFH and NFM in this assay were already partially phosphorylated, the possibility was raised that potential PKN phosphorylated sites have been masked. Therefore, enzymatically dephosphorylated NF was used to determine the presence of additional phosphorylation sites. As shown in FIG. 15, the electrophoretic mobility changed accompanying dephosphorylation of NFH and NFM (Carden, M. J. et al., J. Biol. Chem. 260, 9805–9817 (1985)). Dephosphorylation of bovine NF with alkaline phosphatase did not result in any significant difference in phosphorylation of the NFH and NFM subunits by PKN, suggesting that native NF contains sites that are accessible to phosphorylation by PKN (FIGS. 15 and 16).

(2) Phosphorylation of Recombinant NF by PKN To identify the region containing the phosphorylation site of NF by PKN, GST-head-rod and -tail domain of each subunit of NFs were bacterially synthesized (Example 8), and subjected to in vitro phosphorylation assay in the same manner as described above. As shown in FIG. 17, $^{32}$p was incorporated to each GST-head-rod domain of NF to the extent 3:10:2 for NFH:NFM:NFL. The GST-tail domain of each subunit was not labeled at all. PKN also phosphorylated the GST-head-rod domain of vimentin (data not shown). This clearly indicated that phosphorylation sites were located exclusively in the head-rod domain of these intermediate filaments.

Example 10

Effects of Phosphorylation on the Filament Structure (Polymerization) of NFL in vitro It is widely accepted that the NFL subunit forms the "core" of the NFs, suggesting that NFL may assemble first and may then provide the signal as well as the scaffold for co-assembly or polymerization of NFM and NFH subunits. It has been shown in vitro that phosphorylation of NFL by the PKA and PKC inhibited its polymerization and also depolymerized filaments (Gonda, Y. et al., Biochem. Biophys. Res. Commun. 167, 1316–1325 (1990); Nakamura, Y. et al., Biochem. Biophys. Res. Commun. 169, 744–750 (1990); Hisanaga, S. & Hirokawa, N., J. Mol. Biol. 211, 871–882 (1990). Then investigation was made on whether NFL polymerized using an in vitro binding analysis.

The bacterially produced GST-head-rod domain of NFL or -full length NFL fusion protein was mixed with in vitro translated [$^{35}$S]-labeled NFL in a buffer at pH 8.5 with 1 mM $MgCl_2$, then shifted pH of the reaction mixture to 7.2, and incubated for 1 hr at 35° C. After extensive washing, proteins bound to the beads were analyzed by autoradiography. As shown in FIG. 18, polymerization of NFL was detected (lanes 6 and 8).

Next, whether phosphorylation of NFL by PKN inhibits the polymerization of NFL in this assay system was determined. After the GST-head-rod domain of NFL or -full length of NFL were phosphorylated by PKN, transferred to the reaction mixture and mixed with in vitro translated NFL. More detailed procedure was as follows.

For in vitro NF polymerization experiment, phosphorylated or non-phosphorylated form of bacterially synthesized GST-NFL or GST-NFL#21 was prepared by incubation of 5 μg of these proteins with 1 mM $MgCl_2$, 60 ng of PKN with/without 100 μM ATP at 30° C. for 2 hr. In vitro translated NFL was incubated with the above mixtures or 25 μg of GST in depolymerization buffer (20 mM Tris/HCl at pH 8.5, 1 mM DTT, 1 μg/ml leupeptin) with 1 mM $MgCl_2$, then shifted pH of the reaction mixture to 7.2 by addition of an appropriate volume of 1 M PIPES (pH 6.8), and incubated for 1 hr at 35° C. Twenty five μl of Glutathione-Sepharose 4B, pretreated with 10 mg/ml of E. coli extract to block non-specific binding, was then added, and the binding reactions were then performed while rotating for an additional 30 min at 4° C. The Glutathione-Sepharose 4B was then washed twice in a depolymerization buffer containing 0.5% Triton-X100, and further washed with depolymerization buffer. Bound proteins were eluted with GST elution buffer and subjected to 10% SDS-PAGE. Quantitation of the binding reactions was carried out by a FUJI BAS1000 bio-imaging analyzer.

As shown in FIG. 18, after the phosphorylation by PKN, the binding of GST-head-rod domain of NFL or -full length of NFL to in vitro translated NFL was hardly detected (lanes 7 and 9), indicating that phosphorylation of NFL by PKN inhibited the polymerization of NFL.

Example 11

Detection of Interaction of the Amino-terminal Region of PKN with the Carboxyl-terminal Region in the Yeast Two-hybrid System

To study a possibility that the catalytic region is masked with the regulatory region (the catalytic region binds to the regulatory region), the yeast two-hybrid assay was carried out. The construction of the two-hybrid system for this purpose was carried out as follows.

The plasmid pBTM/PKN-N, for expression of the fusion protein of DNA binding domain of LexA and the amino-terminal region of PKN (the amino acid sequence 1–540 in SEQ ID NO: 1), were constructed by subcloning an EcoR1/BamH1 fragment of human PKN cDNA into pBTM116 (Vojetk, A. B. et al., Cell 74, 205–214(1992)). The plasmid pVP/PKN-N for expression of the fusion protein of transcription activation domain pVP16 and the amino-terminal region of PKN (the amino acid sequence 1–540 in SEQ ID NO: 1) was constructed by subcloning a EcoR1/BamH1 fragment of human PKN into pVP16 (Vojetk, A. B. et al., Cell, 74, 205–214 (1993)). pBTM/PKN-C and pVP/PKN-C were constructed by subcloning a ClaI/EcoRI fragment of human PKN cDNA encoding its carboxyl-terminal region (the amino acid sequence 511–942 in SEQ ID NO: 1) into pBTM116 and pVP16, respectively. Yeast L40 cells were cotransfected with the expression plasmid encoding a fusion protein of the LexA DNA binding domain and the fragment of PKN (pBTM/PKN-N or pBTM/PKN-C) and the expression plasmid encoding a fusion protein of VP16 transcription activation domain and the fragment of PKN (pVP/PKN-N or pVP/PKN-C). Interaction was examined using a filter lift assay for β-galactosidase activity (Fields, S. & Song, O. Nature 340, 245–246 (1989).

As shown in FIG. 19, it was confirmed that β-glucosidase was expressed in yeast cells cotransfected with the vector for expressing the amino-terminal region of PKN (pBTM/PKN-N or pVP/PKN-N) and the vector for expressing the carboxyl-terminal region of PKN (pVP/PKN-C or pBTM/PKN-C) (FIGS. 19 (4) and (5)). Namely, the interaction between the regulatory region (amino-terminal region) of PKN and the catalytic region (carboxylterminal region) was substantiated.

Example 12

Detection of Interaction of the Regulatory Region (Amino-terminal Region) of PKN with the Catalytic Region Carboxyl-terminal Region) in vitro

To confirm the interaction between the regulatory region (amino-terminal region) and the catalytic region (carboxyl-terminal region) of PKN, an in vitro binding assay using GST fusion proteins and in vitro translated $^{35}$S-labeled proteins was carried out by the following method.

(1) in vitro Transcription and Translation:

Truncated human PKN was made as follows; expression vector pPKN-N for amino-terminal region of PKN was made by digesting phPKN-H4 (human PKN cDNA inserted in pBluescript II SK) (Mukai, H. & Ono, Y., Biochem. Biophys. Res. Commun. 199, 897–904 (1994)) with BstEII, and filling-in both the ends with T4 DNA polymerase, and self-ligation. The resulting plasmid codes for amino acid residues of PKN from 1 to 474 in SEQ ID NO: 1. cDNA insert from this plasmid was cloned into pRc/CMV (Invitrogen Corp.). Fragment coding for the amino acids 614–942, in SEQ ID NO: 1, containing the catalytic domain of human PKN was made by PCR amplification. Expression vector pPKN-C for the carboxyl-terminal region of PKN was made by subcloning this fragment into pRc/CMV. These plasmids were linearized by cutting with XbaI, and cRNA was transcribed using T7 RNA polymerase. cRNA was translated in a chicken reticulocyte lysate (Promega) in the presence of [$^{35}$S] methionine.

(2) Preparation of GST Fusion Proteins:

pGST/PKN-N for expression of the fusion protein of GST and the amino-terminal region of PKN (the amino acid sequence 1–540 in SEQ ID NO: 1) was made by subcloning a BamH1 insert of the phPKN-H4 into pGEX4T vector (Pharmacia Biotech Inc.). pGST/PKN-C for expression of the fusion protein of GST and the carboxyl-terminal region (the amino acid sequence 634–942 in SEQ ID NO: 1) was made by subcloning an EcoRI insert of the phPKN-H4 into pGEX4T vector. Expression of GST or GST fusion proteins was induced with 0.1 mM IPTG. Cells were centrifuged at 5,000×g for 5 min, and the resultant pellet was resuspended in GST lysis buffer [50 mM Tris/HCl (pH 8.0), 1 mM EDTA, 1 μg/ml leupeptin, 1 mM DTT, 1 mM PMSF] containing 1% Triton X-100. The cells were lysed by sonication. Cell debris were removed by centrifugation at 30,000×g for 10 min, and the supernatant was added to glutathione-Sepharose 4B (Pharmacia Biotech Inc.). The resin was washed with 40 column volumes of GST lysis buffer. The GST and GST fusion proteins were eluted with GST elution buffer [100 mM Tris/HCl (pH 8.0), 20 mM glutathione, 120 mM NaCl, 1 mM EDTA, 1 μg/ml leupeptin, 1 mM DTT]. The eluate was dialyzed overnight against 10 mM Tris/HCl (pH 8.0) containing 1 mM EDTA, 1 mM DTT, and 0.1 μg/ml leupeptin.

(3) in vitro Binding Assay:

In vitro translated PKN-N or PKN-C (2.5 μl) was mixed with 5 μg of each GST-PKN-N or GST-PKN-C fusion protein or 25 μg of GST alone in 400 μl of GST binding buffer [20 mM Tris/HCl (pH 7.5), 0.5 mM DTT, 150 mM NaCl, 0.05% Triton X-100, 1 mM EDTA, 1 μg/ml leupeptin] and incubated for 1 hr at 4° C. Twenty five μl of glutathione-Sepharose 4B pretreated with 10 mg/ml of E. coli extract to block nonspecific binding, was then added, and the binding mixtures were then rotated for an additional 30 min at 4° C. The glutathione-Sepharose 4B was then washed three times in GST wash buffer [20 mM Tris/HCl (pH 7.5), 0.5 mM DTT, 1 mM EDTA, 1 μg/ml leupeptin] containing 0.5 M NaCl and 0.5% Triton X-100 and further washed with GST wash buffer. Bound proteins were eluted with GST elution buffer and subjected to 10% SDS-PAGE. Quantification of the binding reactions was carried out by a BAS 1000 bio-imaging analyzer (FUJI).

As a result, the interaction between the regulatory region (amino-terminal region) of PKN and the catalytic region (carboxyl-terminal region) was confirmed also by the in vitro binding assay using the GST fusion proteins and the in vitro translated $^{35}$S-labelled proteins (FIG. 20, lanes 6 and 8). The above results show that the amino-terminal regulatory region of PKN directly binds to the carboxyl-terminal catalytic region.

Example 13

Phosphorylation of the [Ser$^{46}$] PKN (39–53) Peptide by PKN

[Ser$^{46}$] PKN (39–53) peptide (corresponding to the amino acid sequence 39–53 in SEQ ID NO: 1, substituting Ser for Ile; (SEQ ID NO: 2)RERLRRESRKELKLK) was synthesized with an automated peptide synthesizer (Applied Biosystems, model 403A), and studies were made on the phosphorylation of the peptide by PKN.

Kinase assay was carried out by the following method. The purified PKN (1 ng) from rat testis cytosol (Kitagawa, M. et al., Biochem. J. 310, 657–664. (1995)) was incubated for 5 min at 30° C. in a reaction mixture (final volume 25 μl) containing 50 mM Tris/HCl (pH 7.5), 8 mM Mgcl$_2$, 20 μM ATP, 18.5 kBq of [γ-$^{32}$p] ATP, 40 μM arachidonic acid, phosphate acceptors and inhibitors as indicated in each experiment. Reactions were started by the addition of the enzyme source and terminated by spotting them onto Whatman P81 papers immersed in 75 mM phosphate. Incorporation of $^{32}$P into phosphate acceptors was assessed by liquid scintillation counting. The results were as shown in FIG. 21.

The peptide [Ser$^{46}$] PKN (39–53) was found to act as a substrate for PKN and to have a Km of approximately 25 μM and a Vmax of 400 nmoles/min/mg of protein. In FIG. 21, a double-reciprocal plot of the data is shown. The results are means±S.E. from three independent experiments performed in duplicate.

Example 14

Inhibition of Protein Kinases Activity of PKN with Synthetic Peptides

As described in Examples 11 and 12, the amino-terminal region (the amino acid sequence 1–540 or 1–474 in SEQ ID NO: 1; hereinafter often referred to as "regulatory region") of PKN bound to the carboxyl-terminal region (the amino acid sequence 511–942, 614–942 or 634–942 of SEQ ID NO: 1; hereinafter referred to as "catalytic region"), indicating that the regulatory region of PKN contains a sequence capable of binding to the catalytic region. In the present example, the pseudosubstrate-like sequence was synthesized to study the inhibitory effect of the synthetic peptide on protein Kinase activity.

The following substrate peptides and pseudosubstrate-like peptides of PKN were synthesized according to the amino acid sequences of rat.PKC (Ono, Y. et al., J. Biol. Chem. 263, 6927–6932 (1988)) and human PKN (Mukai, H. & Ono, Y. Biochem. Biophys. Res. Commun. 199, 897–904 (1994), respectively, with an automated peptide synthesizer (Applied Biosystems, model 403A):.PKC peptide (corresponding to the amino acid sequence 137–153 of PKC, substituting Ser for Ala; (SEQ ID NO: 6)AMFPTMNRRGSIKQAKI); PKN (39–53) peptide (corresponding to the amino acid sequence 39–53 in SEQ ID NO: 1; (SEQ ID NO: 2) RERLRREIRKELKLK); and PKN (54–73) peptide (corresponding to the amino acid sequence 54–73 in SEQ ID NO: 1; EGAENLRRATTDLGRSLGPV) (portion of SEQ ID NO: 1).

The protein kinase assay was carried out in the same manner as in Example 13, except that PKN was measured by using 6PKC peptide as a substrate and PKN (39–53) peptide (FIG. 22; black circle) or PKN (54–73) (FIG. 22: white circle) as an inhibitor. The concentration of δPKC peptide was Km concentration (10 μM). The protein kinase reaction was carried out in the presence of PKN (39–53) peptide or PKN (54–73) peptide with various concentrations.

In order to judge the specificity of the activity of the inhibitor peptide, a protein kinase assay was carried out using PKA as an enzyme specimen. The catalytic subunit of bovine heart PKA used in the experiment was purified according to a method described in Bechtel, P. J. et al., J. Biol. Chem. 252, 2691–2697 (1977). The protein kinase activity of PKA was measured by using Kemptide (Kemp, B. E. et al., J. Biol. Chem. 252, 4888–4894 (1977) as a substrate under the same conditions as those used in Example 13, except that arachidonic acid was not used. The concentration of Kemptide was the Km concentration (16 μM), and measurement was made using PKN (39–53) peptide as an inhibitor (FIG. 22; white square). The kinase activity was determined in the same manner as in Example 13.

As a result, the PKN (39–53) peptide inhibited the phosphorylation of δPKC peptide, and this inhibition was dependent upon the concentration of PKN (39–53) peptide. The IC$_{50}$ (an inhibitor peptide concentration required to give 50% inhibition of the peptide substrate phosphorylation at the Km concentration) was approximately 80 μM (FIG. 22; black circle).

By contrast, PKN (54–73) peptide had little or no inhibitory activity (FIG. 22; white circle). The specificity of the peptide was confirmed with another basic amino acid-requiring protein kinase (PKA). The peptide PKN (39–53) was found to be a poor inhibitor of the PKA with a IC$_{50}$ of not less than 1,000 μM (FIG. 22; white square). The above results show that PKN (39–53) peptide specifically inhibits the protein kinase activity of PKN. It was suggested that PKN (39–53) peptide act as a pseudosubstrate for PKN.

Example 15

Effect of PKN (39–53) Peptide in Protein Kinase Activity of PKN

In order to confirm the function of PKN (39–53) as a pseudosubstrate for PKN, kinetic assays were performed with purified PKN, a fixed ATP concentration of 100 μM, and various concentrations of δPKC peptide (10–80 μM). The protein kinase reaction of PKN was performed in the same manner as in Examples 13 and 14. The results, performed in the presence of 40–80 μM PKN (39–53) peptide, are shown in double-reciprocal plots (FIG. 23 (A)). The inhibition was competitive-noncompetitive and gave a linear secondary plot of Km/Vmax (a concentration required to give a half-maximal velocity/maximal velocity) versus inhibitor peptide concentrations (FIG. 23 (B)). The apparent inhibitory constant (Ki) obtained from double-reciprocal plots and secondary plots of Km/Vmax versus a concentration of inhibitor peptide gave a value of 41 μM (FIG. 23 (B)). The inhibitor peptide gave an uncompetitive inhibition plot with varying ATP concentration, indicating that inhibition was not occurred at the ATP-binding site (data not shown).

The above effect shows that PKN (39–53) peptide acts as an autoinhibitory sequence of the enzyme and the inhibition is noncompetitive with ATP.

Example 16

Identification of the Rho Binding Region of PKN Using Yeast Two-hybrid System

To characterize the association between PKN and RhoA in further detail, studies were made using the yeast two-hybrid system. The N-terminal regulatory region of human PKN fused to the LexA DNA binding domain was coexpressed with RhoA or RhoA mutants fused to the VP16 activation domain in yeast strain L40.

Scheme of the fusion gene constructs for the truncated PKN cDNA used in the present invention was as shown in FIG. 25. The cDNA fragments encoding various length of human PKN were inserted into the vector pBTM116

(Example 7) in frame with the upstream LexA DNA-binding domain sequences or the vector pVP16 (Example 7) in frame with the upstream VP16 transcription activation domain sequences. The cDNA fragments encoding human RhoA, RhoA$^{Val14}$, and RhoA$^{Ala37}$ were obtained by digesting pGEX-RhoA, pGEX-RhoA$^{Val14}$, and pGEX-RhoA$^{Ala37}$ (Example 1) with restriction enzymes, respectively, then cloned into pBTM116 and pVP16.

The expression plasmids were transfected into yeast L40 cells and plated on semi-solid media lacking tryptophan and leucine. Interaction was examined using a filter lift assay for the β-galactosidase activity in the same manner as in Example 6.

As a result, as shown in FIG. 24, the β-galactosidase activity was induced in the transformants expressing PKN and RhoA$^{Val14}$, a GTPase defective mutant (Ridley, A. J. & Hall, A. Cell 70, 389–399 (1992)), whereas it was detected in neither the transformants expressing PKN and wild type RhoA nor the transformants expressing PKN and RhoA$^{Ala37}$, an effector domain mutant (Examples 3 and 4, Paterson, H. F. et al. J. Cell Biol. 111, 1001–1007 (1990)).

The Rho family members are known to have a CAAX motif (C, cysteine; A, aliphatic amino acid; X, any amino acid) in their C-terminal region, and to undergo post-translational modifications including geranylgeranylation, proteolysis, and carboxyl-methylation, and this modification is considered important for the Rho to be targeted by a cell membrane and activated (Katayama, M. et al., J. Biol. Chem. 266, 12639–12645 (1991); and Adamson, P. et al., J. Biol. Chem. 267, 20033–20038 (1992). When the CAAX motif is present in RhoA fusion protein, it is expected that the RhoA fusion protein is not efficiently transferred into the nucleus, leading to a possibility that it is difficult to detect the binding between the RhoA fusion protein and the PKN fusion protein. Accordingly, to prevent association of RhoA fusion proteins with membranes and to efficiently transfer the RhoA fusion protein into the nucleus, the two-hybrid system was carried out using RhoA mutants (hereinafter referred to as "RhoA CLVL$^-$"), which lack the C-terminal lipid modification site. cDNA corresponding to human RhoA which lacks the C-terminal lipid modification site (hereinafter referred to as "RhoA CLVL$^-$") was prepared by PCR and inserted into pBTM116 and pVP16.

As a result, PKN interacted with RhoA CLVL$^-$ and with RhoA$^{Val14}$CLVL$^-$, though did not interact with RhoA$^{Ala37}$CLVL$^-$. Similar results were obtained from the combination of RhoA fused to LexA and PKN fused to VP16 (FIG. 24). Thus, the specific interaction between activated RhoA and PKN was supported by the two-hybrid system, and these results suggest that the CAAX motif of RhoA is not required for the interaction with PKN.

To identify the binding region of PKN for RhoA, the various expression plasmids with the truncated PKN were transfected with RhoA$^{Val14}$CLVL$^-$ into yeast cells. As shown in FIG. 25, RhoA$^{Val14}$ CLVL$^-$ interacted with the region corresponding to the amino acid sequences 1–538, 3–135, and 33–111 in SEQ ID NO: 1. The results demonstrate the presence of the Rho protein-binding region in the amino acid sequence 33–111 in SEQ ID NO: 1.

This region contains the first leucine zipper-like motif (Mukai, H. et al., Biochem. Biophys. Res. Commun. 204, 348–356 (1994); and Mukai, H. & Ono, Y., Biochem. Biophys. Res. Commun. 199, 897–904 (1994). Therefore, this motif may play some roles in the interaction between PKN and RhoA.

Example 17

Inhibition of Binding, Between Rho and PKN, With Synthetic Peptides

Then, the interaction between PKN, prepared by in vitro translation, and GTPγS.GST-RhoA (Example 1) was determined in the presence of synthetic peptides, corresponding to various N-terminal regions of PKN, according to the following method.

A protein corresponding to the amino acid sequence 1–474 in SEQ ID NO: 1) was prepared by in vitro translation. GTPγS or GDP.GST-RhoA (15 nM) was incubated with PKN (1.5 μl) prepared by in vitro translation in a total volume of 200 μl of binding buffer (20 mM Tris/HCl at pH 7.5, 1 mM EDTA, 0.5 mM DTT, 5 mM MgCl$_2$ and 1 μg/ml leupeptin) for 60 min at 4° C. Then 40 μl of glutathione-Sepharose 4B (Pharmacia Biotech) preincubated in binding buffer containing 10 mg/ml E. coli extracts to block non-specific binding was added, and the mixture was rotated for 30 min at 4° C. Unbound proteins were removed by four washes with binding buffer containing 0.2% Nonidet P-40 and 50 mM NaCl, and by two washes with binding buffer. Specifically bound proteins were eluted with binding buffer containing 10 mM reduced glutathione and subjected to SDS-PAGE, and the gel was subjected to autoradiography.

Synthetic peptide fragments for potential RhoA binding region of PKN were synthesized with an automated peptide synthesizer (Applied Biosystems, model 431). An experiment using synthetic peptides wes carried out using the peptides in various concentrations in 200 μl of binding buffer.

As a result, as shown in FIG. 26, in the absence of the synthetic peptide, PKN prepared by in vitro translation bound specifically to GTPγS.GST-RhoA. The synthetic peptide fragments corresponding respectively to the amino acid sequences 74–93 and 94–113 in SEQ ID NO: 1 inhibited the binding of PKN to the GTPγS.RhoA in a concentration-dependent manner (FIG. 27). The inhibition was observed in peptides having concentrations of 30 μM and not less than 100 μM (FIG. 27).

Further, the synthetic peptide fragment corresponding to the amino acid sequence 82–103 in SEQ ID NO: 1 also inhibited the binding of PKN to the GTPγS.GST-RhoA in a concentration-dependent manner (FIG. 28).

These results suggest that the region corresponding to the amino acid sequence 74–113, particularly amino acids 82–103, in SEQ ID NO: 1 is critical for this interaction.

Example 18

Effect of N-Terminal Region of RKN on GTPase Activity of Rho Protein

Protein kinases, such as the activated Cdc42Hs-associated kinase p120$^{ACK}$ and the p21-(Cdc42/Rac) activated kinase p65$^{PAK}$, which bind to the active form of small G proteins, are known to inhibit the endogenous and GAP-stimulated GTPase activity of these small GTP binding proteins (Manser, E. et al., Nature, 367, 40–46 (1994); and Manser, E. et al., Nature 363, 364–367 (1993)). To determine whether the GTPase activity of RhoA is influenced by binding to PKN, the residual bound radioactivity of RhoA fused to GST or RhoA$^{Val14}$ fused to GST preloaded with [γ-$^{32}$p] GTP (1.11 TBq/mmol, DuPont-New England Nuclear) was measured in the presence or absence of PKN.

Expression vector for the N-terminal region of human PKN fused to GST was made by subcloning the cDNA fragment encoding the amino acid sequence 1–538 in SEQ ID NO: 1 into pGEX vector (Pharmacia Biotech Inc.). GST fusion proteins were expressed in E. coli and affinity-purified on glutathione-Sepharose 4B in the same manner as in Example 8. MBP-PKN was prepared in the same manner as in Example 4.

Assay for the endogenous GTPase activity was carried out as follows: two μM of purified RhoA fused to GST was incubated with 5 μM of [γ-$^{32}$p] GTP (1.11 TBq/mmol) in 50 mM Tris/HCl at pH 7.5, 10 mM EDTA, 1 mM MgCl$_2$, 50 mM NaCl, 1 mM DTT, 0.3% CHAPS at 30° C. The exchange reaction was stopped by placing the reaction mixture on ice, followed by addition of MgCl$_2$ to a final concentration of 10 mM. The [γ-$^{32}$p] GTP-loaded RhoA fused to GST or RhoA$^{Val14}$ fused to GST (0.2 μM) was incubated at 30° C. with either the presence or absence of 10 nM of GST-PKN (the amino acid sequence 1–540) in 60 μl of hydrolysis buffer (50 mM Tris/HCl at pH 7.5, 5 mM MgCl$_2$, 1 mM DTT, 1 mM GTP and 0.1 mg/ml bovine serum albumin). The reaction was stopped by the addition of about 2 ml of ice-cold buffer (20 mM Tris/HCl at pH 7.5, 100 mM NaCl and 25 mM MgCl$_2$), followed by rapid filtration on a nitrocellulose filter (BA-85, pore size 0.45 μm, available from Schleicher & Schuell). The filter was washed three times with the same ice-cold buffer. The radioactivity collected on the filter was determined.

The GAP-stimulated GTPase activity of RhoA was assayed by measuring the decreased radioactivity of [γ-$^{32}$p] GTP.GST-RhoA for 2 min at 25° C. in the presence of 50 nM of p122 Rho GAP fused to GST (GST-RhoGAP) and MBP-PKN with various concentrations in 100 μl of reaction mixture (20 mM Tris/HCl at pH 7.5, 10 mM EDTA, 1 mM DTT, 10 mM MgCl$_2$, 1 mM GTP, 0.075% CHAPS, 0.25 mM L-α-dimyristoylphosphatidylcholine, 100 nM [γ-$^{32}$p] GTP bound form of GST-RhoA) (Homma, Y. & Emori, Y., EMBO J. 14, 286–291 (1995).

As a result, the half-life of GTP bound to RhoA fused to GST was 12 min (FIG. 29), while that of RhoA$^{Val14}$ was 100 min (data not shown). The addition of a fusion protein constituted by the amino acid sequence 1–538 in SEQ ID NO: 1 and GST increased the half life of GTP bound to RhoA to not less than 15 min, whereas the addition of GST did not affect the GTP hydrolysis rate. These results indicate that the N-terminal region of PKN has an activity to inhibit the endogenous GTPase activity of RhoA. This inhibition was dependent on the concentration of PKN (FIG. 30).

As shown in FIG. 31, MBP-PKN inhibited the GST-RhoGAP-stimulated GTPase activity of GST-RhoA in a concentration-dependent manner, suggesting that binding of the N-terminal region of PKN to RhoA inhibits the interaction of GAP with RhoA.

These results show that binding of the N-terminal region of PKN to RhoA inhibits the endogenous GTPase activity of RhoA. Thus, it was found that the degree of interaction between PKN and Rho can be determined by determining the GTPase activity of Rho. Furthermore, it was clearly demonstrated that an addition of GAP for Rho to the screening system permits more precise determination of GTPase activity.

Example 19

Effects of Heat Shock on Subcellular Distribution of PKN (1): Biochemical Analysis Using Immunoblotting Immunoblotting was performed to determine the amounts of PKN in NIH 3T3, Rat-1, and Balb/c 3T3 cell lysates by using polyclonal antisera (αN2, αC6, and αF1) which specifically react with PKN. Specifically, it was performed according to the following procedure.

NIH 3T3 cells were grown in Dulbecco's modified eagle medium (DMEM) containing 10% calf serum. Balb/c 3T3 cells and Rat-1 cells were grown in DMEM containing 10% fetal calf serum (FCS). Cell lines were incubated in a humid 37° C. chamber containing 5% CO$_2$, and experiments were performed using cells in subconfluent growing phase. Proteins were extracted from these cells and subjected to SDS-polyacrylamide gel electrophoresis (PAGE) (Lammli, U.K. Nature 227, 680–685 (1970)) and immunoblotting according to the procedure described in Kitagawa, M. et al., Biochem, J. 310, 657–664 (1995).

Polyclonal antisera used in the immunoblotting were prepared by the following method. αN2 was prepared by immunizing a rabbit with a fragments corresponding to amino acids 1–391 of rat PKN prepared by expression in *E. coli* (Mukai, H. et al., Biochem., Biophys. Res. Commun. 204, 348–356 (1994)). αC6 was prepared by immunizing a rabbit with a fragment, corresponding to the sequence of amino acids 863–946 of rat PKN prepared by expression in *E. coli*, according to the procedure described in Mukai, H. et al. (1994), ibid.) αF1 was prepared by employing as an antigen the full-coding region of rat PKN prepared by expression in Sf9 cells (Mukai, H. & Ono, Y., Biochem. Biophys. Res. Commun. 199, 897–904 (1994)). Epitope specific reactions of αN2, αC6, and αF1 were confirmed by immunoblotting (Mukai, H. et al. (1994), ibid.) using amino- and carboxyl-terminal antigenic regions of PKN. Blots were developed by the enhanced chemiluminescence method.

The results were as shown in FIG. 32. Specifically, the antisera (αN2, αC6, and αF1) specifically recognized PKN derived from NIH3T3, Balb/c3T3 and Rat-1 cells cultured at 37° C. Heat shock treatment (at 42° C. for 90 min) of the cells did not affect the total level of PKN in NIH3T3, Balb/c3T3 and Rat-1 cells (data not shown). The heat shock treatment was achieved by shifting replica dishes of cultured cells from a 37° C. incubator containing 5% CO$_2$ to an incubator containing 5% CO$_2$ at 42° C., and the time after the shift was designated as the time of heat treatment.

The effect of heat shock on the distribution of PKN in cytosolic, plasma membrane, and nuclear fractions was then examined. The preparation of each cellular fraction was carried out according to the following procedure.

Firstly, cells were harvested, suspended in 1 ml of buffer A (10 mM Tris/HCl at pH 7.5, 1 mM EGTA, 1 mM EDTA, 5 mM MgCl$_2$, 1 mM phenylmethylsulfonyl fluoride (PMSF), 1 μg/ml leupeptin), and homogenized with 30 strokes in a Dounce homogenizer. The protein contents of the total cell homogenates were determined by the Peterson's method (Peterson, G. L. Anal. Biochem. 83, 346–356 (1977)), and equal amounts of protein were centrifuged at 500×g for 7 min at 4° C. to obtain the nuclear pellets and postnuclear fractions. The nuclear pellets were washed once with buffer A. The postnuclear fractions were further centrifuged at 100,000×g for 1 hr at 4° C. to give the cytosolic supernatants and plasma membrane pellets. These supernatant and pellet fractions were subjected to SDS-PAGE and immunoblotting as described above.

The results were as shown in FIG. 33. That is, PKN was predominant in the cytosolic fraction in untreated cells, whereas heat treatment of the cells resulted in increased PKN in the nuclear fraction with PKN in the cytosolic fraction being decreased. The heat treatment did not result in any significant change in the level of PKN in the plasma membrane fraction.

Example 20

Effects of Heat Shock on Subcellular Distribution of PKN (2): Cellular Biological Analysis Using Immunofluorescence Staining The distribution of PKN in terms of immunofluorescence in NIH 3T3 cells was investigated using antisera (αN2, αC6, and αF1). The immunofluorescence was carried out according to the following procedure.

Cells grown on coverslips were washed twice with phosphate-buffered saline (PBS), fixed for 1 hr at 4° C. in 4% paraformaldehyde, rinsed with PBS, and then blocked for 1 hr in PBS-T (PBS containing 0.05% Triton X-100) containing 5% normal goat serum. After washing with PBS, cells were incubated overnight at 4° C. with each antiserum which has been diluted with PBS to an antiserum concentration of about 10 μg/ml. Coverslips were then rinsed with PBS-T, and incubated with fluorescein isothiocyanate isomer I (FITC)-conjugated goat anti-rabbit IgG (Medical and biological laboratories, Co. Ltd.) for 60 min. Coverslips were rinsed with PBS-T followed by PBS, mounted with glycerol containing 0.1% 1, 4-diazabicyclo (2, 2, 2) octane (DABCO), and viewed on a Zeiss laser scanning microscope.

The results were as shown in FIG. 34. Specifically, PKN was detected in the cytoplasmic region of untreated cells. Consistent with the results of immunoblotting, heat-shocked cells exhibited a pronounced increase in the immunofluorescence of PKN associated with the nucleus. Nonspecific fluorescence determined by incubation without primary antiserum was negligible (data now shown).

To examine whether the nuclear translocation is specific for PKN, the immunofluorescence was observed using antiserum against protein phosphatase 2A (αPP2A). As a result, there was no difference in the subcellular distribution of immunoreactivity of αPP2A between heat-shocked and untreated cells, indicating that the nuclear translocation of PKN was not due to the nonspecific effect of heat shock. FIG. 35 shows that these phenomena were also observed in Rat-1 cells and Balb/c 3T3 cells.

Then, an experiment was then made in order to examine whether the nuclear translocation of PKN by heat shock is reversible. Specifically, the cells were subjected to heat shock treatment and then cultured for 4 hr at 37° C. As a result, immunofluorescence of PKN redistributed to the perinuclear and cytoplasmic region (FIGS. 34 and 35), indicating that the nuclear translocation of PKN is reversible. The immunofluorescence of PKN resided within the nucleus rather than in the unclear membranes in heat-shocked cells as shown by confocal microscopy (FIG. 36).

Example 21

Effects of Sodium Arsenite, Serum Starvation, and Ultraviolet Irradiation on Subcellular Distribution of PKN: Cytobiological Studies (1) Nuclear Translocation of PKN by Treatment with Sodium Arsenite An experiment was made in order to examine whether the subcellular distribution of PKN is influenced also by chemical shock. It is known that toxic compounds and toxic heavy metals also induce heat shock proteins and the stress responses in experimental systems (Maytin, E. V. & Young, D. A., J. Biol. Chem. 258, 12718–12722 (1983)). It is also known that cellular response similar to the stress induced by the heat shock is created also by treatment with sodium arsenite (Welch, W. J. & Suhan, J. P., J. Cell Biol. 103, 2035–2052 (1986)). Accordingly, to study the influence of sodium arsenite, sodium arsenite was added to a medium, followed by incubation of Rat-1 cells.

As a result, the treatment with 50 μM sodium arsenite resulted in the translocation of PKN to the nucleus as observed by microscopic examination (FIG. 37). Similar results were obtained when NIH 3T3 cells and Balb/c 3T3 cells were treated with 80 μM sodium arsenite (data not shown).

(2) Nuclear Translocation of PKN by Serum Starvation

Further, investigation was made on whether the translocation of PKN to the nucleus could also be induced by other stresses such as serum starvation. The serum starvation was performed by replacing medium with a serum-free medium containing 1 mg/ml bovine serum albumin (free from lipid).

As a result, the translocation of PKN to the nucleus was also observed when NIH 3T3 cells were subjected to serum starvation (FIG. 38), and PKN gradually returned to the cytoplasmic region after addition of 10% fetal calf serum. Return of PKN to the nonstressed state took at least 4 hr (FIG. 38).

(3) Subcellular Distribution of PKN by Ultraviolet Irradiation

Ultraviolet irradiation is other means for inducing stress in experiments, and ultraviolet response of mammalian cells is characterized by a rapid and selective increase in gene expression mediated by AP-1 and NF-κB (Devary, Y. et al., Science 261, 1442–1445 (1993); and Devary, Y. et al., Mol. Cell Biol. 11, 2804–2811 (1991)). It is known that at least part of the stress response to ultraviolet irradiation is mediated by JNK/SAPK subfamily and p38/ PK (Devis, R. et al., TIBS 19, 470–473 (1994); and Cano, E & Mahadevan, C., TIBS 20, 117–122 (1995)). Accordingly, an experiment was made to examine whether the nuclear translocation of PKN could be induced by ultraviolet irradiation. The ultraviolet irradiation was performed by treating the cells with UV-C, followed by incubation at 37° C. for one hr (Adler, V. et al., J. Biol. Chem. 270, 26071–26077 (1995)).

However, the translocation of PKN was not observed when the NIH 3T3 cells were exposed to 40 J/m$^2$ UV-C irradiation (data not shown) which is enough for activation of JNK (Derijard, B. et al., Cell 76, 1025–1037 (1994)).

Example 22

Effects of Overexpression of Kinase-Negative Mutant of PKN

To further analyze the change, in subcellular distribution of PKN, induced by stress, the effects of overexpression of mutant PKN were studied. A single point mutation of human PKN in the kinase domain (K644R; PKN-PK$^-$) was used as a protein kinase-negative mutant.

At the outset, NIH 3T3 cells which stably overexpresses PKN-PK$^-$ were constructed by the following procedure. A vector phPKNH4-PK$^-$ was constructed by conversion of the lysine at the potential ATP-binding site to an arginine by in vitro site-directed mutagenesis (Mukai, H. & Ono, Y., Biochem. Biophys. Res. Commun. 199, 897–904 (1994)). A vector pMhPKN-PK$^-$ for expression of PKN-PK$^-$ in mammalian cells was constructed by insertion of the 2.9 kb partial EcoRI digested-cDNA from phPKNH4-PK$^-$ into the Eco RI site of pTB701 (Ono, Y. et al., J. Biol. Chem. 263, 6927–6932 (1988)). pMhPKN-PK$^-$ was introduced into NIH 3T3 cells with pWLneo (Stratagene), which carries a neomycin resistance gene (at a molar ratio of 50:1), and clones resistant to 400 μg/ml of G418 were isolated. One of the clones, PK$^-$/neo#5, which showed the most abundant expression of PKN-PK$^-$ by immunoblotting as described above (Example 19), was employed for the experiments.

To examine whether PKN-PK$^-$ has kinase activity, the kinase activity of PKN-PK$^-$, which has been immunoprecipitated by cells, was assayed. Specifically, the assay was carried out according to the following procedure.

The experiment on immunoprecipitation was carried out at 0 to 4° C. The wild type NIH 3T3 cells and PK$^-$/neo#5 cells were lysed in 0.5 ml of buffer B (20 mM Tris/HCl at pH 7.5, 1% Nonidet P-40, 137 mM NaCl, 10% glycerol, 1 mM PMSF, 20 μg/ml aprotinin, 10 μg/ml leupeptin, 2.5 mM sodium fluoride, 0.25 mM sodium vanadate) for 1 hr. Insoluble materials were removed by centrifugation at 15,000×g for 10 min, and the supernatants were incubated with 1 μl of 10-fold diluted antiserum αN2 (Example 19) for 2 hr. After addition of 40 μl of 50% protein A Sepharose, the mixtures were further incubated for 1 hr. The immunoprecipitates adsorbed to protein A Sepharose were washed twice with buffer C (100 mM Tris/HCl at pH 7.5, 0.5 M LiCl, 2.5 mM sodium fluoride, 0.25 mM sodium vanadate) and twice with buffer D (10 mM Tris/HCl at pH 7.5, 2.5 mM sodium fluoride, 0.25 mM sodium vanadate). Each immunoprecipitate was incubated for 5 min at 30° C. with a 25-μl mixture (20 mM Tris/HCl at pH 7.5, 4 mM $MgCl_2$, 40 μM ATP, 185 kBq of [$\gamma$-$^{32}$P] ATP without exogenous substrate. After addition of 5 μl of 6×Laemmli sample buffer (Laemmli, U. K. Nature 227, 680–685 (1970)) and boiling, a 20-μl aliquot of the mixture was subjected to 7% SDS-PAGE. The phosphorylation was visualized and quantitated by an imaging analyzer (Fuji BAS1000).

As a result, it was confirmed that the enzyme activity of PKN-PK$^-$ was inactivated (FIG. 39). Further, PK$^-$/neo#5 cells were shown by immunoblotting to overexpress the PKN-PK$^-$ mutant protein by 20 times higher than the endogenous wild type PKN (FIG. 39).

As shown in FIG. 40, microscopic observation revealed that immunofluorescence of PKN in cells expressing PKN-PK$^-$ was distributed in the cytoplasmic region and exhibited no difference between untreated and 42° C. heat-treated cells. No obvious change was observed when the temperature of heat treatment was further upshifted to 44° C. (FIG. 40). These results indicate that the PKN-PK$^-$ mutant protein does not translocate to the nucleus. The ratio of immunofluorescence intensity of nucleus to that of cytoplasm, as measured under confocal microscope, was not significantly different between untreated and heat-shocked cells, suggesting that, in the case of overexpression of PKN-PK$^-$ protein, even the wild type endogenous PKN does not translocate from the cytoplasm to the nucleus.

Thus, the intercellular overexpression of PKN-PK$^-$ inhibits the translocation of the endogenous PKN from the cytoplasm to the nucleus. Therefore, the translocation of PKN from cytoplasm to nucleus can be inhibited by intracellular expression of a peptide, having a PKN-modified amino acid sequence possessing no protein kinase activity or containing no protein kinase region, or a derivative thereof, or alternatively by treatment of the cells with a material which inhibits the protein kinase activity or the enhancement of the protein kinase activity.

Example 23

Search, for Materials Having Inhibitory Activity Against Interaction Between Activated Rho and PKN, Using Yeast Two-Hybrid System A pVP16 vector with a cDNA fragment encoding PKN (1–540) inserted thereinto was cotransfected, with a pBTM116 vector with a cDNA encoding human RhoA$^{Val14}$ inserted thereinto, into yeast (S. cerevisiae) strain L40 (Mat a trp1 leu2 his3 ade2 LYS2::(LexAop)4-HIS3 URA3::(LexAop)8-LacZ) to obtain transformants (Example 16). The transformants were plated on 20 ml of BMM (BMM/Ade/His) medium containing adenine (Ade) and histidine (His), stationarily cultivated and grown at 30° C. to 3×10$^7$ cells/ml, and then harvested. The BMM medium, containing Ade and His, used was prepared so as to contain 20 g/liter dextrose, 2 g/liter asparagine, 2 μg/liter biotin, 200 μg/liter calcium pantothenate, 10 mg/liter inositol, 200 μg/liter niacin, 200 μg/liter pyridoxine hydrochloride, 200 μg/liter chiamin hydrochloride, 30 μg/liter boric acid, 20 μg/liter copper sulfate, 100 μg/liter potassium iodide, 125 μg/liter ferric chloride, 50 μg/liter magnesium sulfate, 100 μg/liter sodium molybdate, 150 μg/liter zinc sulfate, 1.5 μg/liter potassium phosphate (monobasic), 500 mg/liter magnesium sulfate, 330 mg/liter calcium chloride, 20 mg/liter adenine, and 20 mg/liter histidine.

One half of the collected transformants was suspended in 300 ml of BMM/Ade/His medium (His$^+$ medium), containing 2% purified agar powder (Nakarai Tesuque Inc.) and 0.002% SDS, kept at 48° C. so as to give 1×10$^6$ cells/ml, and aliquots (30 ml each) from the suspension was plated on a rectangular plate. The other half of the transformants was similarly suspended in 300 ml of BMM/Ade medium (His$^-$ medium) containing 2% purified agar powder and 0.002% SDS, and aliquots (30 ml each) from the suspension was plated on a rectangular plate (230×80×15 mm).

Two sets of paper disks having a diameter of 6 mm (ADVANTEC Thin PAPER DISK, available from Toyo Roshi Kaisha Ltd.) were immersed in each of cultured broths of various Actinomyces and fungi and then dried on a filter paper. After drying, one of the two sets of the paper disks was placed on a transformant culture plate with His$^+$ medium, while the other was placed on a transformant culture plate with His$^-$ medium, followed by incubation at 30° C. for 2 to 3 days. Thereafter, the diameter of a growth block circle, which had appeared around each paper disk, was measured, and the difference in size between the block circle appearing on the transformant culture plate with His$^+$ medium and the transformant culture plate with His$^-$ medium was measured.

Most of the cultured broths formed block circles having substantially the same size on both the plates. Very rarely, cultured broths, which had formed a significantly larger block circle on the plate with His$^-$ medium than on the plate with His$^+$ medium, were found (data not shown). For these cultured broths, substantially no block circle appeared in the case of the His$^+$ medium, suggesting that the broths contained no satisfactory substance for inhibiting the growth of yeast. On the other hand, a significant block circle appeared in the case of the His$^-$ medium, suggesting that the broths contain a substance which inhibits the interaction between the RhoA$^{Val14}$ and PKN (1–540). Thus, it has become apparent that the yeast two-hybrid system enables screening a substance which inhibits the interaction between Rho and PKN.

Example 24

Assay, of Binding Between α-Actinin and PKN, Using Yeast Two-Hybrid System

Million yeast colonies transformed with both human brain cDNA library fused to Gal4 transcriptional activation domain and a bait construct encoding PKNN1 fused to Gal4 DNA binding domain were screened. The screening was performed according to the following procedure.

Schemes of the fusion constructs for human PKN, human skeletal muscle type α-actinin (HuActSkl , designated in (Beggs, A., et al., J. Biol. Chem. 267, 9281–9288 (1992)) and non-skeletal muscle type α-actinin (HuActNm, designated in (Beggs, A., et al., J. Biol. Chem. 267, 9281–9288

(1992)) used in this study are shown in FIGS. 41 and 42. Screening of proteins, which bind to the N-terminal region of human PKN (the amino acid sequence 1–540, this region being designated as "PKNNl"), was performed as described in Example 6. Primary positive clones were recovered and retransfected into the original yeast host strain YGH1 (a, ura3–52, his3-200, ade2-101, lys2-801, trp1-901, leu2-3, Can$^r$, gal4-542, gal80-538, LYS2::gall$_{uas}$-gall$_{tata}$-HIS3, URA3::gall-lacZ) in combination with the Gal4bd-PKN or the Gal4bd-p53 tumor suppresser. Plasmids that activated marker expression only in the presence of PKN were analyzed further.

The 82 plasmids were isolated representing 16 different cDNA as judged by CDNA sequencing (Example 6). Three positive clones (clone#4, #10, and #25) encoded the skeletal muscle type α-actinin (HuActSkl) (Beggs, A., et al., J. Biol. Chem. 267, 9281–9288 (1992)). The clone#4 encoded HuActSkl from amino acid 333 to the C-terminus, and both clone#10 and clone#25 encoded HuActSkl from amino acid 344 to the C-terminus. All of the three clones contained complete C-terminus but lacked the N-terminal actin-binding domain (Fukami, K., et al., J. Biol. Chem. 271, 2646–2650 (1996)) (FIG. 42). These clones resulted in high β-galactosidase activity upon co-transformation with the PKN bait construct in the original yeast host strain YGH1.

Specificity of this interaction was tested further by measuring the ability of other combination of two-hybrid constructs, LexAbd (instead of Gal4bd)-PKN, and Gal4ad-α-actinin to support lacZ expression in L40 cells (MATa trpl leu2 his3 LYS2::lexA-HIS3 URA3::lexA-lacZ). As shown in FIG. 43, high β-galactosidase activity was also developed in this system, suggesting a specific interaction between amino-terminal region of PKN and α-actinin.

The two-hybrid methods was employed to identify the region of PKN that interacted with HuActSkl, and this region was compared with the binding site for RhoA, which binds to PKN, in vitro and in vivo. The RhoA binding site has been mapped on the amino acid 33–111 of PKN which corresponds to the first leucine zipper-like sequence of PKN (Example 16), whereas α-actinin hardly interacted with this region of PKN (FIG. 42). By contrast, α-actinin strongly interacted with the amino acid 136–189 of PKN, whereas no interaction was detected between RhoA and this region of PKN (data not shown). This region corresponds to the second leucine zipperlike sequence and the N-terminal region adjacent thereto, which is conserved through evolution in vertebrates (Mukai, H., et al., Biochim. Biophys. Acta 1261, 296–300 (1995)). Thus α-actinin binds to the region distinct from that which binds to Rho. These results raise the possibility that PKN binds simultaneously to RhoA and α-actinin.

Example 25

Binding of PKN to HuActSkl in vitro

α-Actinin is composed of 3 domains: an N-terminal actin-binding domain, extended rod-shaped domain with four internal 122 amino acid repeats (spectrin-like repeats), and a C-terminal region containing a pair of presumptive helix-loop-helix $Ca^{2+}$-binding motifs, often referred to as EF-hands (Blanchard, A., et al., J. Muscle Res. Cell Motil. 10, 280–289 (1989)).

To investigate whether PKN binds directly to α-actinin, and to clarify which part of α-actinin is necessary for binding of PKN, various truncated constructs of HuActSkl were produced as GST fusion proteins in E. coli (FIG. 42), and the interaction thereof with the in vitro transcripted N-terminal region of PKN was analyzed. Specifically, the investigation was performed according to the following procedure.

A plasmid for in vitro transcription of the full-length coding region of HuActSkl was constructed as follows: the cDNA encoding the N-terminal region (the amino acid sequence 1–422) of HuActSkl containing actinbinding domain was amplified by PCR from human brain cDNA library, and was ligated to the C-terminal part (the amino acid sequence 423–894) of clone#4 isolated in the two-hybrid screening. This cDNA for the full-length coding region of HuActSkl was subcloned into pBluescript II SK+ (Stratagene). The plasmid was linearized by cutting with XhoI, and cRNA was transcribed using T3 RNA polymerase.

In vitro transcription for the N-terminal region of PKN (the amino acid sequence 1–474, this region being designated as PKNN2 (Example 8)) was performed as described in Example 8. For in vitro translation, cRNAs were translated in rabbit reticulocyte lysate (Promega) in the presence of [$^{35}$S] methionine as described in Example 8.

For in vitro binding experiment, 2 μl of in vitro translated PKNN2 was mixed with 5 μg of each GST-α-actinin fusion protein or with 25 μg of GST alone in 400 μl of GST binding buffer (20 mM Tris/HCl at pH 7.5, 0.5 mM DTT, 150 mM NaCl, 0.05% Triton-X100, 1 mM EDTA, 1 μg/ml leupeptin) and incubated for 1 hr at 4° C. After addition of 25 μl of glutathione-Sepharose 4B pretreated with 10 mg/ml of E. coli extract to block nonspecific binding, the binding reaction was continued for additional 30 min at 4° C. The glutathione-Sepharose 4B was then washed four times in GST washing buffer (20 mM Tris/HCl at pH 7.5, 0.5 mM DTT, 1 mM EDTA, 1 μg/ml leupeptin) containing 0.5 M NaCl and 0.5% Triton X-100, and further washed with GST washing buffer. Bound proteins were eluted with GST elution buffer (100 mM Tris/HCl at pH 7.5, 10 mM glutathione, 120 mM NaCl, 1 mM EDTA, 0.5 mM DTT, 1 μg/ml leupeptin) and were subjected to SDS-PAGE. The binding was visualized and quantitated by an imaging analyzer (FUJI BAS1000).

As shown in FIG. 44, in vitro translated PKNN2 strongly bound to each human skeletal muscle type α-actinin fragment (the amino acid sequence 423–653, 653–837, and 486–607) but not to the fragment (amino acids 837–894, and 604–719). The complex was resistant to washing with 0.5% Triton X-100/0.5 M NaCl, indicating that the binding is not nonspecific.

The above results suggest that the recombinant α-actinin interacts directly with recombinant PKN, and that two distinct regions of HuActSkl, which correspond to the spectrin-like repeat 3 and the region containing the EF-hand-like motifs, play important roles in the binding to PKN.

As expected from the two-hybrid data (Example 24), the N-terminal region of PKN (amino acids 33–111) translated in vitro, which lacked the RhoA binding region, was satisfactory for direct binding to α-actinin (FIG. 44, lanes 18–20).

Example 26

Identification of Binding of PKN to Non-Skeletal Muscle Type α-Actinin (HuActNm) in vitro and $Ca^{2+}$ Dependency of its Interaction A number of distinct isoforms of α-actinin have been characterized, including skeletal, smooth, and non-muscle α-actinins, from various kinds of cells and tissues. The only recorded functional difference among these α-actinins is that binding of the non-muscle isoform to F-actin is inhibited by $Ca^{2+}$, whereas binding of the muscular isoform is insensitive to $Ca^{2+}$ (Burridge, K. & Feramiscoo, J. R. Nature 294, 565–567 (1981), Bennett, J. P., et al., Biochemistry 23, 5081–5086 (1984), Duhaiman, A. S. & Bamburg, J. R. Biocheistry 23, 1600–1608 (1984), and Landon, F., et al., Eur. J. Biochem. 153, 231–237 (1985)). In human, only one clone of the non-muscle cytoskeletal isoform (HuActNm, designated in Beggs, A., et al., J. Biol. Chem. 267, 9281–9288 (1992))which is highly homologous to HuActSkl (89% similarity and 80% identity for pairwise comparison) has been isolated (Millake, D. B., et al., Nucleic Acids Res. 17, 6725 (1989); and Youssoufian, H., et al., Am.

J. Hum. Genet. 47, 62–71 (1990)).

Accordingly, the present inventors have studied whether the in vitro translated PKNN2 could bind to the region of HuActNm corresponding to the PKN-binding site of HuActSkl in the same manner as in Example 25. The HuActNm fragment used in the experiment was prepared according to the following procedure.

cDNAs encoding the spectrin-like repeat 3 (the amino acid sequence 479–600) and EF-hand-like region (the amino acid sequence 712–843) of HuActNm were amplified by PCR from human brain cDNA library, and were ligated to pGEX4T vector. cDNAs encoding the spectrin repeat 20 and EF-hand-like region of α-actinin were amplified by PCR from rat brain cDNA library, and were ligated to pGEX4T vector. Expression and purification of GST or GST fusion proteins were performed according to the manufacturer's instruction (Phamacia Biotech Inc.). The eluate from glutathione-Sepharose 4B (Pharmacia Biotech Inc.) was dialyzed overnight against 10 mM Tris/HCl at pH 7.5 containing 1 mM EDTA, 1 mM DTT, and 0.1 µg/ml leupeptin.

Figure 45:
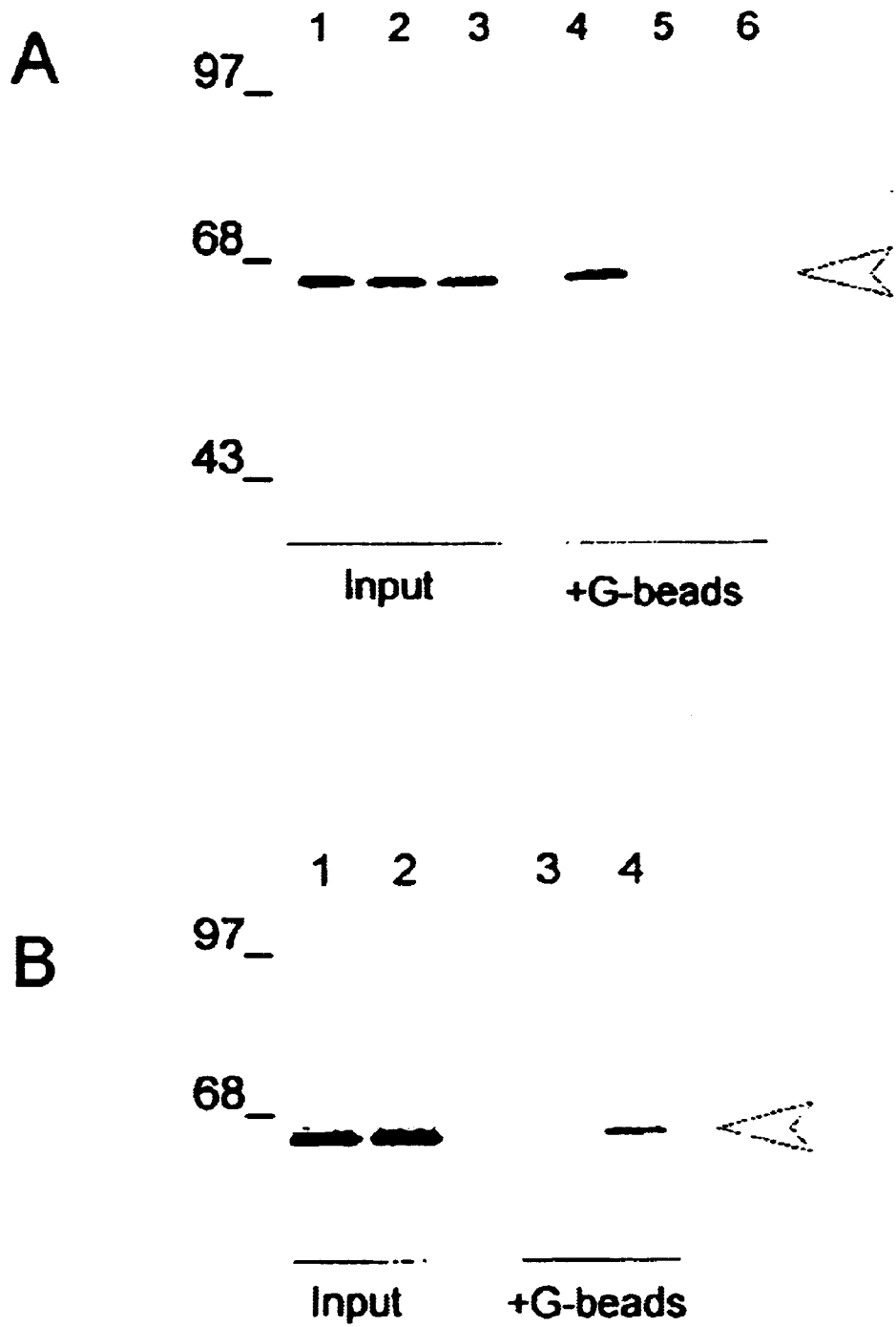

As shown in FIG. 45, PKNN2 could bind to spectrinlike repeat 3 domain of HuActNm, whereas the binding to the EF-hand-like domain of HuActNm was not detected in the absence of $Ca^{2+}$. However, PKNN2 could effectively bind to the EF-hand-like region of HuActNm in the presence of 1 mM $Ca^{2+}$ (FIG. 45).

Example 27

Study on Specificity of Binding Between PKN and α-Actinin

α-Actinin is a member of spectrin superfamily, including spectrin, dystrophin, and so on (Blanchard, A., et al., J. Muscle Res. Cell Motil. 10, 280–289 (1989), Dubreuil, R. R. Bioessays 13, 219–226 (1991); and Bennett, V, Physiol. Rev. 70, 1029–1065 (1990)). Family members are characterized by the N-terminal actin-binding domain, central rod-shaped spectrin-like repeats, and the C-terminal EF-hand-like domain. α-Spectrin contains 21 rod-shaped repeats in the N-terminal to the EF-hand-like domain. The C-terminus of α-spectrin is clearly related to α-actinin, and especially the repeat 20 of α-spectrin has extensive homology to the repeat 3 of α-actinin (Wasenius, V. M., et al., J. Cell Biol. 108, 79–93 (1989); and Hong, W. J. & Doyle, D. J. Biol. Chem. 264, 12758–12764 (1989)), and the position of the repeat in each protein seems to be related to each other.

Since PKN bound to the repeat 3 of α-actinin, the present inventors have examined whether PKN can bind to the repeat 20 of α-spectrin. As shown in FIG. 46, in vitro binding between PKN and the repeat 20 of rat α-spectrin was not detected in the same condition in which PKN bound to the repeat 3 of α-actinin. These results indicate that PKN specifically binds to the spectrin-like repeat of α-actinin.

Example 28

Binding of PKN to α-Actinin in Vivo

The interaction of α-actinin with PKN in vivo was examined by co-transfection experiment in COS7 cells. An epitope-tagged α-actinin was generated by fusion of a 9-amino acid epitope from the influenza HA to the amino terminus of clone#4 protein, enabling the selective immunoprecipitation of the tagged α-actinin polypeptide with anti-HA monoclonal antibody 12CA5 (Field, J., et al., Mol. Cell Biol. 8, 2159–2165 (1988)). Although this HA-tagged α-actinin contains the complete C-terminal region of α-actinin, it lacks the N-terminal actinbinding omain. The experiment was carried out according to the following procedure.

HA-tagged cDNA for HuActSkl (the amino acid sequence 333–894) was created by fusion of a cDNA encoding 9-amino acid epitope from the influenza HA to the amino terminus of clone#4. A vector pHA-Act was constructed by subcloning this cDNA into pTB701 (Ono. Y., et al., J. Biol. Chem. 263, 6927–6932 (1988)). Empty pHA vector not containing HuActSkl was constructed by subcloning a cDNA encoding only HA epitope into pTB701. A vector pHA-Act or empty pHA vector was cotransfected into COS7 cells with the expression vector pMhPKN3 (Mukai, H. & Ono, Y. Biochem. Biophys. Res. Commun. 199, 897–904 (1994)) encoding the full-length human PKN. After 48 hr, cells were lysed in lysis buffer (20 mM Tris/HCl at pH 7.5, 1% Nonidet P-40, 137 mM NaCl, 10% glycerol, 1 mM phenylmethylsulfonyl fluoride, 20 µg/ml aprotinin, 10 µg/ml leupeptin) for 1 hr. Insoluble materials were removed by centrifugation at 15,000×g for 10 min, and the supernatants were incubated with 12CA5 for 2 hr. After addition of 20 µl of 50% protein A Sepharose, the mixtures were further incubated for 1 hr. The immunoprecipitates adsorbed to protein A Sepharose were washed twice with HA wash buffer (100 mM Tris/HCl at pH 7.5, 0.5 M LiCl) and twice with 10 mM Tris/HCl at pH 7.5. The resultant immunoprecipitates were detected by immunoblotting with αC6 and 12CA5.

The anti-hemagglutinin (HA) monoclonal antibody 12CA5 was purchased from Boehringer Mannheim. αC6, a specific antiserum against PKN, was prepared by immunizing rabbits with the rat PKN protein (the amino acid sequence 863–946) prepared using *E. coli*. and then treating the immunized rabbits according to the conventional method.

The results were as shown in FIG. 47. After co-expression of HA-tagged α-actinin with the full-coding region of PKN in COS7 cells, anti-HA immunoprecipitates contained substantially immunoreactive PKN. These results suggest that the C-terminal region of α-actinin can associate in vivo with PKN.

Example 29

P14, 5P2-Dependent Binding Between PKN and α-Actinin

α-Actinin in vivo binds to various amounts of endogenous PI4, 5P2, and the specific interaction between α-actinin and PI4, 5P2 regulates the F-actingelating activity of α-actinin (Fukami, K., et at., Nature 359, 150–152 (1992)). This indicates that PI4, 5P2 causes a conformational change in α-actinin. Exogenously added PI4, 5P2 can bind to α-actinin strongly, and the binding is tight and stable (Fukami, K., et at., Nature 359, 150–152 (1992)).

Accordingly, the present inventors examined the binding activity of PKN with α-actinin in the presence or absence of PI4, 5P2. Since PI4, 5P2 binding region resides in the actinin-binding domain of α-actinin (Fukami, K., et at., J. Biol. Chcm. 271, 2646–2650 (1996)), in vitro translated full-length α-actinin (FIG. 42) containing actin-binding domain was used in this in vitro binding experiment. The experiment was carried out according to the following procedure.

For analysis of the effect of phosphatidylinositol 4,5 bisphosphate (PI4, 5P2) (Boehringer Mannheim) on the binding between α-actinin and PKN, 2 μl of in vitro translated full-length HuActSkl was mixed with 5 μg of GST-PKNN1 fusion protein or with 25 μg of GST alone in 400 μl of buffer P (20 mM Tris/HCl at pH 7.5, 0.5 mM DTT, 120 mM NaCl, 1 mM EDTA) and incubated for 1 hr at room temperature with or without PI4, 5P2. After addition of 25 μl of glutathione-Sepharose 4B pretreated with $E.$ $coli$ extract, the binding reaction was continued for additional 30 min at 4° C. The glutathione-Sepharose 4B was then washed four times in buffer P containing 0.01% Triton X-100. Bound proteins were eluted with GST elution buffer and were subjected to SDS-PAGE. The binding was visualized and quantitated by an imaging analyzer (FUJI BAS1000).

Figure 48:
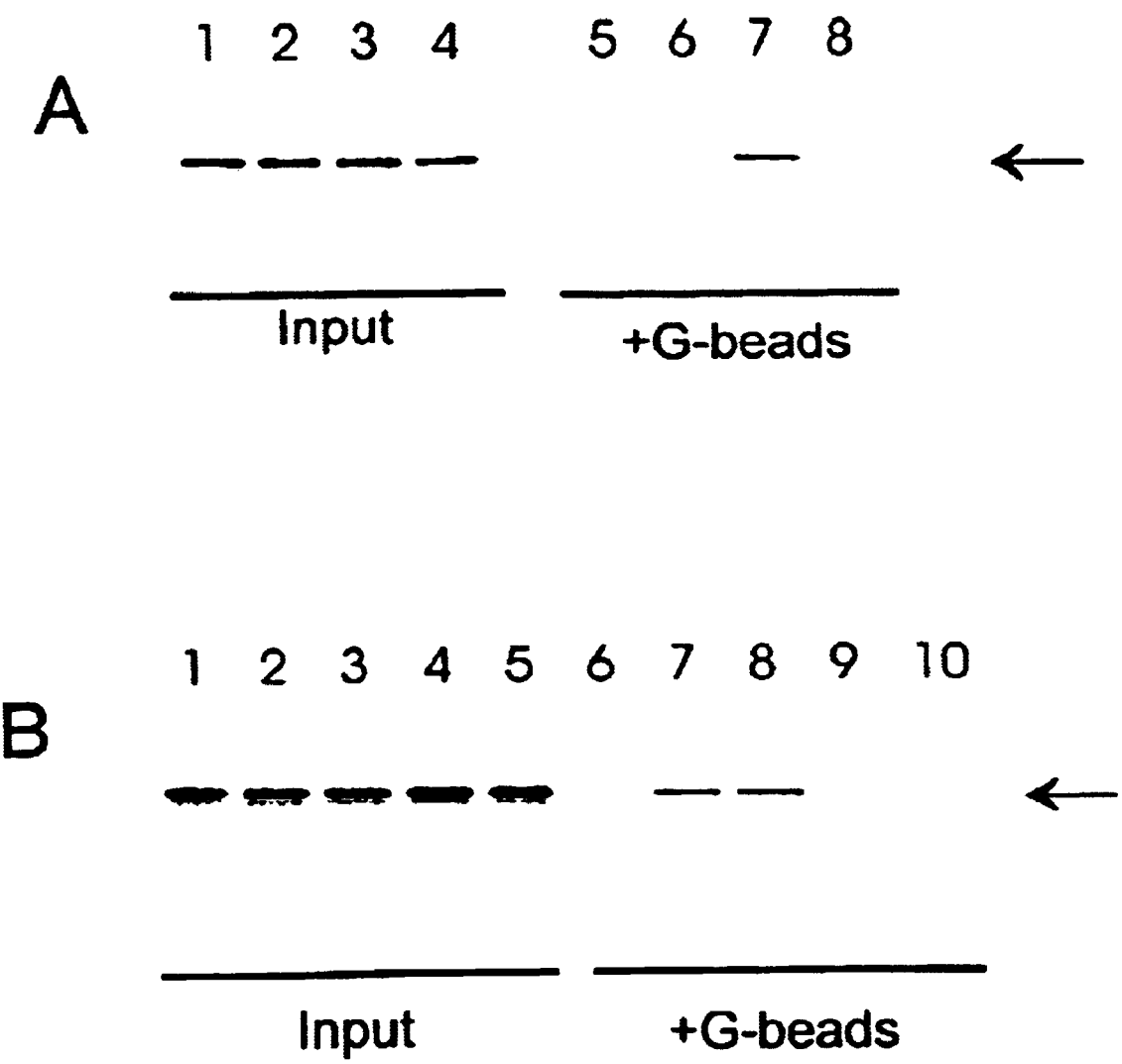

The results were as shown in FIG. 48. The full-length α-actinin very weakly but specifically bound to PKN in the absence of PI4, 5P2. However, addition of 10 μM PI4, 5P2 stimulated the binding of the full-length α-actinin to PKN (FIG. 48A). Therefore PI4, 5P2 appears to influence the conformation of α-actinin and exposes the binding region for PKN.

This binding activity was elevated with increased PI4, 5P2 concentration up to 2.5–10 μM, whereas, at higher concentrations up to 100 μM, the binding activity was decreased (FIG. 48B). This two-phase pattern of PI4, 5P2-dependency was also reported in the binding of α-actinin with PI3-kinase (Shibasaki, F., et al., Biochem. J. 302, 551–557 (1994)). Fukami et al. reported that the effect of PI4, 5P2 on gelating activity of α-actinin is increased up to 5–10 μM of PI4, 5P2, and that further increase in concentration of PI4, 5P2 gives a reduction in gelating activity to the basal level due to the formation of PI4, 5P2 micelles (Fukami, K., et at., Nature 359, 150–152 (1992)). The two-phase pattern of PI4, 5P2-dependent binding of α-actinin with PKN also may be explained by the same reason.

Example 30

Effect of α-Actinin on PKN Kinase Activity

The present inventors investigated whether the binding of α-actinin to PKN regulated or directly altered the catalytic function of PKN. The investigation was performed according to the following procedure.

α-Actinin used in the experiment was purified from bovine aorta by the method of Feramisco et al. (Feramisco, J. R. & Burridge, K. J. Biol. Chem, 255, 1194–1199 (1980)). The phosphorylation by PKN was carried out at 30° C. in an assay mixture containing 20 mM Tris/HCl at pH 7.5, 4 mM MgCl$_2$, 100 μM ATP, 185 kBq of [γ-$^{32}$p] ATP, substrates for phosphorylation (phosphate acceptors), 20 ng/ml of purified PKN from rat testis (Abe, M., et al., J. Biochem. Tokyo 107, 507–509 (1990)) in the presence or absence of 40 μM arachidonic acid as indicated in each experiment. Partial purified protein was boiled for 3 min to destroy endogenous kinase activity before use as the substrate for phosphorylation. After incubation for 5 min, the reaction was terminated by the addition of an equal volume of Laemmli's sample buffer (Laemmli, U. K. Nature 2Z7, 680–685 (1970)), and separated on SDS-PAGE. The gels were dried under vacuum and the phosphorylation was visualized and quantitated by an imaging analyzer (FUJI BAS1000). When the δPKC peptide (Mukai, H., et al. Biochem, Biophys. Res. Commun. 204, 348–356 (1994)) was used as the substrate for phosphorylation, reactions were terminated by spotting a mixture onto a Whatman P81 paper and submerging it in 75 mM phosphate, and followed by three times of 10 min washes. Incorporation of $^{32}$p into the peptide was assessed by scintillation counting.

As a result, the purified α-actinin from bovine aorta neither inhibited PKN autophosphorylation, nor affected PKN-catalyzed PKC pseudosubstrate peptide phosphorylation when added at >1000 molar excess to PKN (data not shown). Thus, α-actinin does not seem to be an direct modulator of PKN purified from the soluble fraction of rat testis in vitro.

Example 31

Phosphorylation of α-Actinin and Other Actin-Cytoskeletal Associated Proteins by PKN Since PKN bound to α-actinin, the present inventors tested whether α-actinin itself could be a substrate for PKN. PKN purified from rat testis did not phosphorylate α-actinin purified from bovine aorta (Example 30) and the recombinant α-actinin expressed in $E.$ $coli$ (data not shown).

The present inventors have searched PKN substrates among other actin-cytoskeletal proteins, including filamin, meta-vinculin, vinculin, talin, caldesmon, and actin. Actin was purified from rabbit skeletal muscle by the method of Mommaerts (Mommaerts, W. F. H. M. J. Biol. Chem. 559, 559 (1951)), Vinculin was purified from bovine aorta by the method of Kobayashi et al. (Kobayashi, R. & Tashima, Y. J. Muscle Res. Cell Motil. 11, 465–470 (1990)). Caldesmon was partially purified from bovine aorta by the method of Abe et al. (Abe, M., et al., J. Biochem. Tokyo 107, 507–509 (1990)).

Filamin, meta-vinculin, and talin were partially purified from bovine aorta as described in Feramisco, J. R. & Burridge, K. J. Biol. Chem. 255, 1194–1199 (1980).

Among them, caldesmon and G-actin were preferred substrates for PKN. As shown in FIG. 49, phosphorylation of G-actin and that of caldesmon were stimulated up to 2-fold and at least 6-fold in the presence of arachidonic acid, respectively.

Since some actin-based cytoskeletal proteins such as actin and caldesmon served as good substrates for PKN, it is estimated that PKN mediates the effects of Rho and phosphoinositides by phosphorylating these proteins.

SEQUENCE LISTING

<160> NUMBER OF SEQ ID NOS: 6

<210> SEQ ID NO 1
<211> LENGTH: 2968
<212> TYPE: DNA
<213> ORGANISM: Homo sapiens
<220> FEATURE:
<221> NAME/KEY: CDS
<222> LOCATION: (37)..(2862)

<400> SEQUENCE: 1

```
gaattcccgc gcagagactc caggtcgcag gtcgac atg gcc agc gac gcc gtg         54
                                       Met Ala Ser Asp Ala Val
                                         1               5 cag agt gag cct cgc agc tgg tcc ctg cta gag cag ctg ggc ctg gcc        102
Gln Ser Glu Pro Arg Ser Trp Ser Leu Leu Glu Gln Leu Gly Leu Ala
             10                  15                  20 ggg gca gac ctg gcg gcc ccc ggg gta cag cag cag ctg gag ctg gag        150
Gly Ala Asp Leu Ala Ala Pro Gly Val Gln Gln Gln Leu Glu Leu Glu
         25                  30                  35 cgg gag cgg ctg cgg cgg gaa atc cgc aag gag ctg aag ctg aag gag        198
Arg Glu Arg Leu Arg Arg Glu Ile Arg Lys Glu Leu Lys Leu Lys Glu
     40                  45                  50 ggt gct gag aac ctg cgg cgg gcc acc act gac ctg ggc cgc agc ctg        246
Gly Ala Glu Asn Leu Arg Arg Ala Thr Thr Asp Leu Gly Arg Ser Leu
 55                  60                  65                  70 ggc ccc gta gag ctg ctg ctg cgg ggc tcg tcg cgc cgc ctc gac ctg        294
Gly Pro Val Glu Leu Leu Leu Arg Gly Ser Ser Arg Arg Leu Asp Leu
                 75                  80                  85 ctg cac cag cag ctg cag gag ctg cac gcc cac gtg gtg ctt ccc gac        342
Leu His Gln Gln Leu Gln Glu Leu His Ala His Val Val Leu Pro Asp
             90                  95                 100 ccg gcg gcc acc cac gat ggc ccc cag tcc cct ggt gcg ggt ggc ccc        390
Pro Ala Ala Thr His Asp Gly Pro Gln Ser Pro Gly Ala Gly Gly Pro
        105                 110                 115 acc tgc tcg gcc acc aac ctg agc cgc gtg gcg ggc ctg gag aag cag        438
Thr Cys Ser Ala Thr Asn Leu Ser Arg Val Ala Gly Leu Glu Lys Gln
    120                 125                 130 ttg gcc att gag ctg aag gtg aag cag ggg gcg gag aac atg atc cag        486
Leu Ala Ile Glu Leu Lys Val Lys Gln Gly Ala Glu Asn Met Ile Gln
135                 140                 145                 150 acc tac agc aat ggc agc acc aag gac cgg aag ctg ctg ctg aca gcc        534
Thr Tyr Ser Asn Gly Ser Thr Lys Asp Arg Lys Leu Leu Leu Thr Ala
                155                 160                 165 cag cag atg ttg cag gac agt aag acc aag att gac atc atc cgc atg        582
Gln Gln Met Leu Gln Asp Ser Lys Thr Lys Ile Asp Ile Ile Arg Met
            170                 175                 180 caa ctc cgc cgg gcg ctg cag gcc ggc cag ctg gag aac cag gca gcc        630
Gln Leu Arg Arg Ala Leu Gln Ala Gly Gln Leu Glu Asn Gln Ala Ala
        185                 190                 195 ccg gat gac acc caa ggg agt cct gac ctg ggg gct gtg gag ctg cgc        678
Pro Asp Asp Thr Gln Gly Ser Pro Asp Leu Gly Ala Val Glu Leu Arg
    200                 205                 210 atc gaa gag ctg cgg cac cac ttc cga gtg gag cac gcg gtg gcc gag        726
Ile Glu Glu Leu Arg His His Phe Arg Val Glu His Ala Val Ala Glu
215                 220                 225                 230 ggt gcc aag aac gta ctg cgc ctg ctc agc gct gcc aag gcc ccg gac        774
Gly Ala Lys Asn Val Leu Arg Leu Leu Ser Ala Ala Lys Ala Pro Asp
                235                 240                 245
```

```
cgc aag gca gtc agc gag gcc cag gag aaa ttg aca gaa tcc aac cag      822
Arg Lys Ala Val Ser Glu Ala Gln Glu Lys Leu Thr Glu Ser Asn Gln
        250                 255                 260 aag ctg ggg ctg ctg cgg gag gct ctg gag cgg aga ctt ggg gag ctg      870
Lys Leu Gly Leu Leu Arg Glu Ala Leu Glu Arg Arg Leu Gly Glu Leu
        265                 270                 275 ccc gcc gac cac ccc aag ggg cgg ctg ctg cga gaa gag ctc gct gcg      918
Pro Ala Asp His Pro Lys Gly Arg Leu Leu Arg Glu Glu Leu Ala Ala
        280                 285                 290 gcc tcc tcc gct gcc ttc agc acc cgc ctg gcc ggg ccc ttt ccc gcc      966
Ala Ser Ser Ala Ala Phe Ser Thr Arg Leu Ala Gly Pro Phe Pro Ala
295                 300                 305                 310 acg cac tac agc acc ctg tgc aag ccc gcg ccg ctc aca ggg acc ctg     1014
Thr His Tyr Ser Thr Leu Cys Lys Pro Ala Pro Leu Thr Gly Thr Leu
                315                 320                 325 gag gta cga gtg gtg ggc tgc aga gac ctc cca gag acc atc ccg tgg     1062
Glu Val Arg Val Val Gly Cys Arg Asp Leu Pro Glu Thr Ile Pro Trp
                330                 335                 340 aac cct acc ccc tca atg ggg gga cct ggg acc cca gac agc cgc ccc     1110
Asn Pro Thr Pro Ser Met Gly Gly Pro Gly Thr Pro Asp Ser Arg Pro
                345                 350                 355 ccc ttc ctg agc cgc cca gcc cgg ggc ctt tac agc cga agc gga agc     1158
Pro Phe Leu Ser Arg Pro Ala Arg Gly Leu Tyr Ser Arg Ser Gly Ser
        360                 365                 370 ctc agt ggc cgg agc agc ctc aaa gca gaa gcc gag aac acc agt gaa     1206
Leu Ser Gly Arg Ser Ser Leu Lys Ala Glu Ala Glu Asn Thr Ser Glu
375                 380                 385                 390 gtc agc act gtg ctt aag ctg gat aac aca gtg gtg ggg cag acg tct     1254
Val Ser Thr Val Leu Lys Leu Asp Asn Thr Val Val Gly Gln Thr Ser
                395                 400                 405 tgg aag cca tgt ggc ccc aat gcc tgg gac cag agc ttc act ctg gag     1302
Trp Lys Pro Cys Gly Pro Asn Ala Trp Asp Gln Ser Phe Thr Leu Glu
                410                 415                 420 ctg gaa agg gca cgg gaa ctg gag ttg gct gtg ttc tgg cgg gac cag     1350
Leu Glu Arg Ala Arg Glu Leu Glu Leu Ala Val Phe Trp Arg Asp Gln
                425                 430                 435 cgg ggc ctg tgt gcc ctc aaa ttc ctg aag ttg gag gat ttc ttg gac     1398
Arg Gly Leu Cys Ala Leu Lys Phe Leu Lys Leu Glu Asp Phe Leu Asp
        440                 445                 450 aat gag agg cat gag gtg cag ctg gac atg gaa ccc cag ggc tgc ctg     1446
Asn Glu Arg His Glu Val Gln Leu Asp Met Glu Pro Gln Gly Cys Leu
455                 460                 465                 470 gtg gct gag gtc acc ttc cgc aac cct gtc att gag agg att cct cgg     1494
Val Ala Glu Val Thr Phe Arg Asn Pro Val Ile Glu Arg Ile Pro Arg
                475                 480                 485 ctc cga cgg cag aag aaa att ttc tcc aag cag caa ggg aag gcg ttc     1542
Leu Arg Arg Gln Lys Lys Ile Phe Ser Lys Gln Gln Gly Lys Ala Phe
        490                 495                 500 cag cgt gct agg cag atg aac atc gat gtc gcc acg tgg gtg cgg ctg     1590
Gln Arg Ala Arg Gln Met Asn Ile Asp Val Ala Thr Trp Val Arg Leu
        505                 510                 515 ctc cgg agg ctc atc ccc aat gcc acg ggc aca ggc acc ttt agc cct     1638
Leu Arg Arg Leu Ile Pro Asn Ala Thr Gly Thr Gly Thr Phe Ser Pro
        520                 525                 530 ggg gct tct cca gga tcc gag gcc cgg acc acg ggt gac ata tcg gtg     1686
Gly Ala Ser Pro Gly Ser Glu Ala Arg Thr Thr Gly Asp Ile Ser Val
535                 540                 545                 550 gag aag ctg aac ctc ggc act gac tcg gac agc tca cct cag aag agc     1734
Glu Lys Leu Asn Leu Gly Thr Asp Ser Asp Ser Ser Pro Gln Lys Ser
                555                 560                 565
```

-continued

| | |
|---|---|
| tcg cgg gat cct cct tcc agc cca tcg agc ctg agc tcc ccc atc cag<br>Ser Arg Asp Pro Pro Ser Ser Pro Ser Leu Ser Ser Pro Ile Gln<br>570                              575                        580 | 1782 |
| gaa tcc act gct ccc gag ctg cct tcg gag acc cag gag acc cca ggc<br>Glu Ser Thr Ala Pro Glu Leu Pro Ser Glu Thr Gln Glu Thr Pro Gly<br>585                              590                        595 | 1830 |
| ccc gcc ctg tgc agc cct ctg agg aag tca cct ctg acc ctc gaa gat<br>Pro Ala Leu Cys Ser Pro Leu Arg Lys Ser Pro Leu Thr Leu Glu Asp<br>600                              605                        610 | 1878 |
| ttc aag ttc ctg gcg gtg ctg ggc cgg ggt cat ttt ggg aag gtg ctc<br>Phe Lys Phe Leu Ala Val Leu Gly Arg Gly His Phe Gly Lys Val Leu<br>615                        620                        625                        630 | 1926 |
| ctc tcc gaa ttc cgg ccc agt ggg gag ctg ttc gcc atc aag gct ctg<br>Leu Ser Glu Phe Arg Pro Ser Gly Glu Leu Phe Ala Ile Lys Ala Leu<br>                    635                        640                        645 | 1974 |
| aag aaa ggg gac att gtg gcc cga gac gag gtg gag agc ctg atg tgt<br>Lys Lys Gly Asp Ile Val Ala Arg Asp Glu Val Glu Ser Leu Met Cys<br>                    650                        655                        660 | 2022 |
| gag aag cgg ata ttg gcg gca gtg acc agt gcg gga cac ccc ttc ctg<br>Glu Lys Arg Ile Leu Ala Ala Val Thr Ser Ala Gly His Pro Phe Leu<br>                    665                        670                        675 | 2070 |
| gtg aac ctc ttc ggc tgt ttc cag aca ccg gag cac gtg tgc ttc gtg<br>Val Asn Leu Phe Gly Cys Phe Gln Thr Pro Glu His Val Cys Phe Val<br>680                              685                        690 | 2118 |
| atg gag tac tcg gcc ggt ggg gac ctg atg ctg cac atc cac agc gac<br>Met Glu Tyr Ser Ala Gly Gly Asp Leu Met Leu His Ile His Ser Asp<br>695                              700                        705                        710 | 2166 |
| gtg ttc tct gag ccc cgt gcc atc ttt tat tcc gcc tgc gtg gtg ctg<br>Val Phe Ser Glu Pro Arg Ala Ile Phe Tyr Ser Ala Cys Val Val Leu<br>                    715                        720                        725 | 2214 |
| ggc cta cag ttt ctt cac gaa cac aag atc gtc tac agg gac ctg aag<br>Gly Leu Gln Phe Leu His Glu His Lys Ile Val Tyr Arg Asp Leu Lys<br>                    730                        735                        740 | 2262 |
| ttg gac aat ttg ctc ctg gac acc gag ggc tac gtc aag atc gca gac<br>Leu Asp Asn Leu Leu Leu Asp Thr Glu Gly Tyr Val Lys Ile Ala Asp<br>                  745                        750                        755 | 2310 |
| ttt ggc ctc tgc aag gag ggg atg ggc tat ggg gac cgg acc agc aca<br>Phe Gly Leu Cys Lys Glu Gly Met Gly Tyr Gly Asp Arg Thr Ser Thr<br>760                              765                        770 | 2358 |
| ttc tgt ggg acc ccg gag ttc ctg gcc cct gag gtg ctg acg gac acg<br>Phe Cys Gly Thr Pro Glu Phe Leu Ala Pro Glu Val Leu Thr Asp Thr<br>775                              780                        785                        790 | 2406 |
| tcg tac acg cga gct gtg gac tgg tgg gga ctg ggt gtg ctg ctc tac<br>Ser Tyr Thr Arg Ala Val Asp Trp Trp Gly Leu Gly Val Leu Leu Tyr<br>                    795                        800                        805 | 2454 |
| gag atg ctg gtt ggc gag tcc cca ttc cca ggg gat gat gag gag gag<br>Glu Met Leu Val Gly Glu Ser Pro Phe Pro Gly Asp Asp Glu Glu Glu<br>                  810                        815                        820 | 2502 |
| gtc ttc gac agc atc gtc aac gac gag gtt cgc tac ccc cgc ttc ctg<br>Val Phe Asp Ser Ile Val Asn Asp Glu Val Arg Tyr Pro Arg Phe Leu<br>825                              830                        835 | 2550 |
| tcg gcc gaa gcc atc ggc atc atg aga agg ctg ctt cgg agg aac cca<br>Ser Ala Glu Ala Ile Gly Ile Met Arg Arg Leu Leu Arg Arg Asn Pro<br>                  840                        845                        850 | 2598 |
| gag cgg agg ctg gga tct agc gag aga gat gca gaa gat gtg aag aaa<br>Glu Arg Arg Leu Gly Ser Ser Glu Arg Asp Ala Glu Asp Val Lys Lys<br>855                              860                        865                        870 | 2646 |
| cag ccc ttc ttc agg act ctg ggc tgg gaa gcc ctg ttg gcc cgg cgc<br>Gln Pro Phe Phe Arg Thr Leu Gly Trp Glu Ala Leu Leu Ala Arg Arg | 2694 |

-continued

```
                    875                 880                 885
ctg cca ccg ccc ttt gtg ccc acg ctg tcc ggc cgc acc gac gtc agc      2742
Leu Pro Pro Pro Phe Val Pro Thr Leu Ser Gly Arg Thr Asp Val Ser
                890                 895                 900 aac ttc gac gag gag ttc acc ggg gag gcc ccc aca ctg agc ccg ccc      2790
Asn Phe Asp Glu Glu Phe Thr Gly Glu Ala Pro Thr Leu Ser Pro Pro
            905                 910                 915 cgc gac gcg cgg ccc ctt aca gcc gcg gag cag gca gcc ttc ctg gac      2838
Arg Asp Ala Arg Pro Leu Thr Ala Ala Glu Gln Ala Ala Phe Leu Asp
        920                 925                 930 ttc gac ttc gtg gcc ggg ggc tgc tagccccctc ccctgcccct gccctgccc      2892
Phe Asp Phe Val Ala Gly Gly Cys
935                 940 ctgcccgaga gctcttagtt tttaaaaagg cctttgggat ttgccggaaa aaaaaaaaa      2952 aaaaaaaaag gaattc                                                    2968
```

<210> SEQ ID NO 2
<211> LENGTH: 15
<212> TYPE: PRT
<213> ORGANISM: Homo sapiens

<400> SEQUENCE: 2

Arg Glu Arg Leu Arg Arg Glu Ser Arg Lys Glu Leu Lys Leu Lys
1               5                   10                  15

<210> SEQ ID NO 3
<211> LENGTH: 942
<212> TYPE: PRT
<213> ORGANISM: Homo sapiens

<400> SEQUENCE: 3

Met Ala Ser Asp Ala Val Gln Ser Glu Pro Arg Ser Trp Ser Leu Leu
1               5                   10                  15

Glu Gln Leu Gly Leu Ala Gly Ala Asp Leu Ala Ala Pro Gly Val Gln
            20                  25                  30

Gln Gln Leu Glu Leu Glu Arg Glu Arg Leu Arg Arg Glu Ile Arg Lys
        35                  40                  45

Glu Leu Lys Leu Lys Glu Gly Ala Glu Asn Leu Arg Arg Ala Thr Thr
    50                  55                  60

Asp Leu Gly Arg Ser Leu Gly Pro Val Glu Leu Leu Leu Arg Gly Ser
65              70                  75                  80

Ser Arg Arg Leu Asp Leu Leu His Gln Gln Leu Gln Glu Leu His Ala
                85                  90                  95

His Val Val Leu Pro Asp Pro Ala Thr His Asp Gly Pro Gln Ser
            100                 105                 110

Pro Gly Ala Gly Gly Pro Thr Cys Ser Ala Thr Asn Leu Ser Arg Val
        115                 120                 125

Ala Gly Leu Glu Lys Gln Leu Ala Ile Glu Leu Lys Val Lys Gln Gly
    130                 135                 140

Ala Glu Asn Met Ile Gln Thr Tyr Ser Asn Gly Ser Thr Lys Asp Arg
145                 150                 155                 160

Lys Leu Leu Leu Thr Ala Gln Gln Met Leu Gln Asp Ser Lys Thr Lys
                165                 170                 175

Ile Asp Ile Ile Arg Met Gln Leu Arg Arg Ala Leu Gln Ala Gly Gln
            180                 185                 190

Leu Glu Asn Gln Ala Ala Pro Asp Asp Thr Gln Gly Ser Pro Asp Leu
        195                 200                 205

```
Gly Ala Val Glu Leu Arg Ile Glu Glu Leu Arg His His Phe Arg Val
    210                 215                 220
Glu His Ala Val Ala Glu Gly Ala Lys Asn Val Leu Arg Leu Leu Ser
225                 230                 235                 240
Ala Ala Lys Ala Pro Asp Arg Lys Ala Val Ser Glu Ala Gln Glu Lys
                245                 250                 255
Leu Thr Glu Ser Asn Gln Lys Leu Gly Leu Leu Arg Glu Ala Leu Glu
            260                 265                 270
Arg Arg Leu Gly Glu Leu Pro Ala Asp His Pro Lys Gly Arg Leu Leu
        275                 280                 285
Arg Glu Glu Leu Ala Ala Ala Ser Ser Ala Ala Phe Ser Thr Arg Leu
    290                 295                 300
Ala Gly Pro Phe Pro Ala Thr His Tyr Ser Thr Leu Cys Lys Pro Ala
305                 310                 315                 320
Pro Leu Thr Gly Thr Leu Glu Val Arg Val Val Gly Cys Arg Asp Leu
                325                 330                 335
Pro Glu Thr Ile Pro Trp Asn Pro Thr Pro Ser Met Gly Gly Pro Gly
            340                 345                 350
Thr Pro Asp Ser Arg Pro Pro Phe Leu Ser Arg Pro Ala Arg Gly Leu
        355                 360                 365
Tyr Ser Arg Ser Gly Ser Leu Ser Gly Arg Ser Ser Leu Lys Ala Glu
    370                 375                 380
Ala Glu Asn Thr Ser Glu Val Ser Thr Val Leu Lys Leu Asp Asn Thr
385                 390                 395                 400
Val Val Gly Gln Thr Ser Trp Lys Pro Cys Gly Pro Asn Ala Trp Asp
                405                 410                 415
Gln Ser Phe Thr Leu Glu Leu Glu Arg Ala Arg Glu Leu Glu Leu Ala
            420                 425                 430
Val Phe Trp Arg Asp Gln Arg Gly Leu Cys Ala Leu Lys Phe Leu Lys
        435                 440                 445
Leu Glu Asp Phe Leu Asp Asn Glu Arg His Glu Val Gln Leu Asp Met
    450                 455                 460
Glu Pro Gln Gly Cys Leu Val Ala Glu Val Thr Phe Arg Asn Pro Val
465                 470                 475                 480
Ile Glu Arg Ile Pro Arg Leu Arg Arg Gln Lys Lys Ile Phe Ser Lys
                485                 490                 495
Gln Gln Gly Lys Ala Phe Gln Arg Ala Arg Gln Met Asn Ile Asp Val
            500                 505                 510
Ala Thr Trp Val Arg Leu Leu Arg Arg Leu Ile Pro Asn Ala Thr Gly
        515                 520                 525
Thr Gly Thr Phe Ser Pro Gly Ala Ser Pro Gly Ser Glu Ala Arg Thr
    530                 535                 540
Thr Gly Asp Ile Ser Val Glu Lys Leu Asn Leu Gly Thr Asp Ser Asp
545                 550                 555                 560
Ser Ser Pro Gln Lys Ser Ser Arg Asp Pro Ser Ser Pro Ser Ser
                565                 570                 575
Leu Ser Ser Pro Ile Gln Glu Ser Thr Ala Pro Glu Leu Pro Ser Glu
            580                 585                 590
Thr Gln Glu Thr Pro Gly Pro Ala Leu Cys Ser Pro Leu Arg Lys Ser
        595                 600                 605
Pro Leu Thr Leu Glu Asp Phe Lys Phe Leu Ala Val Leu Gly Arg Gly
    610                 615                 620
```

-continued

His Phe Gly Lys Val Leu Leu Ser Glu Phe Arg Pro Ser Gly Glu Leu
625                 630                 635                 640

Phe Ala Ile Lys Ala Leu Lys Lys Gly Asp Ile Val Ala Arg Asp Glu
            645                 650                 655

Val Glu Ser Leu Met Cys Glu Lys Arg Ile Leu Ala Ala Val Thr Ser
                660                 665                 670

Ala Gly His Pro Phe Leu Val Asn Leu Phe Gly Cys Phe Gln Thr Pro
            675                 680                 685

Glu His Val Cys Phe Val Met Glu Tyr Ser Ala Gly Gly Asp Leu Met
        690                 695                 700

Leu His Ile His Ser Asp Val Phe Ser Glu Pro Arg Ala Ile Phe Tyr
705                 710                 715                 720

Ser Ala Cys Val Val Leu Gly Leu Gln Phe Leu His Glu His Lys Ile
                725                 730                 735

Val Tyr Arg Asp Leu Lys Leu Asp Asn Leu Leu Leu Asp Thr Glu Gly
            740                 745                 750

Tyr Val Lys Ile Ala Asp Phe Gly Leu Cys Lys Glu Gly Met Gly Tyr
            755                 760                 765

Gly Asp Arg Thr Ser Thr Phe Cys Gly Thr Pro Glu Phe Leu Ala Pro
770                 775                 780

Glu Val Leu Thr Asp Thr Ser Tyr Thr Arg Ala Val Asp Trp Trp Gly
785                 790                 795                 800

Leu Gly Val Leu Leu Tyr Glu Met Leu Val Gly Glu Ser Pro Phe Pro
                805                 810                 815

Gly Asp Asp Glu Glu Glu Val Phe Asp Ser Ile Val Asn Asp Glu Val
            820                 825                 830

Arg Tyr Pro Arg Phe Leu Ser Ala Glu Ala Ile Gly Ile Met Arg Arg
            835                 840                 845

Leu Leu Arg Arg Asn Pro Glu Arg Arg Leu Gly Ser Ser Glu Arg Asp
850                 855                 860

Ala Glu Asp Val Lys Lys Gln Pro Phe Phe Arg Thr Leu Gly Trp Glu
865                 870                 875                 880

Ala Leu Leu Ala Arg Arg Leu Pro Pro Pro Phe Val Pro Thr Leu Ser
            885                 890                 895

Gly Arg Thr Asp Val Ser Asn Phe Asp Glu Glu Phe Thr Gly Glu Ala
            900                 905                 910

Pro Thr Leu Ser Pro Pro Arg Asp Ala Arg Pro Leu Thr Ala Ala Glu
            915                 920                 925

Gln Ala Ala Phe Leu Asp Phe Asp Phe Val Ala Gly Gly Cys
    930                 935                 940

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 4
aatttggatc cttgcagagt gagcctcgca                                    30

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Primer -continued

```
<400> SEQUENCE: 5
tatatggatc ctcagccatt gctgtaggtc tggat                          35

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Met Phe Pro Thr Met Asn Arg Arg Gly Ser Ile Lys Gln Ala Lys
 1               5                  10                  15

Ile
```

What is claimed is:

1. An isolated peptide having activated Rho protein binding activity and not having protein kinase activity, consisting of a peptide fragment of the amino acid sequence 1–613 of SEQ ID NO:3.

2. An isolated peptide according to claim 1, wherein the peptide fragment consists of the amino acid sequence 7–540, 7–155, 1–540, 3–135, or 33–111 of SEQ ID NO:3.

3. An isolated peptide according to claim 1, wherein the peptide fragment consists of the amino acid sequence 74–93, 94–113, or 82–103 of SEQ ID NO:3.

4. An isolated peptide having intermediate filament binding activity and not having protein kinase activity, consisting of a peptide fragment of the amino acid sequence 1–613 of SEQ ID NO:3.

5. An isolated peptide according to claim 4, wherein the peptide fragment consists of the amino acid sequence 1–540, 1–32, 112–540, or 112–474 of SEQ ID NO:3.

* * * * *